US010363299B2

(12) United States Patent
Woodfolk et al.

(10) Patent No.: US 10,363,299 B2
(45) Date of Patent: Jul. 30, 2019

(54) COMPOSITIONS AND METHODS FOR PREVENTING AND TREATING RHINOVIRUS INFECTIONS

(71) Applicants: University of Virginia Patent Foundation, Charlottesville, VA (US); Benaroya Research Institute at Virginia Mason, Seattle, WA (US)

(72) Inventors: Judith Ann Woodfolk, Keswick, VA (US); Lyndsey M. Muehling, Charlottesville, VA (US); William W. Kwok, Bellevue, WA (US); Duy Tran Mai, Seattle, WA (US)

(73) Assignees: UNIVERSITY OF VIRGINIA PATENT FOUNDATION, Charlottesville, VA (US); BENAROYA RESEARCH INSTITUTE AT VIRGINIA MASON, Seattle, WA (US)

( * ) Notice: Subject to any disclaimer, the term of this patent is extended or adjusted under 35 U.S.C. 154(b) by 0 days.

(21) Appl. No.: 15/551,315

(22) PCT Filed: Feb. 19, 2016

(86) PCT No.: PCT/US2016/018723
§ 371 (c)(1),
(2) Date: Aug. 16, 2017

(87) PCT Pub. No.: WO2016/134288
PCT Pub. Date: Aug. 25, 2016

(65) Prior Publication Data

US 2018/0043006 A1 Feb. 15, 2018

Related U.S. Application Data

(60) Provisional application No. 62/118,084, filed on Feb. 19, 2015.

(51) Int. Cl.
| | |
|---|---|
| *A61K 38/00* | (2006.01) |
| *C07K 14/005* | (2006.01) |
| *C07K 14/02* | (2006.01) |
| *A61K 39/00* | (2006.01) |
| *C07K 14/155* | (2006.01) |
| *A61K 39/12* | (2006.01) |
| *C12Q 1/70* | (2006.01) |
| *G01N 33/569* | (2006.01) |

(52) U.S. Cl.

CPC ................ *A61K 39/12* (2013.01); *C12Q 1/70* (2013.01); *G01N 33/56983* (2013.01); *A61K 2039/58* (2013.01); *C12N 2770/32722* (2013.01); *C12N 2770/32734* (2013.01)

(58) Field of Classification Search
CPC ........ C07K 14/005; C12N 2730/10122; C12N 2740/16222; C12N 2740/15022; A61K 38/00

See application file for complete search history.

(56) References Cited

U.S. PATENT DOCUMENTS 8,153,760 B2 4/2012 Smith et al.

FOREIGN PATENT DOCUMENTS

| | | | |
|---|---|---|---|
| WO | WO2014122220 | * | 8/2014 |
| WO | WO 2014122220 | | 8/2014 |
| WO | WO2014140166 | | 9/2014 |

OTHER PUBLICATIONS

Glanville, et al., "Cross-Serotype Immunity Induced by Immunization with a Conserved Rhinovirus Capsid Protein," PLoS Pathogens, Sep. 26, 2013 (Sep. 26, 2013), vol. 9, e1003669, pp. 1-11, entire document.

McLean, et al., "Rhinovirus infections and immunisation induce cross-serotype reactive antibodies to VP1," Antiviral Research, Jun. 26, 2012 (Jun. 26, 2012), vol. 95, pp. 193-201, entire document.

Iwasaki, J., et al., "Species-Specific and Cross-Reactive IgG1 Antibody Binding to Viral Capsid Protein 1 (VP1) Antigens of Human Rhinovirus Species A, B and C", PLoS One, 2013; 8(8) 370552.

Basta, H., et al., "Modeling of the human rhinovirus C capsid suggests a novel topography with insights on receptor preference and immunogenicity", Virology, 2014, 448, 176-84.

Hastings, GZ, et al., "Proliferative responses of T cells primed against human rhinovirus to other rhinovirus serotypes", J. Gen. Virology, 1991;72, 2947-52.

(Continued)

*Primary Examiner* — Barry A Chestnut
(74) *Attorney, Agent, or Firm* — Jenkins, Wilson, Taylor & Hunt, P.A.; Rodney L. Sparks

(57) ABSTRACT

An analysis of human $CD4^+$ T-cell epitopes of RV capsid proteins with cross-reactive potential was performed, peptide epitopes of RV-A16 capsid proteins VP1 and VP2 were identified, RV-specific $CD4^+$ T cells were phenotyped for surface markers and cytokine profiles using flow cytometry, and it was found that, among non-infected subjects, circulating RV-A16-specific $CD4^+$ T cells detected at the highest frequencies targeted 10 unique epitopes with diverse HLA-DR binding capacity. T-cell epitopes localized to conserved regions of significance to the virus and were enriched for HLA class I and II binding motifs and were activated in vivo after experimental infection with RV-A16. RV-A16 epitopes constituted species-specific and pan-species varieties, together providing ~90% coverage of the US population. Cross-reactivity was evidenced for RV-A16 and RV-A39. High-frequency circulating RV-specific memory Th1 cells in healthy individuals preferentially target a limited set of conserved epitopes and these epitopes, separately or combined, can serve as vaccines.

29 Claims, 43 Drawing Sheets
(13 of 43 Drawing Sheet(s) Filed in Color)
Specification includes a Sequence Listing.

(56) References Cited

OTHER PUBLICATIONS

Gillian Z. Hastings, et al., "Epitope analysis of the T cell response to a complex antigen: Proliferative responses to human rhinovirus capsids", European Journal of Immunology, vol. 23, No. 9, Sep. 1, 1993 (Sep. 1, 1993), pp. 2300-2305, XP055359058, ISSN: 0014-2980, DOI: 10.1001/eji.1830230937, *abstract figure 2; table 2*.

John W. Steinke, et al., "Immune Surveillance by Rhinovirus-Specific Circulating CD4+ and CD8+ T Lymphyocytes", PLOS One, vol. 10, No. 1, Jan. 13, 2015 (Jan. 13, 2015), p. e0115271, XP055483579, DOI: 10.1371/journal.pone.0115271, *p. 1; figure 4; table 2*.

James E. Gem, et al., "Rhinovirus-Specific T Cells Recognize both Shared and Serotype-Restricted Viral Epitopes", Journal of Infectious Diseases, JID, vol. 175, No. 5, May 1997 (May 1, 1997, pp. 1108-1114, XP55484327, US, ISSN: 0022-1899, DOI: 10.1086/516449, *p. 1109, col. 2; figure 3*.

Muehling, et al., :Circulating Rhinovirus-Specific CD4+ T Cells in Uninfected Subjects Recognize Conserved Epitopes Journal of Allergy and Clinical Immunology, The, Feb. 21, 2015 (Feb. 21, 2015), pp. AB164-AB164, XP55484354, St. Louis, DOI: 10.1016/j.jaci.2014.12.1473. *abstract*.

Novak, E.J., et al., "Tetramer-guided epitope mapping: rapid identification and characterization of immunodominant CD4+ T cell epitopes from complex antigents", The Journal of Immunology, The American Association of Immunologists, US, vol. 166, No. 11, Jun. 1, 2001 (Jun. 1, 2001), pp. 6665-6670, XP002271781, ISSN: 0022-1767, *p. 6668-p.6670*.

Lyndsey M. Mueling, et al, "Circulating Memory CD4 + T Cells Target Conserved Epitopes of Rhinovirus Capsid Proteins and Respond Rapidly to Experimental Infection in Humans", The Journal of Immunology, vol. 197, No. 8, Sep. 2, 2016 (Sep. 2, 2016), pp. 3214-3224, XP55483544, US, ISSN: 0022-1767, DOI: 10.4049/immunol.1600663, *the whole document*.

* cited by examiner

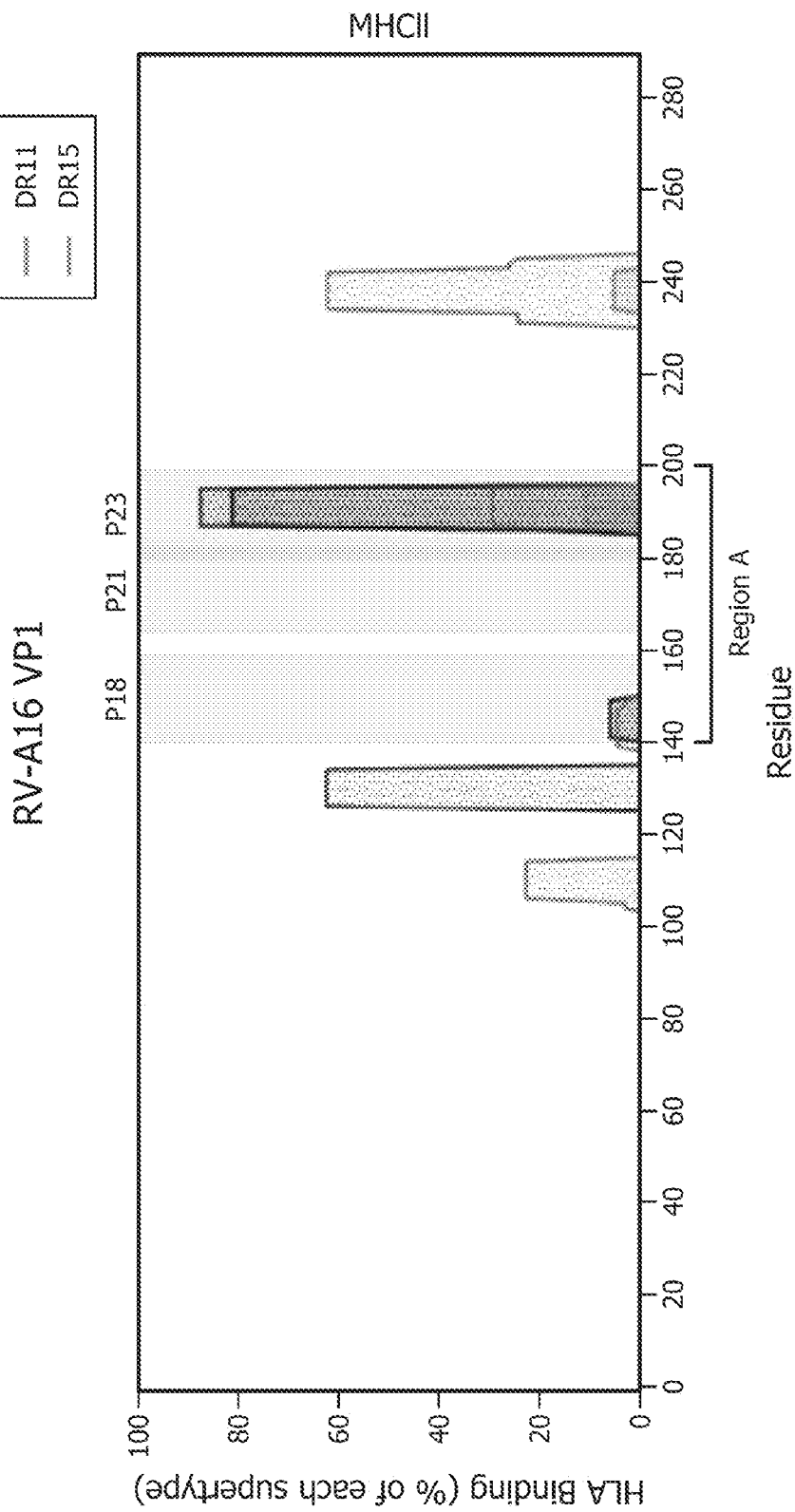
FIG. 3A1

FIG. 3A2

RV-A16 VP2 MHCII

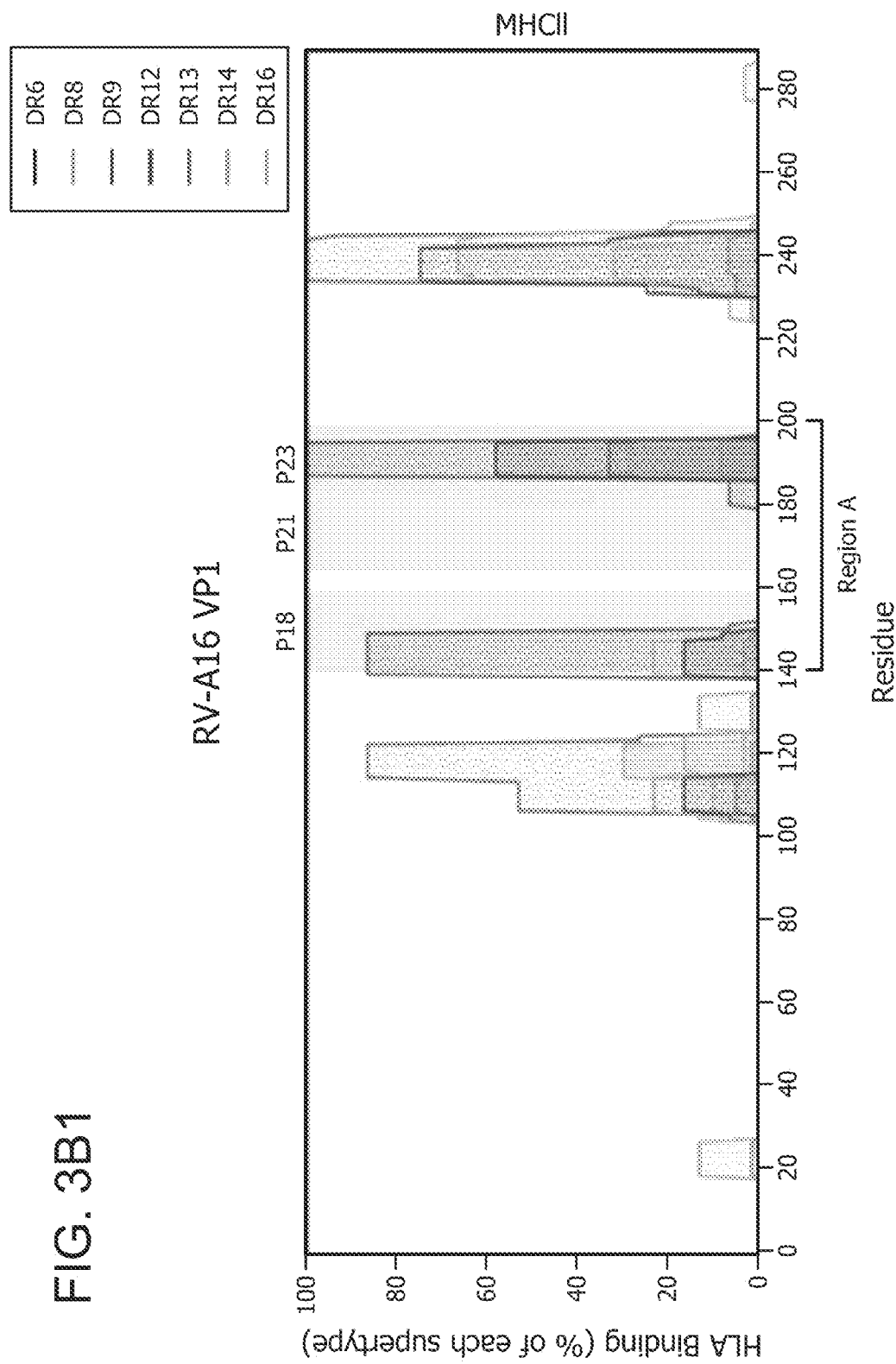
FIG. 3B1

FIG. 3B2

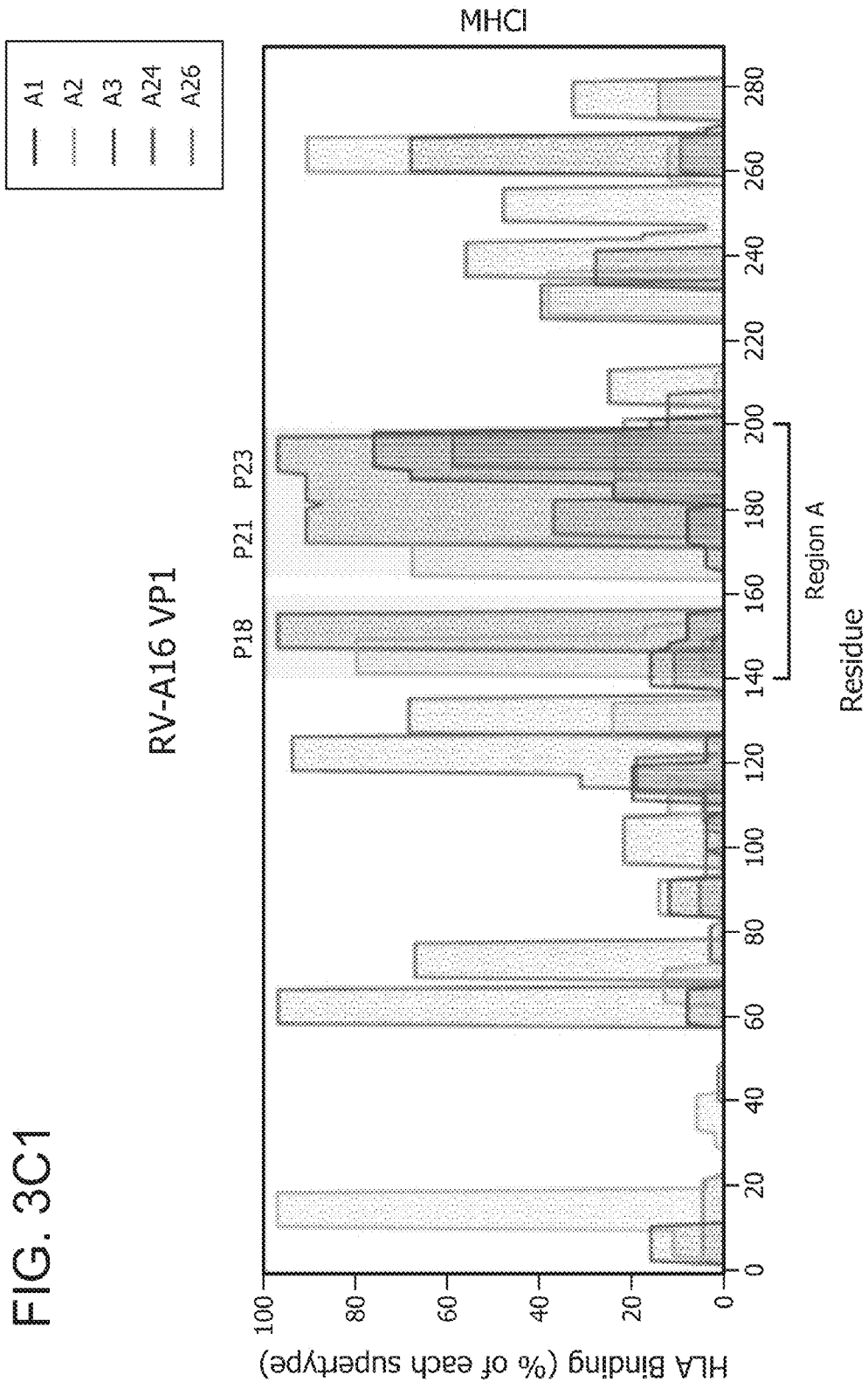
FIG. 3C1

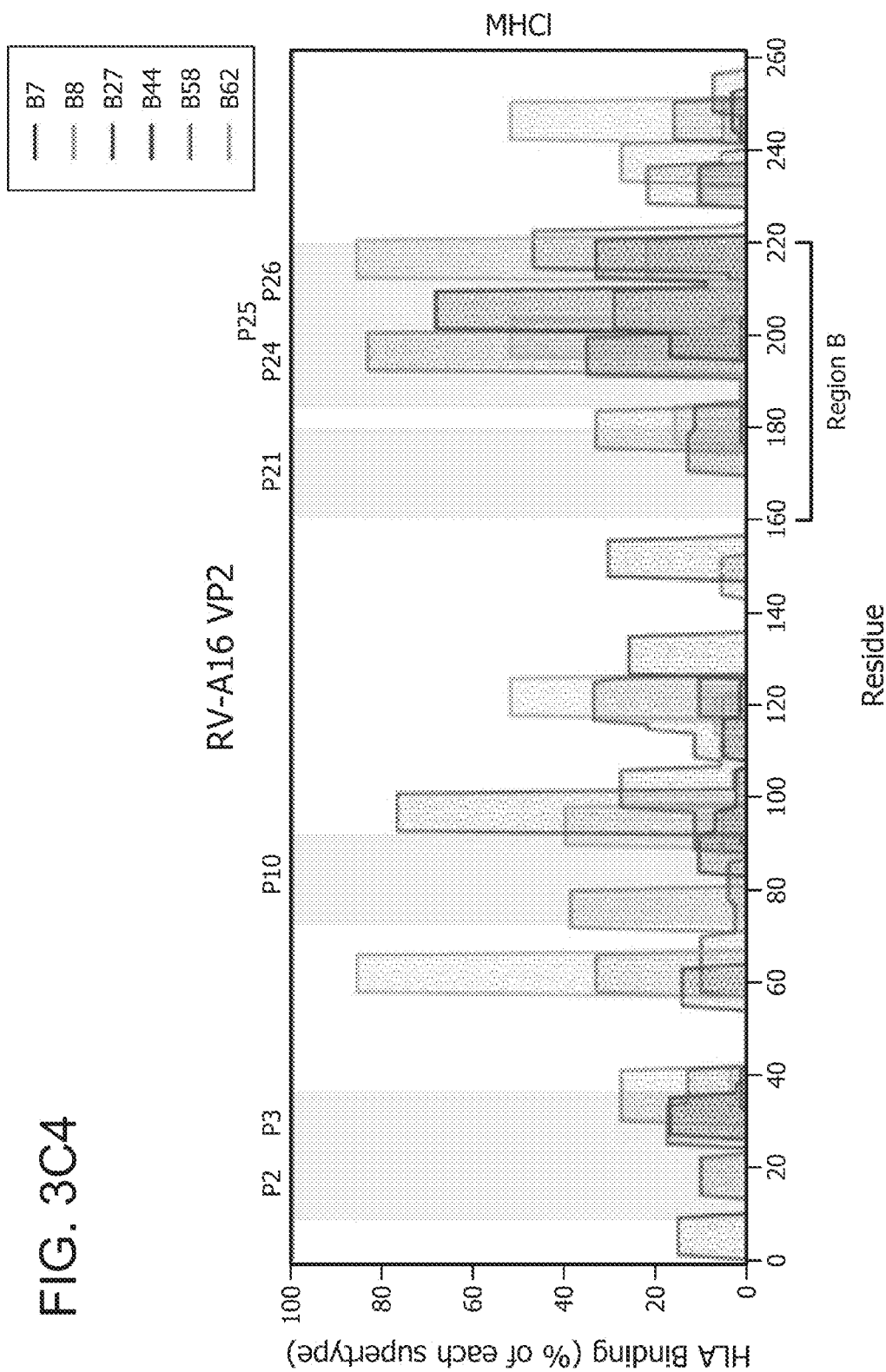
FIG. 3C4

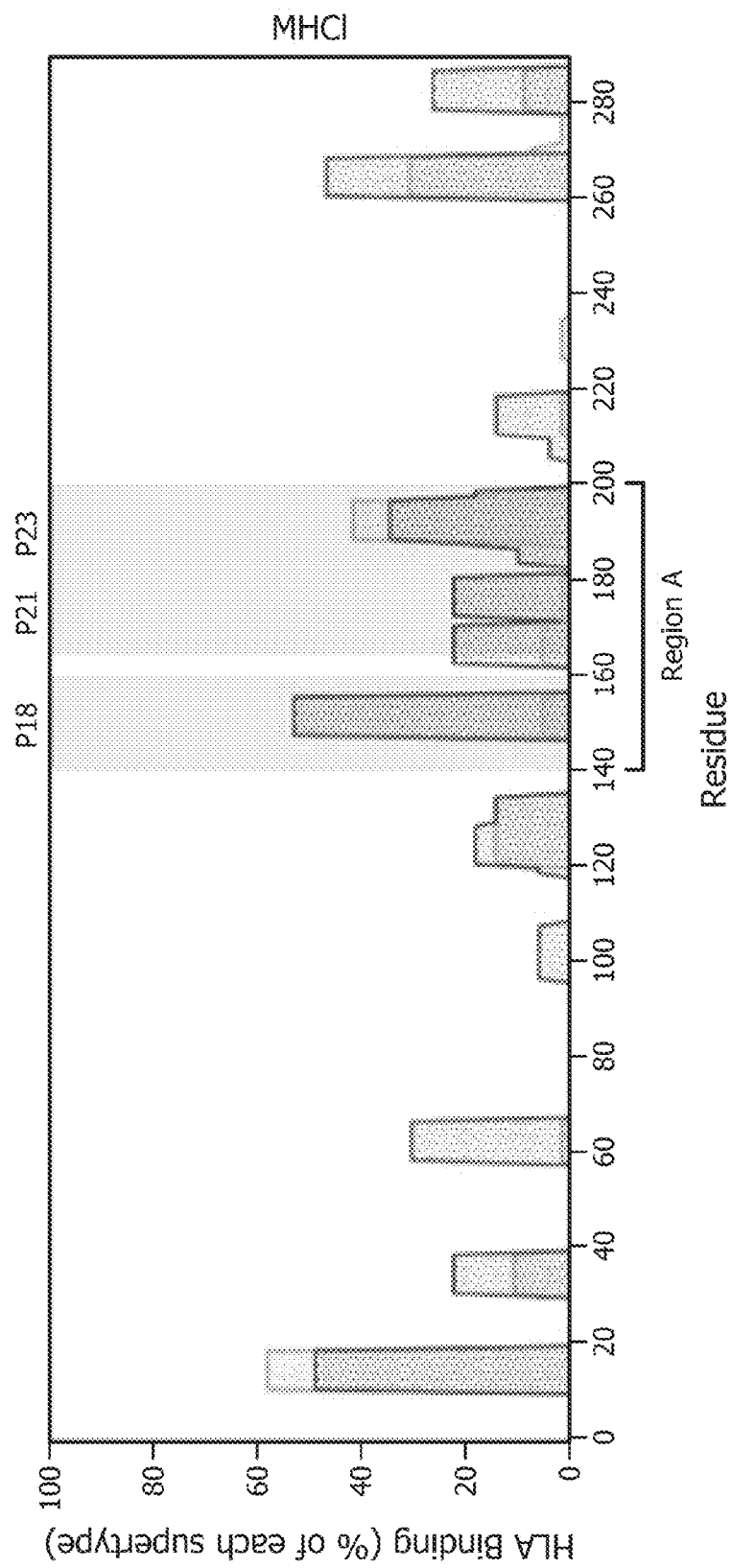
FIG. 3C5

FIG. 3C6

RV-A39 VP1 105-124　　AQVRKFEMFTYVRFDSEIT
RV-A16 VP1　　　　　　QIRRKFEMFTYARFDSEITM

RV-A39 VP2 169-188　　SDDNWLNFDGTLLGNLLIFP
RV-A16 VP2 p24　　　　　NWLNFDGTLLGNLLIFPHQPF

FIG. 6A

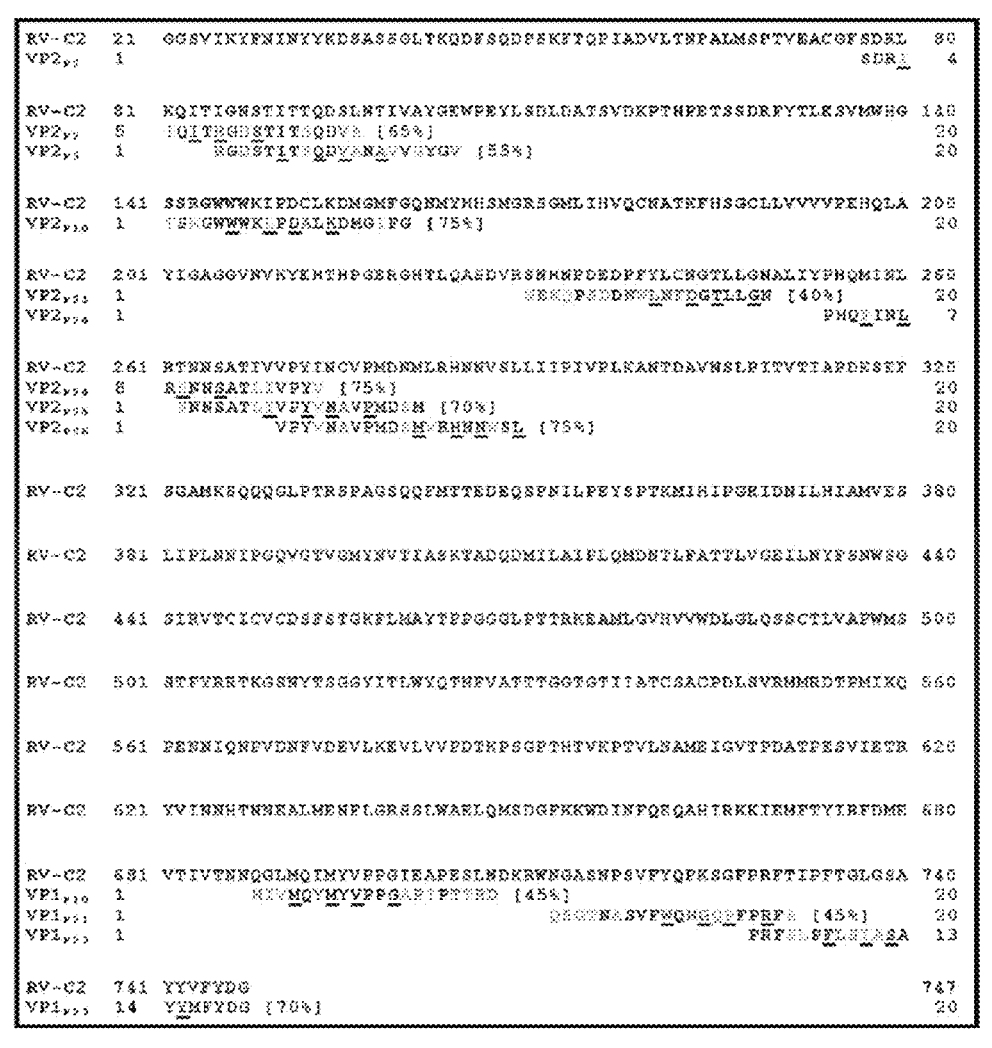

```
RV-C2    21  GGSVIKTFNINYYKD

FIG. 9

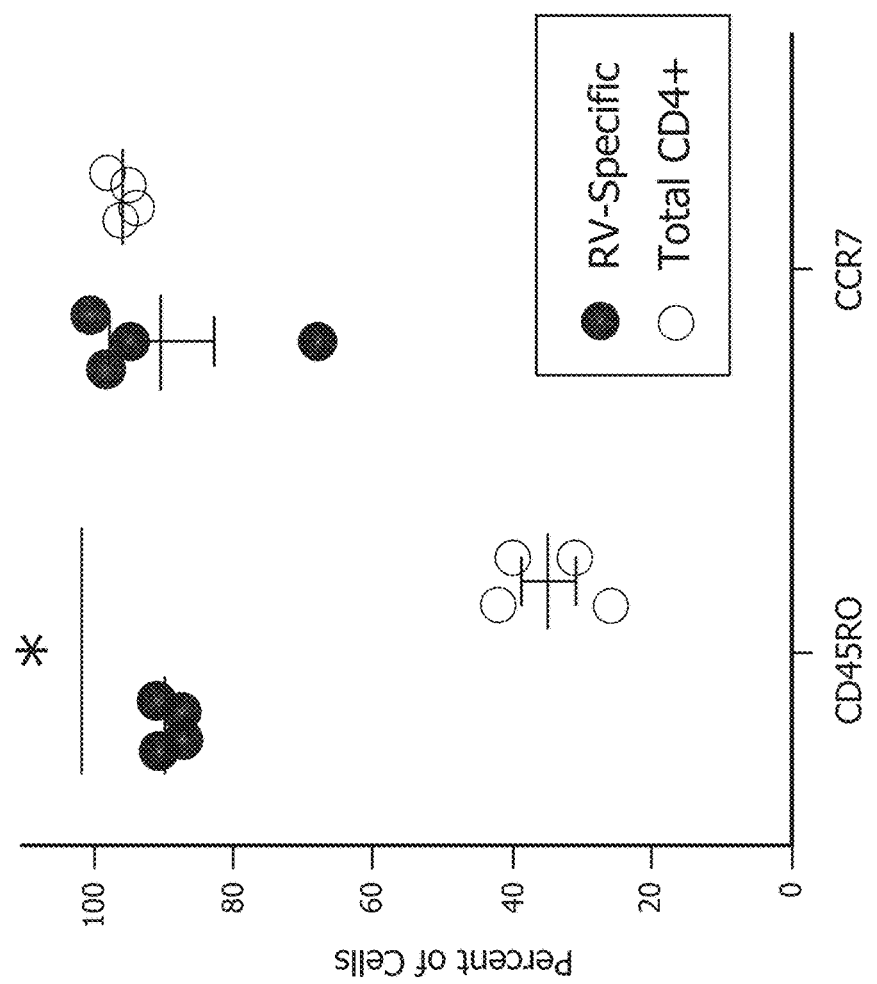

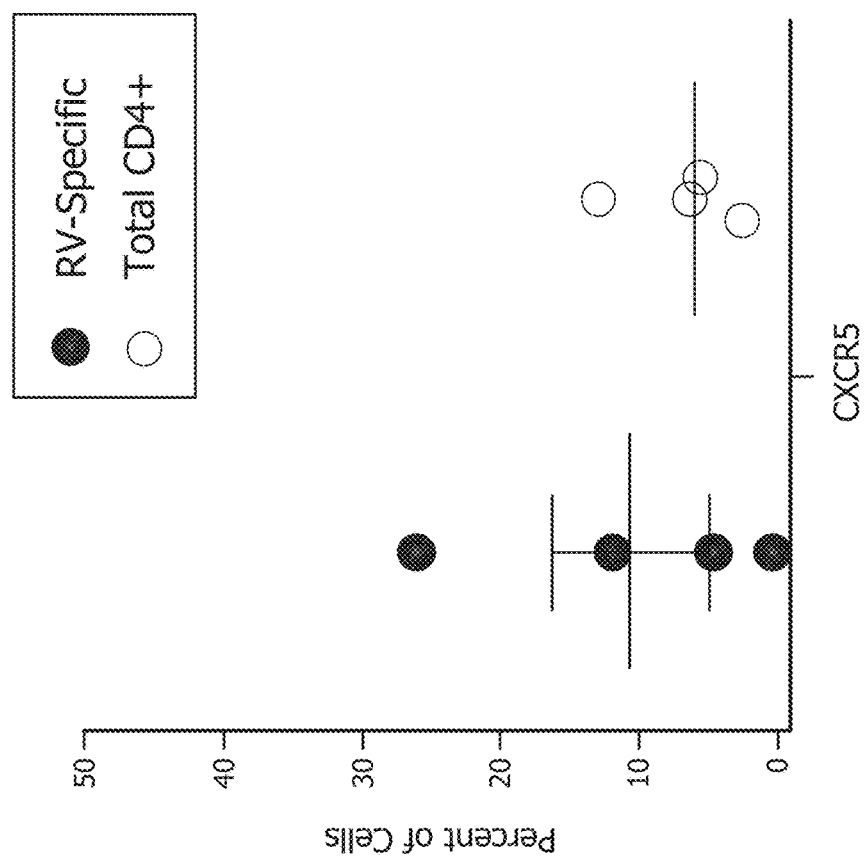

FIG. 15

COMPOSITIONS AND METHODS FOR PREVENTING AND TREATING RHINOVIRUS INFECTIONS

CROSS REFERENCE TO RELATED APPLICATIONS

This application is a national stage filing of International Application No. PCT/US2016/018723, filed Feb. 19, 2016, which claims priority under 35 U.S.C. § 119(e) to U.S. Provisional Application Ser. No. 62/118,084 filed Feb. 19, 2015, the disclosure of which is incorporated by reference in its entirety herein.

STATEMENT REGARDING FEDERALLY SPONSORED RESEARCH OR DEVELOPMENT

This invention was made with government support under Grant No. AI100799, awarded by The National Institutes of Health. The government has certain rights in the invention.

BACKGROUND

Rhinovirus infection is a major cause of the common cold and an important trigger of disease exacerbations in children and adults with allergic asthma. Infections occur frequently owing to variability among the numerous serotypes of rhinovirus and the consequent barrier to mounting protective responses upon exposure to unrelated strains.

Human rhinovirus (RV) accounts for up to half of all adult cases of common cold. Children experience 8 to 12 infections annually, while the infection rate is lower in adults (~2-3 per year). RV infection poses serious health risks among children and young adults with allergic asthma, by inducing disease exacerbations that are often severe. Moreover, RV has been implicated in the development of asthma in early childhood. Despite the enormous public health burden, there is no intervention to prevent RV infection. Notably, whereas asthma exacerbations can be prevented by blockade of IgE, this approach has major practical limitations. T-cell-based strategies to prevent RV infection would have the major advantage of conferring long-lasting protection in the first decades of life, when asthmatics are most susceptible to adverse respiratory sequelae.

Human rhinovirus is a single-stranded RNA virus of ~7,200 bp belonging to the picornaviridae family. RV infection results in production of serotype-specific neutralizing serum antibodies at 1-2 weeks post-infection which can persist for a year. These antibodies confer protection from re-infection and reduce symptom severity upon experimental challenge with the same serotype. However, cross-neutralization among the more than 100 serotypes identified to date is limited owing to the high degree of variability among different RV strains. This results in frequent infections and poses a major challenge to vaccine development.

Activation of RV-specific CD4+ T cells is a critical antecedent to IgG responses. Despite this, little is known regarding the properties of CD4+ T cells that contribute to protection. This can be attributed, at least in part, to the lack of robust mouse models of RV infection, and to challenges in identifying and tracking rare RV-specific T cells in humans. Studies performed over 15 years ago reported the ability for RV-specific T cells cloned from tonsils or peripheral blood to be activated by either serotype-specific or cross-reactive epitopes.

Though earlier work implied that Th1 effector cells were integral to the protective response against RV, no studies formally tested this theory, which has since become dogma. It is now recognized that naïve CD4+ T cells develop into a variety of specialized T-cell subsets under the control of lineage-specifying transcription factors. These subsets include "conventional" effector (Teff) types (e.g., Th1, Th2 and Th17), as well as T follicular helper (Tfh) cells. Recent work in animal models indicates that Tfh cells, which provide help to B cells in germinal centers for antibody responses, persist as memory T cells following acute viral infection.

There is a long felt need in the art for compositions and method useful for preventing and treating Rhinovirus infections and for determining how to prevent and treat such infections. The present invention satisfies these needs.

SUMMARY OF THE INVENTION

Disclosed herein is the first comprehensive analysis of human CD4+ T-cell epitopes of RV capsid proteins with cross-reactive potential, and an assessment of the protective attributes of cognate T cells in healthy individuals.

Peptide epitopes of RV-A16 capsid proteins VP1 and VP2 were identified herein by peptide/MHCII tetramer-guided epitope mapping (TGEM), validated by direct ex vivo enumeration, and interrogated using in silico methods. RV-specific CD4+ T cells were phenotyped for surface markers and cytokine profiles using flow cytometry. Among non-infected subjects, those circulating RV-A16-specific CD4+ T cells detected at the highest frequencies targeted 10 unique epitopes (SEQ ID NOs:1-10) with diverse HLA-DR binding capacity (a list of sequences is provided at the end of this "Summary" section, as well as in the Sequence Listing). T-cell epitopes localized to conserved molecular regions of biological significance to the virus and were enriched for HLA class I and II binding motifs. RV-A16 epitopes constituted both species-specific (RV-A) and pan-species (RV-A, -B and -C) varieties, and together provided ~90% coverage of the U.S. population. Circulating epitope-specific T cells comprised both memory Th1 cells and T follicular helper cells, and were activated in vivo after experimental infection with RV-A16. Cross-reactivity was evidenced by identification of corresponding epitopes for RV-A16 and RV-A39 by TGEM, and the ability for RV-A16-specific T cells to expand in response to their RV-A39 peptide counterpart. Our findings demonstrate that high-frequency circulating RV-specific memory Th1 cells in healthy individuals preferentially target a limited set of conserved epitopes. We propose that peptide vaccines designed to boost these cells might provide broad cross-protection against multiple RV strains.

Disclosed herein is the discovery that, in at least some subjects, there are circulating antigen-experienced RV-specific CD4+ T cells directed against highly conserved regions of capsid proteins in some non-infected subjects, and that there is an expansion of those cells during acute infection. That is, the present application is based on the discovery that certain RV epitopes are associated with certain antigen-experienced T cells. The present application discloses specific RV epitopes associated with memory T cells and further discloses that these RV epitopes can be used to activate the T cells and can be used as vaccines. Notably, also disclosed herein is that a higher frequency of these cells pre-infection is associated with a lower rate of infection following experimental RV inoculation. The present invention therefore provides compositions and methods for determining whether antigen-experienced cells are present in a subject and compositions and methods useful as vaccines against RV infection. The data disclosed herein imply a protective role for pre-existing RV-specific CD4⁺ T cell directed against conserved epitopes. The data disclosed herein suggest that memory T cells persist at highest numbers following infection, and that they are capable of responding upon re-infection with rhinovirus, and that the cells preferentially target conserved epitopes.

In one embodiment, the invention encompasses preventing and treating infections for rhinoviruses of multiple serotypes. In one aspect, the epitopes shared by the rhinoviruses, as far as a conserved epitope is concerned, may be considered to be shared by a variety of strains of rhinovirus when the T cells of the invention recognize all of them in the "shared" group. This is based on the disclosure herein identifying "shared rhinovirus antigens" that are conserved across multiple rhinovirus types and are capable of being recognized by CD4⁺ T cells. In one aspect, the present invention encompasses a peptide vaccine containing at least one conserved rhinovirus epitopes.

In one embodiment, the present invention provides a method for inducing an immune response against a rhinovirus (RV) comprising administering to the subject a pharmaceutical composition comprising an effective amount of at least one RV peptide epitope, wherein at least one of said RV peptide epitopes is a conserved RV peptide epitope recognized by antigen-experienced RV-specific CD4⁺ T cells.

In one embodiment, the present invention provides a method for activating antigen-experienced RV-specific CD4⁺ T cells in a subject comprising administering to the subject a pharmaceutical composition comprising an effective amount of at least one RV peptide epitope, wherein at least one of said RV peptide epitopes is a conserved RV peptide epitope recognized by antigen-experienced RV-specific CD4+ T cells.

In one aspect, the antigen-experienced RV-specific CD4⁺ T cells respond to cross-reactive determinants of different RV strains.

In one aspect, at least one RV peptide epitope is selected from the group consisting of SEQ ID NOs: 1-53, 56, and 57, and biologically active fragments and homologs of said at least one RV peptide epitope. One of ordinary skill in the art will appreciate that based on the teachings herein various combinations can be used as well as other conserved RV peptide epitopes recognized by the antigen-experienced RV-specific CD4⁺ T cells of the invention.

In one aspect, at least two RV peptide epitopes are administered. In another aspect, at least three RV peptide epitopes are administered. In a further aspect, at least five RV peptide epitopes are administered. In yet another aspect, at least ten RV peptide epitopes are administered.

In one aspect, an administered RV peptide epitope is selected from the group consisting of SEQ ID NOs:1-10.

In one embodiment, a composition of the invention further comprises an adjuvant.

In one aspect an RV peptide epitope is pan-specific.

In one aspect, when at least two RV peptide epitopes are administered, at least one RV-A16 VP1 epitope is administered to the subject.

In one aspect, at least one RV-A16 VP1 epitope is administered.

In one embodiment, the antigen-experienced RV-specific CD4⁺ T cells are cross-reactive with epitopes from different RV strains. In one aspect, the antigen-experienced RV-specific CD4⁺ T cells target a limited set of conserved RV peptide epitopes. In one aspect, the antigen-experienced RV-specific CD4⁺ T cells recognize a limited set of species-specific and pan-specific epitopes. In one aspect, the RV strains are selected from the group consisting of RV species A, B, and C.

In one embodiment, an RV peptide epitope administered to a subject an RV-A16 peptide epitope.

In one embodiment of the invention, antigen-experienced RV-specific CD4⁺ T cells recognize conserved RV epitopes that respond to cross-reactive determinants of different RV strains. In one aspect, the antigen-experienced RV-specific CD4⁺ T cells are epitope-specific T cells that are Th1-like and respond to RV infection.

In one aspect, the RV-A16-specific CD4+ T cells display a memory Th1 signature and respond rapidly to RV infection when contacted with an RV.

In one aspect, the RV is RV-A16 or RV-A39.

In one aspect, the method increases the number of CD4⁺ T cells that recognize conserved RV peptide epitopes. In one aspect, the RV peptide epitope comprises a VP1 or VP2 peptide epitope.

In one aspect of the invention, the RV peptide epitopes are highly conserved across RV species A.

In one aspect, administration of a composition of the invention activates CD8⁺ T cells.

In one embodiment, the present invention provides compositions and methods for predicting whether a subject will become infected upon exposure to a rhinovirus by identifying and measuring the number of CD4⁺ T cells in an uninfected subject that recognize a conserved epitope of at least one rhinovirus. In one aspect, the CD4⁺ T cells recognize a conserved epitope of two or more rhinoviruses. The information obtained can then be used to determine the type of treatment or prevention regimen to be used on the subject.

In one embodiment, the present invention provides a method for determining whether a subject has been exposed to a RV comprising a conserved RV peptide epitope. In one aspect, the method comprises administering to the subject a composition comprising at least one RV peptide epitope selected from the group consisting of SEQ ID NOs: 1-53, 56, and 57, and biologically active fragments and homologs thereof, and determining whether RV-specific CD4⁺ T cells display a memory Th1 phenotype, wherein an increase in the memory Th1 phenotype relative to a subject who has never been exposed to RV, is an indication that the subject has been previously exposed to an RV comprising a conserved RV peptide epitope.

In one aspect, the subject is seronegative for RV infection prior to the CD4+ T cells being contacted with said at least one RV peptide epitope.

The present invention also provides a method for determining whether a subject has circulating antigen-experienced RV-specific CD4⁺ T cells. In one aspect, the method comprises contacting CD4⁺ T cells from the subject with at least one RV peptide epitope selected from the group consisting of SEQ ID NOs: 1-53, 56, and 57, or biologically active fragments and homologs thereof, wherein an increase in the number of CD4⁺ T cells that are RV-specific is an indication that the subject has circulating antigen-experienced RV-specific CD4⁺ T cells. In one aspect, the RV peptide epitope is administered to the subject. In one aspect, a biological sample is obtained from the subject and the cells are contacted with the RV peptide epitope.

In one embodiment, a subject of the invention is seronegative for RV infection prior to CD4⁺ T cells being contacted with at least on RV peptide epitope. In one aspect, CD4⁺ T cells from the subject are contacted with each of SEQ ID NOs:1-10.

The present invention further provides a method for determining whether a subject will have a high rate of infection or a low rate of infection when exposed to a RV. In one aspect, the method comprises identifying and measuring circulating antigen-experienced RV-specific CD4+ T cells in the subject. A high number of circulating antigen-experienced RV-specific CD4+ T cells in the subject is an indication that the subject will have a low rate of infection when exposed to a RV. A low number of circulating antigen-experienced RV-specific CD4+ T cells in the subject is an indication that the subject will have a high rate of infection when exposed to a RV.

In one embodiment, the present invention provides a method for increasing resistance to an RV infection in a subject in need thereof. In one aspect, the method comprises administering to the subject a composition comprising a pharmaceutically-acceptable carrier, an adjuvant, and at least one RV peptide epitope selected from the group consisting of SEQ ID NOs: 1-58, and biologically active fragments and homologs thereof. In one aspect, the composition comprises at least one RV peptide epitope selected from the group consisting of SEQ ID NOs:1-10. In another aspect, the composition comprises each of SEQ ID NOs:1-10.

In one embodiment, the present invention provides compositions and methods useful for determining the time to shedding of rhinovirus by testing the relationship between virus-specific T cells and the time to virus shedding. This information is useful for planning a treatment regimen, for example, determining the type and duration of treatment to be administered.

In one embodiment, increasing the number of CD4+ T cells in a subject is useful for preventing or treating a rhinovirus infection. In one aspect, the number is increased by administering one or more peptide epitopes of the invention to a subject. In one aspect, the peptide epitope is an RV-16 peptide epitope. In one aspect, the peptide epitope is selected from the group consisting of SEQ ID NOs: 1-53 and biologically active fragments and homologs thereof. In one aspect, ten RV epitopes, three from VP1 and 7 from VP2, are disclosed to be targeted by high-frequency circulating RV-specific memory CD4+ T cells in healthy individuals. In one aspect, these peptides are useful for eliciting an immunogenic response. In one aspect, one of the peptides, or a biologically active fragment or homolog thereof can be used. In another aspect, at least two of the peptides can be used.

In one aspect, at least one peptide epitope selected from the group consisting of SEQ ID NOs:1, 2, 3, 4, 5, 6, 7, 8, 9, and 10 is administered to a subject. In another aspect, at least two peptide epitopes selected from the group consisting of SEQ ID NOs:1-10 is administered to a subject. In one each of 1, 2, 3, 4, 5, 6, 7, 8, 9, and 10 are administered to a subject. In another aspect, conserved epitopes from other rhinoviruses can be administered individually or in combination with RV-16 peptide epitopes. Useful RV-39 epitopes include, but are not limited to, peptides with amino acid sequences SEQ ID NOs:56 and 57.

In one embodiment, a biologically active fragment or homolog of at least one peptide epitope is administered to a subject.

In one embodiment, a vaccine of the invention can be used to induce CD4+ T cells that recognize conserved epitopes of rhinovirus or to increase the number of CD4+ T cells that recognized a conserved epitope of rhinovirus. A vaccine of the invention may comprise one or more peptides selected from the group consisting of SEQ ID NOs: 1-53, 56, and 57, and biologically active fragments and homologs thereof.

The present invention further includes the use of adjuvants and additional therapeutic agents as part of the treatment. For example, an additional therapeutic agent can include one or more immunomodulating agents discussed herein, a chemotherapeutic agent, or an antimicrobial agent such as an antimicrobial or an antiviral.

In one embodiment, the present invention provides compositions and methods for identifying, phenotyping, and tracking RV-specific CD4+ T cells.

In one embodiment, the present invention provides a comprehensive map of CD4+ T cell epitopes of capsid proteins VP1 and VP2 of RV-A16 and methods to prepare such a map. In one aspect, the map comprises SEQ ID NOs:1-10. In one aspect, the VP1 epitopes of RV-A16 map to the hydrophobic binding pocket. In one aspect, the RV peptide epitopes are highly conserved across RV species A. In one aspect, the map is prepared using tetramer-guided epitope mapping.

The present invention further provides a composition comprising a pharmaceutically-acceptable carrier, an adjuvant, and at least one RV peptide epitope selected from the group consisting of SEQ ID NOs: 1-58, and biologically active fragments and homologs thereof. In one aspect, the composition comprises at least one RV peptide epitope selected from the group consisting of SEQ ID NOs:1-10. In another aspect, the composition comprises each of SEQ ID NOs:1-10. In yet another aspect, the invention provides a composition comprising at least one RV peptide epitope selected from the group consisting of SEQ ID NOs:1-53, 56, and 57.

Sequences—

Some useful sequences of the invention include the following, as wells as active fragments and homologs thereof:

```
RV-A16 Epitopes
VP1_{P23}      PRFSLPFLSIASAYYMFYDG (SEQ ID NO:  1)
VP2_{P24}      PHQFINLRSNNSATLIVPYV (SEQ ID NO:  2)
VP2_{P21}      NEKQPSDDNWLNFDGTLLGN (SEQ ID NO:  3)
VP1_{P18}      HIVMQYMYVPPGAPIPTTRN (SEQ ID NO:  4)
VP2_{P3}       RGDSTITSQDVANAVVGYGV (SEQ ID NO:  5)
VP2_{P26}      VPYVNAVPMDSMVRHNNWSL (SEQ ID NO:  6)
VP2_{P2}       SDRIIQITRGDSTITSQDVA (SEQ ID NO:  7)
VP2_{P25}      SNNSATLIVPYVNAVPMDSM (SEQ ID NO:  8)
VP1_{P21}      QSGTNASVFWQHGQPFPRFS (SEQ ID NO:  9)
VP2_{P10}      TSKGWWWKLPDALKDMGIFG (SEQ ID NO: 10)
VP1_{P20}      TTRNDYAWQSGTNASVFWQH (SEQ ID NO: 11)
VP2_{P12}      GIFGENMFYHFLGRSGYTVH (SEQ ID NO: 12)
VP2_{P22}      NWLNFDGTLLGNLLIFPHQF (SEQ ID NO: 13)
VP2_{P23}      LLGNLLIFPHQFINLRSNNS (SEQ ID NO: 14)
VP1_{P14}      QIRRKFEMFTYARFDSEITM (SEQ ID NO: 15)
VP1_{P17}      AAKDGHIGHIVMQYMYVPPG (SEQ ID NO: 16)
VP2_{P8}       TSSNRFYTLDSKMWNSTSKG (SEQ ID NO: 17)
```

-continued

| | | |
|---|---|---|
| VP2$_{P15}$ | ASKFHQGTLLVVMIPEHQLA | (SEQ ID NO: 18) |
| VP1$_{P15}$ | FTYARFDSEITMVPSVAAKD | (SEQ ID NO: 19) |
| VP1$_{P16}$ | EITMVPSVAAKDGHIGHIVM | (SEQ ID NO: 20) |
| VP1$_{P27}$ | VVTNDMGTLCSRIVTSEQLH | (SEQ ID NO: 21) |
| VP1$_{P32}$ | RPPRAVQYSHTHTTNYKLSS | (SEQ ID NO: 22) |
| VP1$_{P29}$ | EQLHKVKVVTRIYHKAKHTK | (SEQ ID NO: 23) |
| VP2$_{P1}$ | PSVEACGYSDRIIQITRGDS | (SEQ ID NO: 24) |
| VP2$_{P9}$ | LDSKMWNSTSKGWWWKLPDA | (SEQ ID NO: 25) |
| VP1$_{P24}$ | SIASAYYMFYDGYDGDTYKS | (SEQ ID NO: 26) |
| VP2$_{P15}$ | ASKFHQGTLLVVMIPEHQLA | (SEQ ID NO: 27) |
| VP2$_{P16}$ | LLVVMIPEHQLATVNKGNVN | (SEQ ID NO: 28) |
| VP2$_{P30}$ | ISNIVPITVSISPMCAEFSG | (SEQ ID NO: 29) |
| VP2$_{P31}$ | ITVSISPMCAEFSGARAKTV | (SEQ ID NO: 30) |
| VP1$_{P22}$ | FWQHGQPFPRFSLPFLSIAS | (SEQ ID NO: 31) |

PHQFINLRSNNS (SEQ ID NO: 32)

NWLNFDGTLLGN (SEQ ID NO: 33)

HIVMQYMYVPPG (SEQ ID NO: 34)

SDRIIQITRGDS (SEQ ID NO: 35)

FWQHGQPFPRFS (SEQ ID NO: 36)

FLSIASAYY (SEQ ID NO: 37)

FINLRSNNS (SEQ ID NO: 38)

LNFDGTLLG (SEQ ID NO: 39)

MQYMYVPPG (SEQ ID NO: 40)

ITSQDVANA (SEQ ID NO: 41)

AVPMDSMVR (SEQ ID NO: 42)

IIQITRGDS (SEQ ID NO: 43)

IVPYVNAVP (SEQ ID NO: 44)

WQHGQPFPR (SEQ ID NO: 45)

WWKLPDALK (SEQ ID NO: 46)

HIVMQYMYV (SEQ ID NO: 47)

TITSQDVAN (SEQ ID NO: 48)

MVRHNNWSL (SEQ ID NO: 49)

LIVPYNAV (SEQ ID NO: 50)

RFSLPFLSI (SEQ ID NO: 51)

LRSNNSATL (SEQ ID NO: 52)

IVPYNAVP (SEQ ID NO: 53)

RV-A16 VP1 (SEQ ID NO: 54)
PITQNPVERYVDEVLNEVLVVPNINQSHPTTSNAAPVLDAAETGHTNKI
QPEDTIETRYVQSSQTLDEMSVESFLGRSGCIHESVLDIVDNYNDQSFT
KWNINLQEMAQIRRKFEMFTYARFDSEITMVPSVAAKDGHIGHIVMQYM
YVPPGAPIPTTRDDYAWQSGTNASVFWQHGQPFPRFSLPFLSIASAYYM
FYDGYDGDTYKSRYGTVVTNDMGTLCSRIVTSEQLHKVKVVTRIYHKAK
HTKAWCPRPPRAVQYSHTHTTNYKLSSEVHNDVAIRPRTNLTTV

RV-A16 VP2 (SEQ ID NO: 55)
SPSVEACGYSDRIIQITRGDSTITSQDVANAVVGYGVWPHYLTPQDATA
IDKPTQPDTSSNRFYTLDSKMWNSTSKGWWWKLPDALKDMGIFGENMFY
HFLGRSGYTVHVQCNASKFHQGTLLVVMIPEHQLATVNKGNVNAGYKYT
HPGEAGREVGTQVENEKQPSDDNWLNFDGTLLGNLLIFPHQFINLRSNN
SATLIVPYVNAVPMDSMVRHNNWSLVIIPVCQLQSNNISNIVPITVSIS
PMCAEFSGARAKTVVQ

RV-A39 Epitopes
VP1$_{105-124}$ AQVRRKFEMFTYVRFDSEIT (SEQ ID NO: 56)

VP2$_{169-188}$ SDDNWLNFDGTLLGNLLIFP (SEQ ID NO: 57)

RV-C2
GGSVIKYFNINYYKDSASSGLTKQDFSQDPSKFTQPIADVLTNPALMSP
TVEACGFSDRLKQITIGNSTITTQDSLNTIVAYGEWPEYLSDLDATSVD
KPTHPETSSDRFYTLESVMWHGSSRGWWWK1PDCLKDMGMFGQNMYHHS
MGRSGMLIHVQCNATKFHSGCLLVVVVPEHQLAYIGAGGVNVKYEHTHP
GERGHTLQASDVRSNHNPDEDPFYLCNGTLLGNALIYPHQMINLRTNNS
ATIVVPYINCVPMDNMLRHNNVSLLIIPIVPLKANTDAVNSLPITVTIA
PDKSEFSGAMKSQQQGLPTRSPAGSQQFMTTEDEQSPNILPEYSPTKMI
HIPGRIDNILHIAMVESLIPLNNIPGQVGTVGMYNVTIASKTADQDMIL
AIPLQMDNTLFATTLVGEILNYFSNWSGSIRVTCICVCDSFSTGKFLMA
YTPPGGGLPTTRKEAMLGVHVVWDLGLQSSCTLVAPWMSSTFYRRTKGS
NYTSGGYITLWYQTNFVATTTGGTGTIIATCSACPDLSVRMMRDTPMIK
QPENNIQNPVDNFVDEVLKEVLVVPDTKPSGPTHTVKPTVLNAMEIGVT
PDATPESVIETRYVINNHTNNEALMENFLGRSSLWAELQMSDGFKKWDI
NFQEQAHIRKKIEMFTY1RFDMEVTIVTNNQGLMQIMYVPPGIEAPESL
NDKRWNGASNPSVFYQPKSGFPRFTIPFTGLGSAYYVFYDG
(SEQ ID NO:58)

Various aspects and embodiments of the invention are described in further detail below.

BRIEF DESCRIPTION OF THE DRAWINGS

FIG. 3 (A-C). HLA Class I and II Binding "Hotspots" Localize to Conserved Regions of VP1 and VP2. Epitope binding to HLA class I and II supertypes was analyzed for RV-A16 VP1 and VP2 using MULTIPRED2. The percentage binding is shown for each supertype corresponding to: (A) common class II supertypes that include molecules used in TGEM studies, (B) less common class II DRB1 supertypes, and (C) the major class I supertypes, HLA-A, -B, and -C. Analysis of DRB5 supertypes was not available.

Figure 1:
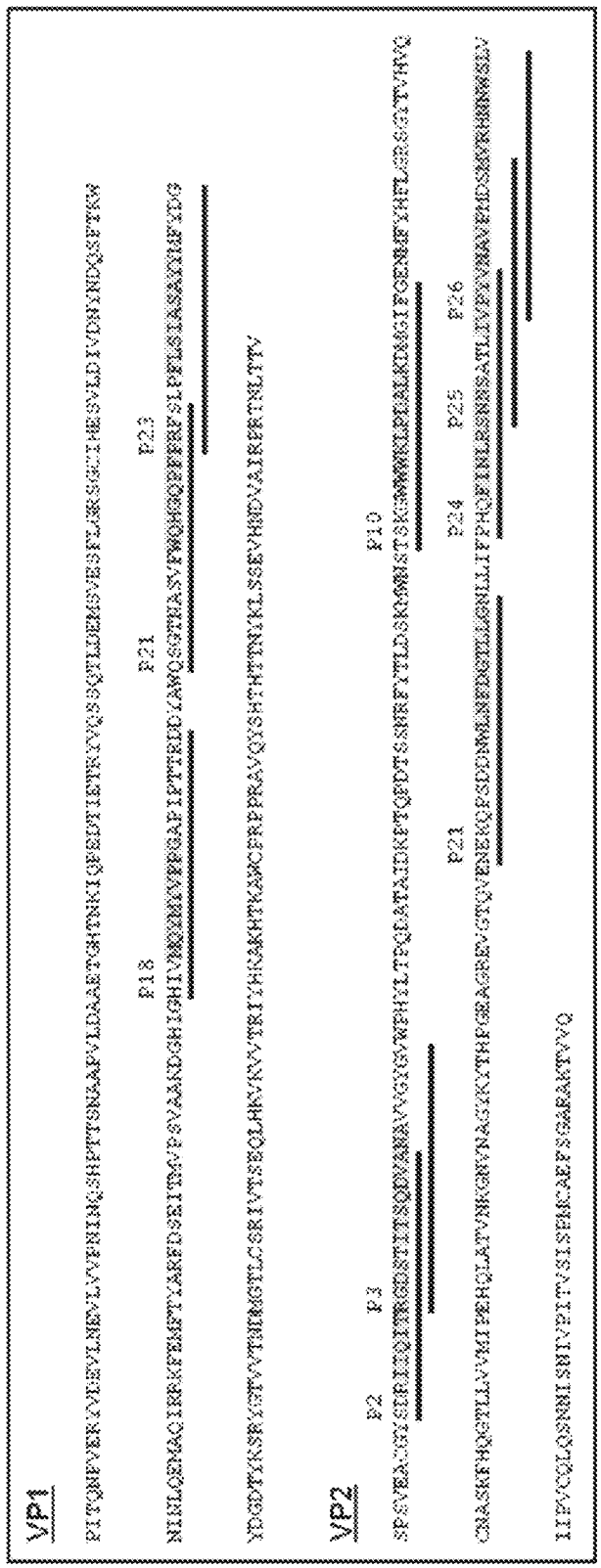
FIG. 1. Localization of VP1 and VP2 Epitopes of RV-A16. Underline denotes full length peptides and grey highlights denote predicted core epitopes.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. Therefore, about 50% means in the range of 45%-55%.

A disease or disorder is "alleviated" if the severity of a symptom of the disease, condition, or disorder, or the frequency with which such a symptom is experienced by a subject, or both, are reduced.

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As used herein, the term "adjuvant" refers to a substance that elicits an enhanced immune response when used in combination with a specific antigen.

As use herein, the terms "administration of" and or "administering" a compound should be understood to mean providing a compound of the invention or a prodrug of a compound of the invention to a subject in need of treatment.

As used herein, the term "aerosol" refers to suspension in the air. In particular, aerosol refers to the particlization or atomization of a formulation of the invention and its suspension in the air.

As used herein, an "agonist" is a composition of matter which, when administered to a mammal such as a human, enhances or extends a biological activity attributable to the level or presence of a target compound or molecule of interest in the mammal.

The term "antagomir" refers to a small RNA or DNA (or chimeric) molecule to antagonize endogenous small RNA regulators like microRNA (miRNA). These antagonists bear complementary nucleotide sequences for the most part, which means that antagomirs should hybridize to the mature microRNA (miRNA). They prevent other molecules from binding to a desired site on an mRNA molecule and are used to silence endogenous microRNA (miR). Antagomirs are therefore designed to block biological activity of these post-transcriptional molecular switches. Like the preferred target ligands (microRNA, miRNA), antagomirs have to cross membranes to enter a cell. Antagomirs also known as anti-miRs or blockmirs.

An "antagonist" is a composition of matter which when administered to a mammal such as a human, inhibits a biological activity attributable to the level or presence of a compound or molecule of interest in the mammal.

As used herein, an "analog" of a chemical compound is a compound that, by way of example, resembles another in structure but is not necessarily an isomer (e.g., 5-fluorouracil is an analog of thymine).

As used herein, "amino acids" are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

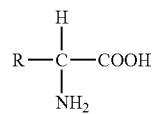

Amino acids may be classified into seven groups on the basis of the side chain R: (1) aliphatic side chains; (2) side chains containing a hydroxylic (OH) group; (3) side chains containing sulfur atoms; (4) side chains containing an acidic or amide group; (5) side chains containing a basic group; (6) side chains containing an aromatic ring; and (7) proline, an imino acid in which the side chain is fused to the amino group.

Synthetic or non-naturally occurring amino acids refer to amino acids which do not naturally occur in vivo but which, nevertheless, can be incorporated into the peptide structures described herein. The resulting "synthetic peptide" contain amino acids other than the 20 naturally occurring, genetically encoded amino acids at one, two, or more positions of the peptides. For instance, naphthylalanine can be substituted for tryptophan to facilitate synthesis. Other synthetic amino acids that can be substituted into peptides include L-hydroxypropyl, L-3,4-dihydroxyphenylalanyl, alpha-amino acids such as L-alpha-hydroxylysyl and D-alpha-methylalanyl, L-alpha.-methylalanyl, beta.-amino acids, and isoquinolyl. D amino acids and non-naturally occurring synthetic amino acids can also be incorporated into the peptides. Other derivatives include replacement of the naturally occurring side chains of the 20 genetically encoded amino acids (or any L or D amino acid) with other side chains.

As used herein, the term "conservative amino acid substitution" is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid, as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

An "antagonist" is a composition of matter which when administered to a mammal such as a human, inhibits a biological activity attributable to the level or presence of a compound or molecule of interest in the mammal.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antigenic determinant" as used herein refers to that portion of an antigen that makes contact with a particular antibody (i.e., an epitope). When a protein or fragment of a protein, or chemical moiety is used to immunize a host animal, numerous regions of the antigen may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

The term "aqueous solution" as used herein can include other ingredients commonly used, such as sodium bicarbonate described herein, and further includes any acid or base solution used to adjust the pH of the aqueous solution while solubilizing a peptide.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The term "biocompatible", as used herein, refers to a material that does not elicit a substantial detrimental response in the host.

As used herein, the term "biologically active fragments" or "bioactive fragment" of the peptides encompasses natural or synthetic portions of a longer peptide or protein that are capable of specific binding to their natural ligand or of performing the desired function of the protein, for example, a fragment of a protein of larger peptide which still contains the epitope of interest and is immunogenic. The same is true for biologically active homologs.

The term "biological sample," as used herein, refers to samples obtained from a subject, including, but not limited to, skin, hair, tissue, blood, plasma, cells, sweat and urine.

As used herein, the term "carrier molecule" refers to any molecule that is chemically conjugated to the antigen of interest that enables an immune response resulting in antibodies specific to the native antigen.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A "compound," as used herein, refers to any type of substance or agent that is commonly considered a drug, or a candidate for use as a drug, as well as combinations and mixtures of the above.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell is a cell being examined.

A "pathoindicative" cell is a cell which, when present in a tissue, is an indication that the animal in which the tissue is located (or from which the tissue was obtained) is afflicted with a disease or disorder.

A "pathogenic" cell is a cell which, when present in a tissue, causes or contributes to a disease or disorder in the animal in which the tissue is located (or from which the tissue was obtained).

A tissue "normally comprises" a cell if one or more of the cell are present in the tissue in an animal not afflicted with a disease or disorder.

As used herein, a "derivative" of a compound refers to a chemical compound that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "enhancer" is a DNA regulatory element that can increase the efficiency of transcription, regardless of the distance or orientation of the enhancer relative to the start site of transcription.

The term "epitope" as used herein is defined as small chemical groups or molecular region on the antigen molecule that can elicit and react with an antibody or antigen receptor on a T cell. An antigen can have one or more epitopes. Most antigens have many epitopes; i.e., they are multivalent. One skilled in the art understands that generally the overall three-dimensional structure, rather than the specific linear sequence of the molecule, is the main criterion of antigenic specificity.

A "fragment" or "segment" is a portion of an amino acid sequence, comprising at least one amino acid, or a portion of a nucleic acid sequence comprising at least one nucleotide.

The terms "fragment" and "segment" are used interchangeably herein.

As used herein, a "functional" biological molecule is a biological molecule in a form in which it exhibits a property by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

By the term "immunizing a subject against an antigen" is meant administering to the subject a composition, a protein complex, a DNA encoding a protein complex, an antibody or a DNA encoding an antibody, which elicits an immune response in the subject, and, for example, provides protection to the subject against a disease caused by the antigen or which prevents the function of an antigen.

The term "immunologically active fragments thereof" will generally be understood in the art to refer to a fragment of a polypeptide antigen comprising at least an epitope, which means that the fragment at least comprises 4 contiguous amino acids from the sequence of the polypeptide antigen.

As used herein, the term "induction of apoptosis" means a process by which a cell is affected in such a way that it begins the process of programmed cell death, which is characterized by the fragmentation of the cell into membrane-bound particles that are subsequently eliminated by the process of phagocytosis.

As used herein, the term "inhaler" refers both to devices for nasal and pulmonary administration of a drug, e.g., in solution, powder and the like. For example, the term "inhaler" is intended to encompass a propellant driven inhaler, such as is used to administer antihistamine for acute asthma attacks, and plastic spray bottles, such as are used to administer decongestants.

The term "inhibit," as used herein when referring to a function, refers to the ability of a compound of the invention to reduce or impede a described function. Preferably, inhibition is by at least 10%, more preferably by at least 25%, even more preferably by at least 50%, and most preferably, the function is inhibited by at least 75%. When the term "inhibit" is used more generally, such as "inhibit Factor I", it refers to inhibiting expression, levels, and activity of Factor I.

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

As used herein "injecting, or applying, or administering" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

A "synergistic" effect means that the result is greater than an additive effect.

As used herein, a "ligand" is a compound that specifically binds to a target compound or molecule. A ligand "specifically binds to" or "is specifically reactive with" a compound when the ligand functions in a binding reaction which is determinative of the presence of the compound in a sample of heterogeneous compounds.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides.

The term "per application" as used herein refers to administration of a drug or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Pharmaceutically acceptable" means physiologically tolerable, for either human or veterinary application.

As used herein, "pharmaceutical compositions" include formulations for human and veterinary use.

"Plurality" means at least two.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

By "presensitization" is meant pre-administration of at least one innate immune system stimulator prior to challenge with an agent. This is sometimes referred to as induction of tolerance.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

A "prophylactic" treatment is a treatment administered to a subject who does not exhibit signs of a disease or exhibits only early signs of the disease for the purpose of decreasing the risk of developing pathology associated with the disease.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides, vol.* 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

A "recombinant polypeptide" is one which is produced upon expression of a recombinant polynucleotide.

The term "regulate" refers to either stimulating or inhibiting a function or activity of interest.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, a "subject in need thereof" is a patient, animal, mammal, or human, who will benefit from the method of this invention.

As used herein, a "substantially homologous amino acid sequences" includes those amino acid sequences which have at least about 95% homology, preferably at least about 96% homology, more preferably at least about 97% homology, even more preferably at least about 98% homology, and most preferably at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term to "treat," as used herein, means reducing the frequency with which symptoms are experienced by a patient or subject or administering an agent or compound to reduce the frequency with which symptoms are experienced.

A "prophylactic" treatment is a treatment administered to a subject who does not exhibit signs of a disease or exhibits only early signs of the disease for the purpose of decreasing the risk of developing pathology associated with the disease.

By the term "vaccine," as used herein, is meant a composition which when inoculated into a subject has the effect of stimulating an immune response in the subject, which serves to fully or partially protect the subject against a condition, disease or its symptoms. In one aspect, the condition is a rhinovirus infection. The term vaccine can encompass prophylactic as well as therapeutic vaccines. A combination vaccine is one which combines two or more vaccines, or two or more compounds or agents.

Embodiments

In one embodiment, the present invention provides compositions and methods for identifying, phenotyping, and tracking RV-specific CD4+ T cells.

In one embodiment, the present invention provides peptides useful for eliciting an immune response in a subject. In one aspect, one of the peptides, or a biologically active fragment or homolog thereof can be used. In another aspect, at least two of the peptides can be used.

In one embodiment, the present invention provides peptides useful for vaccines against RV infection. In one aspect, one peptide is administered to a subject. In another aspect, more than one peptide is administered to a subject.

The present application discloses conserved RV epitopes targeted by high-frequency circulating RV-specific memory Th1 cells. That is, it is disclosed herein that circulating memory CD4+ T cells present in healthy individuals recognize a limited set of peptides derived from RV-A16 capsid proteins that are highly conserved across different RV strains, supports the immunogenic potential of these RV peptides.

In one aspect, ten RV epitopes, three from VP1 and 7 from VP2, are disclosed to be targeted by high-frequency circulating RV-specific memory $CD4^+$ T cells in healthy individuals. In one aspect, these peptides are useful for eliciting an immunogenic response.

The peptides of the present invention may be readily prepared by standard, well-established techniques, such as solid-phase peptide synthesis (SPPS) as described by Stewart et al. in *Solid Phase Peptide Synthesis*, 2nd Edition, 1984, Pierce Chemical Company, Rockford, Ill.; and as described by Bodanszky and Bodanszky in *The Practice of Peptide Synthesis*, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions that will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method that utilized tert-butyloxcarbonyl as the α-amino protecting group, and the FMOC method which utilizes 9-fluorenylmethyloxcarbonyl to protect the α-amino of the amino acid residues, both methods of which are well-known by those of skill in the art.

To ensure that the proteins or peptides obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide can be purified to remove contaminants. In this regard, it will be appreciated that the peptide will be purified to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure peptide obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

The invention further encompasses the use of aptamers. In one embodiment, an aptamer is a compound that is selected in vitro to bind preferentially to another compound (in this case the identified proteins). In one aspect, aptamers are nucleic acids or peptides, because random sequences can be readily generated from nucleotides or amino acids (both naturally occurring or synthetically made) in large numbers but of course they need not be limited to these. In another aspect, the nucleic acid aptamers are short strands of DNA that bind protein targets. In one aspect, the aptamers are oligonucleotide aptamers. Oligonucleotide aptamers are oligonucleotides which can bind to a specific protein sequence of interest. A general method of identifying aptamers is to start with partially degenerate oligonucleotides, and then simultaneously screen the many thousands of oligonucleotides for the ability to bind to a desired protein. The bound oligonucleotide can be eluted from the protein and sequenced to identify the specific recognition sequence. Transfer of large amounts of a chemically stabilized aptamer into cells can result in specific binding to a polypeptide of interest, thereby blocking its function. [For example, see the following publications describing in vitro selection of aptamers: Klug et al., Mol. Biol. Reports 20:97-107 (1994); Wallis et al., Chem. Biol. 2:543-552 (1995); Ellington, Curr. Biol. 4:427-429 (1994); Lato et al., Chem. Biol. 2:291-303 (1995); Conrad et al., Mol. Div. 1:69-78 (1995); and Uphoff et al., Curr. Opin. Struct. Biol. 6:281-287 (1996)]. Aptamers offer advantages over other oligonucleotide-based approaches that artificially interfere with target gene function due to their ability to bind protein products of these genes with high affinity and specificity. However, RNA aptamers can be limited in their ability to target intracellular proteins since even nuclease-resistant aptamers do not efficiently enter the intracellular compartments. Moreover, attempts at expressing RNA aptamers within mammalian cells through vector-based approaches have been hampered by the presence of additional flanking sequences in expressed RNA aptamers, which may alter their functional conformation.

The idea of using single-stranded nucleic acids (DNA and RNA aptamers) to target protein molecules is based on the ability of short sequences (20 mers to 80 mers) to fold into unique 3D conformations that enable them to bind targeted proteins with high affinity and specificity. RNA aptamers have been expressed successfully inside eukaryotic cells, such as yeast and multicellular organisms, and have been shown to have inhibitory effects on their targeted proteins in the cellular environment.

This invention encompasses methods of screening compounds to identify those compounds that act as agonists (stimulate) or antagonists (inhibit) of the protein interactions and pathways described herein. Screening assays for antagonist compound candidates are designed to identify compounds that bind or complex with the peptides described herein, or otherwise interfere with the interaction of the peptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, high-throughput assays, immunoassays, and cell-based assays, which are well characterized in the art.

All assays for antagonists are common in that they call for contacting the compound or drug candidate with a peptide identified herein under conditions and for a time sufficient to allow these two components to interact.

In binding assays, the interaction is binding and the complex formed can be isolated or detected in the reaction mixture. In a particular embodiment, one of the peptides of the complexes described herein, or the test compound or drug candidate is immobilized on a solid phase, e.g., on a microtiter plate, by covalent or non-covalent attachments. Non-covalent attachment generally is accomplished by coating the solid surface with a solution of the peptide and drying. Alternatively, an immobilized antibody, e.g., a monoclonal antibody, specific for the peptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with, but does not bind to a particular peptide identified herein, its interaction with that peptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, Nature (London), 340:245-246 (1989); Chien et al., Proc. Natl. Acad. Sci. USA, 88:9578-9582 (1991)) as disclosed by Chevray and Nathans, Proc. Natl. Acad. Sci. USA, 89: 5789-5793 (1991). Complete kits for identifying protein-protein interactions between two specific proteins using the two-hybrid technique are available. This system can also be extended to map protein domains involved in specific protein interactions as well as to pinpoint amino acid residues that are crucial for these interactions.

Compounds that interfere with the interaction of a peptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

Other assays and libraries are encompassed within the invention, such as the use of Phylomers® and reverse yeast two-hybrid assays (see Watt, 2006, Nature Biotechnology, 24:177; Watt, U.S. Pat. No. 6,994,982; Watt, U.S. Pat. Pub. No. 2005/0287580; Watt, U.S. Pat. No. 6,510,495; Barr et al., 2004, J. Biol. Chem., 279:41:43178-43189; the contents of each of these publications is hereby incorporated by reference herein in their entirety). Phylomers® are derived from sub domains of natural proteins, which makes them potentially more stable than conventional short random peptides. Phylomers® are sourced from biological genomes that are not human in origin. This feature significantly enhances the potency associated with Phylomers® against human protein targets. Phylogica's current Phylomer® library has a complexity of 50 million clones, which is comparable with the numerical complexity of random peptide or antibody Fab fragment libraries. An Interacting Peptide Library, consisting of 63 million peptides fused to the B42 activation domain, can be used to isolate peptides capable of binding to a target protein in a forward yeast two hybrid screen. The second is a Blocking Peptide Library made up of over 2 million peptides that can be used to screen for peptides capable of disrupting a specific protein interaction using the reverse two-hybrid system.

The Phylomer® library consists of protein fragments, which have been sourced from a diverse range of bacterial genomes. The libraries are highly enriched for stable subdomains (15-50 amino acids long). This technology can be integrated with high throughput screening techniques such as phage display and reverse yeast two-hybrid traps.

The present application discloses compositions and methods for regulating the proteins described herein, and those not disclosed which are known in the art are encompassed within the invention. For example, various modulators/effectors are known, e.g. antibodies, biologically active nucleic acids, such as antisense molecules, RNAi molecules, or ribozymes, aptamers, peptides or low-molecular weight organic compounds recognizing said polynucleotides or polypeptides.

The present invention also provides nucleic acids encoding peptides, proteins, and antibodies of the invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

It is not intended that the present invention be limited by the nature of the nucleic acid employed. The target nucleic acid may be native or synthesized nucleic acid. The nucleic acid may be from a viral, bacterial, animal or plant source. The nucleic acid may be DNA or RNA and may exist in a double-stranded, single-stranded or partially double-stranded form. Furthermore, the nucleic acid may be found as part of a virus or other macromolecule. See, e.g., Fasbender et al., 1996, J. Biol. Chem. 272:6479-89 (polylysine condensation of DNA in the form of adenovirus).

In some circumstances, as where increased nuclease stability is desired, nucleic acids having modified internucleoside linkages may be preferred. Nucleic acids containing modified internucleoside linkages may also be synthesized using reagents and methods that are well known in the art. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide (—CH2-S—CH2), diinethylene-sulfoxide (—CH2-SO—CH2), dimethylene-sulfone (—CH2-SO2-CH2), 2'-O-alkyl, and 2'-deoxy2'-fluoro phosphorothioate internucleoside linkages are well known in the art (see Uhlmann et al., 1990, Chem. Rev. 90:543-584; Schneider et al., 1990, Tetrahedron Lett. 31:335 and references cited therein).

The nucleic acids may be purified by any suitable means, as are well known in the art. For example, the nucleic: acids can be purified by reverse phase or ion exchange HPLC, size exclusion chromatography or gel electrophoresis. Of course, the skilled artisan will recognize that the method of purification will depend in part on the size of the DNA to be purified. The term nucleic acid also specifically includes nucleic acids composed of bases other than the five biologically occurring bases (adenine, guanine, thymine, cytosine and uracil).

The present invention also encompasses pharmaceutical and therapeutic compositions comprising the compounds of the present invention.

The present invention is also directed to pharmaceutical compositions comprising the compounds of the present invention. More particularly, such compounds can be formulated as pharmaceutical compositions using standard pharmaceutically acceptable carriers, fillers, solubilizing agents and stabilizers known to those skilled in the art.

When used in vivo for therapy, the antibodies of the invention are administered to the subject in therapeutically effective amounts (i.e., amounts that have a desired therapeutic effect). In one aspect, they will be administered parenterally.

The present invention is also directed to pharmaceutical compositions comprising the compounds of the present invention. More particularly, such compounds can be formulated as pharmaceutical compositions using standard pharmaceutically acceptable carriers, fillers, solubilizing agents and stabilizers known to those skilled in the art.

In accordance with one embodiment, a method of treating a subject in need of treatment is provided. The method comprises administering a pharmaceutical composition comprising at least one compound of the present invention to a subject in need thereof. Compounds identified by the methods of the invention can be administered with known compounds or other medications as well.

The invention also encompasses the use of pharmaceutical compositions of an appropriate compound, and homologs, fragments, analogs, or derivatives thereof to practice the methods of the invention, the composition comprising at least one appropriate compound, and homolog, fragment, analog, or derivative thereof and a pharmaceutically-acceptable carrier.

The pharmaceutical compositions useful for practicing the invention may be administered to deliver a dose of between 1 ng/kg/day and 100 mg/kg/day.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

It will be understood by the skilled artisan that such pharmaceutical compositions are generally suitable for administration to animals of all sorts. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys. The invention is also contemplated for use in contraception for nuisance animals such as rodents.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically, dosages of the compound of the invention which may be administered to an animal, preferably a human, range in amount from 1 μg to about 100 g per kilogram of body weight of the subject. While the precise dosage administered will vary depending upon any number of factors, including, but not limited to, the type of animal and type of disease state being treated, the age of the subject and the route of administration. In one aspect, the dosage of the compound will vary from about 1 mg to about 10 g per kilogram of body weight of the subject. In another aspect, the dosage will vary from about 10 mg to about 1 g per kilogram of body weight of the subject.

The compound may be administered to a subject as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the condition or disease being treated, the type and age of the subject, etc.

The invention is also directed to methods of administering the compounds of the invention to a subject. In one embodiment, the invention provides a method of treating a subject by administering compounds identified using the methods of the invention. Pharmaceutical compositions comprising the present compounds are administered to an individual in need thereof by any number of routes including, but not limited to, topical, oral, intravenous, intramuscular, intra arterial, intramedullary, intrathecal, intraventricular, transdermal, subcutaneous, intraperitoneal, intranasal, enteral, topical, sublingual, or rectal means.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate, and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The invention also includes a kit comprising the composition of the invention and an instructional material which describes adventitially administering the composition to a cell or a tissue of a mammal. In another embodiment, this kit comprises a (preferably sterile) solvent suitable for dissolving or suspending the composition of the invention prior to administering the compound to the mammal.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container which contains the peptide of the invention or be shipped together with a container which contains the peptide. Alternatively, the instructional material may be shipped separately from the container with the intention that the instructional material and the compound be used cooperatively by the recipient.

Other techniques known in the art may be used in the practice of the present invention, including those described in international patent application WO 2006/091535 (PCT/US2006/005970), the entirety of which is incorporated by reference herein.

It will be appreciated, of course, that the proteins or peptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring or non-standard synthetic amino acids. The peptides of the invention are not limited to products of any of the specific exemplary processes listed herein.

The invention includes the use of beta-alanine (also referred to as β-alanine, β-Ala, bA, and βA, having the structure:

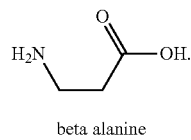

beta alanine

Sequences are provided herein which use the symbol "PA", but in the Sequence Listing submitted herewith "PA" is provided as "Xaa" and reference in the text of the Sequence Listing indicates that Xaa is beta alanine.

Peptides useful in the present invention, such as standards, or modifications for analysis, may be readily prepared by standard, well-established techniques, such as solid-phase peptide synthesis (SPPS) as described by Stewart et al. in *Solid Phase Peptide Synthesis,* 2nd Edition, 1984, Pierce Chemical Company, Rockford, Ill.; and as described by Bodanszky and Bodanszky in *The Practice of Peptide Synthesis,* 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well-known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide may be purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high performance liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

As discussed, modifications or optimizations of peptide ligands of the invention are within the scope of the application. Modified or optimized peptides are included within the definition of peptide binding ligand. Specifically, a peptide sequence identified can be modified to optimize its potency, pharmacokinetic behavior, stability and/or other biological, physical and chemical properties.

Amino Acid Substitutions

In certain embodiments, the disclosed methods and compositions may involve preparing peptides with one or more substituted amino acid residues. In various embodiments, the structural, physical and/or therapeutic characteristics of peptide sequences may be optimized by replacing one or more amino acid residues.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art. For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2',-3',- or 4'-methyl-2, 3 or 4-biphenylalanine, and 2- or 3-pyridylalanine.

Substitution of amino acids containing basic functions: including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids can include various hydropathic indices. In one aspect, the hydropathic indices are within +/−2, in another they are within +/−1, and in one aspect, they are within +/−0.5.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4) In one aspect, the replacement of amino acids with others of similar hydrophilicity is provided by the invention.

Other considerations include the size of the amino acid side chain. For example, it would generally not be preferable to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL Rockefeller University website). For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.) In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

In other embodiments, therapeutic agents, including, but not limited to, cytotoxic agents, anti-angiogenic agents, pro-apoptotic agents, antibiotics, hormones, hormone antagonists, chemokines, drugs, prodrugs, toxins, enzymes or other agents may be used as adjunct therapies when using the antibody/peptide ligand complexes described herein.

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

The invention further provides cells transfected with the nucleic acid containing an enhancer/promoter combination of the invention.

Promoters may be coupled with other regulatory sequences/elements which, when bound to appropriate intracellular regulatory factors, enhance ("enhancers") or repress ("repressors") promoter-dependent transcription. A promoter, enhancer, or repressor, is said to be "operably linked" to a transgene when such element(s) control(s) or affect(s) transgene transcription rate or efficiency. For example, a promoter sequence located proximally to the 5' end of a transgene coding sequence is usually operably linked with the transgene. As used herein, term "regulatory elements" is used interchangeably with "regulatory sequences" and refers to promoters, enhancers, and other expression control elements, or any combination of such elements.

Promoters are positioned 5' (upstream) to the genes that they control. Many eukaryotic promoters contain two types of recognition sequences: TATA box and the upstream promoter elements. The TATA box, located 25-30 bp upstream of the transcription initiation site, is thought to be involved in directing RNA polymerase II to begin RNA synthesis as the correct site. In contrast, the upstream promoter elements determine the rate at which transcription is initiated. These elements can act regardless of their orientation, but they must be located within 100 to 200 bp upstream of the TATA box.

Enhancer elements can stimulate transcription up to 1000-fold from linked homologous or heterologous promoters. Enhancer elements often remain active even if their orientation is reversed (Li et al., J. Bio. Chem. 1990, 266: 6562-6570). Furthermore, unlike promoter elements, enhancers can be active when placed downstream from the transcription initiation site, e.g., within an intron, or even at a considerable distance from the promoter (Yutzey et al., Mol. and Cell. Bio. 1989, 9:1397-1405).

It is known in the art that some variation in this distance can be accommodated without loss of promoter function. Similarly, the positioning of regulatory elements with respect to the transgene may vary significantly without loss of function. Multiple copies of regulatory elements can act in concert. Typically, an expression vector comprises one or more enhancer sequences followed by, in the 5' to 3' direction, a promoter sequence, all operably linked to a transgene followed by a polyadenylation sequence.

The present invention further relies on the fact that many enhancers of cellular genes work exclusively in a particular tissue or cell type. In addition, some enhancers become active only under specific conditions that are generated by the presence of an inducer such as a hormone or metal ion. Because of these differences in the specificities of cellular enhancers, the choice of promoter and enhancer elements to be incorporated into a eukaryotic expression vector is determined by the cell type(s) in which the recombinant gene is to be expressed.

In one aspect, the regulatory elements of the invention may be heterologous with regard to each other or to a transgene, that is, they may be from different species. Furthermore, they may be from species other than the host, or they also may be derived from the same species but from different genes, or they may be derived from a single gene.

Additional types of compounds can be administered to treat further the addiction-related diseases and disorders or to treat other diseases and disorders. The additional types of compounds include, but are not limited to, adrenergics, adrenocortical steroids, adrenocortical suppressants, aldosterone antagonists, amino acids, analeptics, analgesics, anorectic compounds, anorexics, anti-anxiety agents, antidepressants, antihypertensives, anti-inflammatories, antinauseants, antineutropenics, antiobsessional agents, antiparkinsonians, antipsychotics, appetite suppressants, blood glucose regulators, carbonic anhydrase inhibitors, cardiotonics, cardiovascular agents, choleretics, cholinergics, cholinergic agonists, cholinesterase deactivators, cognition adjuvants, cognition enhancers, hormones, memory adjuvants, mental performance enhancers, mood regulators, neuroleptics, neuroprotectives, psychotropics, relaxants, sedative-hypnotics, stimulants, thyroid hormones, thyroid inhibitors, thyromimetics, cerebral ischemia agents, vasoconstrictors, and vasodilators.

In one embodiment, the present invention provides methods and compositions useful for regulating γ-amino-butyric acid activity.

The present invention provides for multiple methods for delivering the compounds of the invention. The compounds may be provided, for example, as pharmaceutical compositions in multiple formats as well, including, but not limited to, tablets, capsules, pills, lozenges, syrups, ointments, creams, elixirs, suppositories, suspensions, inhalants, injections (including depot preparations), and liquids.

A list of types of drugs, and specific drugs within categories which are encompassed within the invention is provided below.

Adrenergic: Adrenalone; Amidephrine Mesylate; Apraclonidine Hydrochloride; Brimonidine Tartrate; Dapiprazole Hydrochloride; Deterenol Hydrochloride; Dipivefrin; Dopamine Hydrochloride; Ephedrine Sulfate; Epinephrine; Epinephrine Bitartrate; Epinephryl Borate; Esproquin Hydrochloride; Etafedrine Hydrochloride; Hydroxyamphetamine Hydrobromide; Levonordefrin; Mephentermine Sulfate; Metaraminol Bitartrate; Metizoline Hydrochloride; Naphazoline Hydrochloride; Norepinephrine Bitartrate; Oxidopamine; Oxymetazoline Hydrochloride; Phenylephrine Hydrochloride; Phenylpropanolamine Hydrochloride; Phenylpropanolamine Polistirex; Prenalterol Hydrochloride; Propylhexedrine; Pseudoephedrine Hydrochloride; Tetrahydrozoline Hydrochloride; Tramazoline Hydrochloride; Xylometazoline Hydrochloride.

Adrenocortical steroid: Ciprocinonide; Desoxycorticosterone Acetate; Desoxycorticosterone Pivalate; Dexamethasone Acetate; Fludrocortisone Acetate; Flumoxonide; Hydrocortisone Hemisuccinate; Methylprednisolone Hemisuccinate; Naflocort; Procinonide; Timobesone Acetate; Tipredane.

Adrenocortical suppressant: Aminoglutethimide; Trilostane.

Aldosterone antagonist: Canrenoate Potassium; Canrenone; Dicirenone; Mexrenoate Potassium; Prorenoate Potassium; Spironolactone.

Amino acid: Alanine; Aspartic Acid; Cysteine Hydrochloride; Cystine; Histidine; Isoleucine; Leucine; Lysine; Lysine Acetate; Lysine Hydrochloride; Methionine; Phenylalanine; Proline; Serine; Threonine; Tryptophan; Tyrosine; Valine.

Analeptic: Modafinil.

Analgesic: Acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carbaspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride; Epirizole; Ergotamine Tartrate; Ethoxazene Hydrochloride; Etofenamate; Eugenol; Fenoprofen; Fenoprofen Calcium; Fentanyl Citrate; Floctafenine; Flufenisal; Flunixin; Flunixin Meglumine; Flupirtine Maleate; Fluproquazone; Fluradoline Hydrochloride; Flurbiprofen; Hydromorphone Hydrochloride; Ibufenac; Indoprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lomoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol; Nefopam Hydrochloride; Nexeridine Hydrochloride; Noracymethadol Hydrochloride; Ocfentanil Hydrochloride; Octazamide; Olvanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propiram Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salethamide Maleate; Salicylamide; Salicylate Meglumine; Salsalate; Sodium Salicylate;

Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride; Volazocine; Xorphanol Mesylate; Xylazine Hydrochloride; Zenazocine Mesylate; Zomepirac Sodium; Zucapsaicin.

Antihypertensive: Aflyzosin Hydrochloride; Alipamide; Althiazide; Amiquinsin Hydrochloride; Amlodipine Besylate; Amlodipine Maleate; Anaritide Acetate; Atiprosin Maleate; Belfosdil; Bemitradine; Bendacalol Mesylate; Bendroflumethiazide; Benzthiazide; Betaxolol Hydrochloride; Bethanidine Sulfate; Bevantolol Hydrochloride; Biclodil Hydrochloride; Bisoprolol; Bisoprolol Fumarate; Bucindolol Hydrochloride; Bupicomide; Buthiazide: Candoxatril; Candoxatrilat; Captopril; Carvedilol; Ceronapril; Chlorothiazide Sodium; Cicletanine; Cilazapril; Clonidine; Clonidine Hydrochloride; Clopamide; Cyclopenthiazide; Cyclothiazide; Darodipine; Debrisoquin Sulfate; Delapril Hydrochloride; Diapamide; Diazoxide; Dilevalol Hydrochloride; Diltiazem Malate; Ditekiren; Doxazosin Mesylate; Ecadotril; Enalapril Maleate; Enalaprilat; Enalkiren; Endralazine Mesylate; Epithiazide; Eprosartan; Eprosartan Mesylate; Fenoldopam Mesylate; Flavodilol Maleate; Flordipine; Flosequinan; Fosinopril Sodium; Fosinoprilat; Guanabenz; Guanabenz Acetate; Guanacline Sulfate; Guanadrel Sulfate; Guancydine; Guanethidine Monosulfate; Guanethidine Sulfate; Guanfacine Hydrochloride; Guanisoquin Sulfate; Guanoclor Sulfate; Guanoctine Hydrochloride; Guanoxabenz; Guanoxan Sulfate; Guanoxyfen Sulfate; Hydralazine Hydrochloride; Hydralazine Polistirex; Hydroflumethiazide; Indacrinone; Indapamide; Indolaprif Hydrochloride; Indoramin; Indoramin Hydrochloride; Indorenate Hydrochloride; Lacidipine; Leniquinsin; Levcromakalim; Lisinopril; Lofexidine Hydrochloride; Losartan Potassium; Losulazine Hydrochloride; Mebutamate; Mecamylamine Hydrochloride; Medroxalol; Medroxalol Hydrochloride; Methalthiazide; Methyclothiazide; Methyldopa; Methyldopate Hydrochloride; Metipranolol; Metolazone; Metoprolol Fumarate; Metoprolol Succinate; Metyrosine; Minoxidil; Monatepil Maleate; Muzolimine; Nebivolol; Nitrendipine; Ofornine; Pargyline Hydrochloride; Pazoxide; Pelanserin Hydrochloride; Perindopril Erbumine; Phenoxybenzamine Hydrochloride; Pinacidil; Pivopril; Polythiazide; Prazosin Hydrochloride; Primidolol; Prizidilol Hydrochloride; Quinapril Hydrochloride; Quinaprilat; Quinazosin Hydrochloride; Quinelorane Hydrochloride; Quinpirole Hydrochloride; Quinuclium Bromide; Ramipril; Rauwolfia *Serpentina*; Reserpine; Saprisartan Potassium; Saralasin Acetate; Sodium Nitroprusside; Sulfinalol Hydrochloride; Tasosartan; Teludipine Hydrochloride; Temocapril Hydrochloride; Terazosin Hydrochloride; Terlakiren; Tiamenidine; Tiamenidine Hydrochloride; Ticrynafen; Tinabinol; Tiodazosin; Tipentosin Hydrochloride; Trichlormethiazide; Trimazosin Hydrochloride; Trimethaphan Camsylate; Trimoxamine Hydrochloride; Tripamide; Xipamide; Zankiren Hydrochloride; Zofenoprilat Arginine.

Anti-inflammatory: Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

Antinauseant: Buclizine Hydrochloride; Cyclizine Lactate; Naboctate Hydrochloride.

Antineutropenic: Filgrastim; Lenograstim; Molgramostim; Regramostim; Sargramostim.

Blood glucose regulators: Human insulin; Glucagon; Tolazamide; Tolbutamide; Chloropropamide; Acetohexamide and Glipizide.

Carbonic anhydrase inhibitor: Acetazolamide; Acetazolamide Sodium, Dichlorphenamide; Dorzolamide Hydrochloride; Methazolamide; Sezolarmide Hydrochloride.

Cardiac depressant: Acecainide Hydrochloride; Acetylcholine Chloride; Actisomide; Adenosine; Amiodarone; Aprindine; Aprindine Hydrochloride; Artilide Fumarate; Azimilide Dihydrochloride; Bidisomide; Bucainide Maleate; Bucromarone; Butoprozine Hydrochloride; Capobenate Sodium; Capobenic Acid; Cifenline; Cifenline Succinate; Clofilium Phosphate; Disobutamide; Disopyramide; Disopyramide Phosphate; Dofetilide; Drobuline; Edifolone Acetate; Emilium Tosylate; Encainide Hydrochloride; Flecainide Acetate; Ibutilide Fumarate; Indecainide Hydrochloride; Ipazilide Fumarate; Lorajmine Hydrochloride; Lorcainide Hydrochloride; Meobentine Sulfate; Mexiletine Hydrochloride; Modecainide; Moricizine; Oxiramide; Pirmenol Hydrochloride; Pirolazamide; Pranolium Chloride; Procainamide Hydrochloride; Propafenone Hydrochloride; Pyrinoline; Quindonium Bromide; Quinidine Gluconate; Quinidine Sulfate; Recainam Hydrochloride; Recainam Tosylate; Risotilide Hydrochloride; Ropitoin Hydrochloride; Sematilide Hydrochloride; Suricainide Maleate; Tocainide; Tocainide Hydrochloride; Transcainide.

Cardiotonic: Actodigin; Amrinone; Bemoradan; Butopamine; Carbazeran; Carsatrin Succinate; Deslanoside; Digitalis; Digitoxin; Digoxin; Dobutamine; Dobutamine Hydrochloride; Dobutamine Lactobionate; Dobutamine Tartrate; Enoximone; Imazodan Hydrochloride; Indolidan; Isomazole Hydrochloride; Levdobutamine Lactobionate; Lixazinone Sulfate; Medorinone; Milrinone; Pelrinone Hydrochloride; Pimobendan; Piroximone; Prinoxodan; Proscillaridin; Quazinone; Tazolol Hydrochloride; Vesnarinone.

Cardiovascular agent: Dopexamine; Dopexamine Hydrochloride.

Choleretic: Dehydrocholic Acid; Fencibutirol; Hymecromone; Piprozolin; Sincalide; Tocamphyl.

Cholinergic: Aceclidine; Bethanechol Chloride; Carbachol; Demecarium Bromide; Dexpanthenol; Echothiophate Iodide; Isoflurophate; Methacholine Chloride; Neostigmine Bromide; Neostigmine Methylsulfate; Physostigmine; Physostigmine Salicylate; Physostigmine Sulfate; Pilocarpine; Pilocarpine Hydrochloride; Pilocarpine Nitrate; Pyridostigmine Bromide.

Cholinergic agonist: Xanomeline; Xanomeline Tartrate.

Cholinesterase Deactivator: Obidoxime Chloride; Pralidoxime Chloride; Pralidoxime Iodide; Pralidoxime Mesylate.

Dopamine receptor agonist: cabergoline (Dostinex)

Hormone: Diethylstilbestrol; Progesterone; 17-hydroxy progesterone; Medroxyprogesterone; Norgestrel; Norethynodrel; Estradiol; Megestrol (Megace); Norethindrone; Levonorgestrel; Ethyndiol; Ethinyl estradiol; Mestranol; Estrone; Equilin; 17-alpha-dihydroequilin; equilenin; 17-alpha-dihydroequilenin; 17-alpha-estradiol; 17-beta-estradiol; Leuprolide (lupron); Glucagon; Testolactone; Clomiphene; Han memopausal gonadotropins; Human chorionic gonadotropin; Urofollitropin; Bromocriptine; Gonadorelin; Luteinizing hormone releasing hormone and analogs; Gonadotropins; Danazol; Testosterone; Dehydroepiandrosterone; Androstenedione; Dihydroestosterone; Relaxin; Oxytocin; Vasopressin; Folliculostatin; Follicle regulatory protein; Gonadoctrinins; Oocyte maturation inhibitor; Insulin growth factor; Follicle Stimulating Hormone; Luteinizing hormone; Tamoxifen.; Corticorelin Ovine Triftutate; Cosyntropin; Metogest; Pituitary, Posterior; Seractide Acetate; Somalapor; Somatrem; Somatropin; Somenopor; Somidobove.

Relaxant: Adiphenine Hydrochloride; Alcuronium Chloride; Aminophylline; Azumolene Sodium; Baclofen; Benzoctamine Hydrochloride; Carisoprodol; Chlorphenesin Carbamate; Chlorzoxazone; Cinflumide; Cinnamedrine; Clodanolene; Cyclobenzaprine Hydrochloride; Dantrolene; Dantrolene Sodium; Fenalanide; Fenyripol Hydrochloride; Fetoxylate Hydrochloride; Flavoxate Hydrochloride; Fletazepam; Flumetramide; Flurazepam Hydrochloride; Hexafluorenium Bromide; Isomylamine Hydrochloride; Lorbamate; Mebeverine Hydrochloride; Mesuprine Hydrochloride; Metaxalone; Methocarbamol; Methixene Hydrochloride; Nafomine Malate; Nelezaprine Maleate; Papaverine Hydrochloride; Pipoxolan Hydrochloride; Quinctolate; Ritodrine; Ritodrine Hydrochloride; Rolodine; Theophylline Sodium Glycinate; Thiphenamil Hydrochloride; Xilobam.

Sedative-hypnotic: Allobarbital; Alonimid; Alprazolam; Amobarbital Sodium; Bentazepam; Brotizolam; Butabarbital; Butabarbital Sodium; Butalbital; Capuride; Carbocloral; Chloral Betaine; Chloral Hydrate; Chlordiazepoxide Hydrochloride; Cloperidone Hydrochloride; Clorethate; Cyprazepam; Dexclamol Hydrochloride; Diazepam; Dichloralphenazone; Estazolam; Etchlorvynol; Etomidate; Fenobam; Flunitrazepam; Fosazepam; Glutethimide; Halazepam; Lormetazepam; Mecloqualone; Meprobamate; Methaqualone; Midaflur; Paraldehyde; Pentobarbital; Pentobarbital Sodium; Perlapine; Prazepam; Quazepam; Reclazepam; Roletamide; Secobarbital; Secobarbital Sodium; Suproclone; Thalidomide; Tracazolate; Trepipam Maleate; Triazolam; Tricetamide; Triclofos Sodium; Trimetozine; Uldazepam; Zaleplon; Zolazepam Hydrochloride; Zolpidem Tartrate.

Serotonin antagonist: Altanserin Tartrate; Amesergide; Ketanserin; Ritanserin.

Serotonin inhibitor: Cinanserin Hydrochloride; Fenclonine; Fonazine Mesylate; Xylamidine Tosylate.

Serotonin receptor antagonist: Tropanserin Hydrochloride.

Stimulant: Amfonelic Acid; Amphetamine Sulfate; Ampyzine Sulfate; Arbutamine Hydrochloride; Azabon; Caffeine; Ceruletide; Ceruletide Diethylamine; Cisapride; Dazopride Fumarate; Dextroamphetamine; Dextroamphetamine Sulfate; Difluanine Hydrochloride; Dimefline Hydrochloride; Doxapram Hydrochloride; Etryptamine Acetate; Ethamivan; Fenethylline Hydrochloride; Flubanilate Hydrochloride; Flurothyl; Histamine Phosphate; Indriline Hydrochloride; Mefexamide; Methamphetamine Hydrochloride; Methylphenidate Hydrochloride; Pemoline; Pyrovalerone Hydrochloride; Xamoterol; Xamoterol Fumarate. Synergist: Proadifen Hydrochloride.

Thyroid hormone: Levothyroxine Sodium; Liothyronine Sodium; Liotrix.

Thyroid inhibitor: Methimazole; Propyithiouracil.

Thyromimetic: Thyromedan Hydrochloride.

Cerebral ischemia agents: Dextrorphan Hydrochloride.

Vasoconstrictor: Angiotensin Amide; Felypressin; Methysergide; Methysergide Maleate.

Vasodilator: Alprostadil; Azaclorzine Hydrochloride; Bamethan Sulfate; Bepridil Hydrochloride; Buterizine; Cetiedil Citrate; Chromonar Hydrochloride; Clonitrate; Diltiazem Hydrochloride; Dipyridamole; Droprenilamine; Erythrityl Tetranitrate; Felodipine; Flunarizine Hydrochloride; Fostedil; Hexobendine; Inositol Niacinate; Iproxamine Hydrochloride; Isosorbide Dinitrate; Isosorbide Mononitrate; Isoxsuprine Hydrochloride; Lidoflazine; Mefenidil; Mefenidil Fumarate; Mibefradil Dihydrochloride; Mioflazine Hydrochloride; Mixidine; Nafronyl Oxalate; Nicardipine Hydrochloride; Nicergoline; Nicorandil; Nicotinyl Alcohol; Nifedipine; Nimodipine; Nisoldipine; Oxfenicine; Oxprenolol Hydrochloride; Pentaerythritol Tetranitrate; Pentoxifylline; Pentrinitrol; Perhexiline Maleate; Pindolol; Pirsidomine; Prenylamine; Propatyl Nitrate; Suloctidil; Terodiline Hydrochloride; Tipropidil Hydrochloride; Tolazoline Hydrochloride; Xanthinol Niacinate.

The present invention further encompasses the use of combination viral or gene therapy, and pharmacotherapy.

Suitable preparations include injectables, either as liquid solutions or suspensions, however, solid forms suitable for solution in, suspension in, liquid prior to injection, may also be prepared. The preparation may also be emulsified, or the polypeptides encapsulated in liposomes. The active ingredients are often mixed with excipients which are pharmaceutically acceptable and compatible with the active ingredient. Suitable excipients are, for example, water saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants.

The present invention further encompasses kits.

Compositions of the present invention may be presented in a pack or dispenser device, such as an FDA approved kit, which may contain one or more unit dosage forms containing the therapeutic compound as described herein.

In some embodiments, the kit may include a therapeutic compound (as described herein), metal or plastic foil, such as a blister pack, a dispenser device or an applicator, tubes, buffers, and instructions for administration. The various reagent components of the kits may be present in separate containers, or some or all of them may be pre-combined into a reagent mixture in a single container, as desired. The dispenser device or applicator may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

EXAMPLES

Example 1—RV-A16 Studies

Methods

Human Subjects.

Epitope mapping experiments, direct ex vivo tetramer staining experiments, and in vitro culture assays were carried out in 57 healthy adults (ages 18-45) who were asymptomatic and reported no cold symptoms in the previous 4 days. Three additional healthy non-allergic adults (total IgE <30 IU/ml) were experimentally inoculated with RV-A16.

Intranasal Challenge with Human Rhinovirus-A16.

Three HLA-DR*0401+ subjects who lacked serum neutralizing antibodies for RV-A16 were challenged as described previously with 1 ml of inoculum containing 300 TCID of live RV-A16 (0.5 ml per nostril) [37]. Infection was confirmed based on ≥4-fold rise in serum neutralizing titer, as well as a positive RV culture.

Ethics Statement.

Written informed consent was obtained from all study participants. All studies were approved by the University of Virginia Human Investigation Committee and the Institutional Review Board of Benaroya Research Institute. In addition, rhinovirus challenge studies were approved by the FDA and the NIAID safety committee (Clinical Trials.gov ID NCT02111772).

Neutralizing Antibody Assays.

Serum neutralizing antibodies were tested using established methods [38].

PBMC Isolation and HLA Typing.

PBMCs were isolated from heparinized venous blood by Ficoll gradient centrifugation [39,40]. DNA samples were HLA-typed using DRB1 SSP Unitray Kits (Invitrogen, Carlsbad, Calif.) according to the manufacturer's instructions.

Flow Cytometry Antibodies and Reagents.

Fluorochrome-conjugated monoclonal antibodies for flow cytometry were as follows: anti-CD3 (clone SK7), anti-CD4 (L200), anti-CD14 (MΦP9), anti-CD19 (SJ25C1), anti-CD45RA (HI100), anti-CD185 (RF8B2), anti-CD279 (EH12.1), anti-IL-4 (8D4-8) (BD Biosciences, San Jose, Calif., USA); anti-CD4 (clone SK3), anti-CD25 (BC96), anti-CD27 (O323), anti-CD45RO (UCHL1), anti-CD127 (A019D5), anti-CD183 (G025H7), anti-CD185 (J252D4), anti-CD197 (G043H7), anti-IFN-γ (B27), anti-IL-17A (BL168), anti-IL-21 (3A3-N2) (Biolegend, San Diego, Calif., USA); anti-CD194 (clone 205410)(R&D Systems, Minneapolis, Minn., USA); anti-CD3 (clone UCTH1), anti-CD4 (OKT4), anti-CD14 (61D3), anti-CD19 (SJ25C1), anti-CD25 (BC96) (eBioscience, San Diego, Calif., USA). Compensation beads were obtained from BD Biosciences, aqua viability dye was obtained from Invitrogen (Carlsbad, Calif., USA), and anti-PE MicroBeads were obtained from Miltenyi Biotec (Auburn, Calif., USA). Fix & Perm solution and Alexa Fluor® 568 Protein Labeling Kits were obtained from Life Technologies (Carlsbad, Calif., USA).

Rhinovirus Peptide.

A custom RV-A39 peptide (VP2169-188: SDDNWL-NFDGTLLGNLLIFP (SEQ ID NO:57), >90% purity), used to test cross-reactivity, was obtained from New England Peptides (Gardner, Mass., USA).

Tetramer Guided Epitope Mapping and Surface Phenotyping of Tetramer-Positive Cells.

Peptide libraries consisting of 20mers with a 12 amino acid overlap were generated to span the VP1, VP2 and VP4 protein sequences of RV-A16, and VP1 and VP2 protein sequences of RV-A39 (UniprotKB accession # Q82122, Q5XLP5) [41]. Peptide/MHCII (pMHCII) tetramers containing 8 different HLA-DR molecules (DRB1*0101, *0301, *0401, *0404, *0701, *1101, *1501, and DRB5*0101) were then assembled that displayed pooled or individual peptides [42]. Biologically relevant pMHCII complexes were identified by tetramer-guided epitope mapping (TGEM). This involved 2 steps: First, PBMC cultures established from subjects with known HLA-DR types were stimulated with RV peptide pools derived from VP1, VP2, or VP4, and then stained with pMHCII tetramer pools composed of HLA-DR molecules corresponding to those expressed in the test subject; Second, positive signals were de-convoluted by repeating and staining with single-peptide tetramers. Tetramers that gave strong positive signals (~1% of total CD4+ T cells) in the single peptide-tetramer screen in more than one subject, were then re-tested for their ability to detect RV-specific CD4+ T cells in non-stimulated PBMCs (denoted as ex vivo analysis) in multiple subjects.

All experiments were performed in subjects expressing HLA-DR molecules corresponding to the selected tetramer. Precursor frequencies of circulating tetramer+ cells were then calculated by established methods [43]. Tetramer+ cells were phenotyped for surface markers by staining PBMCs with PE-conjugated tetramers, labeling with anti-PE magnetic beads, enriching with an AutoMACS separator (Miltenyi Biotec, Auburn, Calif., USA), and then counterstaining for surface markers. A tetramer displaying an irrelevant peptide, GAD555-567, was used as a staining control [44]. For simplicity, identified RV-A16 peptide epitopes were given a numerical designation.

Assay to Assess T-Cell Cross-Reactivity.

RV-specific CD4+ T cells were expanded in vitro using established methods [42]. Briefly, PBMCs from HLA-DRB 1*0401+ subjects were stimulated with RV-A39 VP2169-188, or else unstimulated, for 14 days. Supplemental IL-2 (10 U/ml) was given days 7-14. Cells were then stained with RV tetramers and re-stimulated with PMA and ionomycin in the presence of Brefeldin A before staining for intracellular cytokines [45]. Cells were analyzed on a BD LSR Fortessa (UVA Flow Cytometry Core Facility) and data analysis was performed using FlowJo version 9.3.3 (Tree Star Inc., Ashland, Oreg.). Analysis and presentation of distributions was performed using SPICE version 5.3, downloaded from a National Institutes of Health website [46].

Sequence Alignment Algorithms.

Amino acid sequences of RV-A16 epitopes were compared with other RV strains by protein BLAST search (NCBI) [47]. Multiple sequence alignments were analyzed using Jalview v. 2.8.2 [48].

HLA Binding and Epitope Prediction.

MHCII binding predictions for RV-A16 and RV-A39 polyproteins were generated using the Immune Epitope Database (IEDB) Consensus method [49,50]. This method integrates 3 different epitope prediction methods—SMM-align, NN-align, and the combinatorial peptide scanning library (Comblib)—in order to identify a 15mer consensus epitope [49-52]. In cases where Comblib was not available for a given allele, the Sturniolo method was used [53]. MULTIPRED2, an epitope prediction program that utilizes the NetMHCpan and NetMHCIIpan algorithms, was used to predict 9mer core epitopes for numerous alleles corresponding to HLA supertypes, [54-57]. This analysis was performed for the major HLA class II DR supertypes containing alleles used in TGEM (DR1, DR3, DR4, DR7, DR11 and DR15), as well as minor class II DR supertypes and class I supertypes. NetMHCIIpan was also used to predict 19mer class II epitopes for single HLA alleles.

Population Coverage Calculation.

Population coverage analysis was performed using the Population Coverage Calculation tool from the IEDB Analysis Resource, which accounts for all racial and ethnic groups in the US [58]. The peptide/MHC allele binding input was derived from TGEM results and MULTIPRED2 analysis. Only those HLA-DRB1 molecules that were predicted to bind to TGEM-validated peptides ($IC_{50} \leq 500$ nM) were selected for inclusion in the population coverage calculations.

Location of T-Cell Epitopes in the Three-Dimensional Structure of the RV-A16 Capsid.

The location of T cell epitopes within the three-dimensional structure of the VP coat proteins from human RV-A16 and the creation of structural images were done with PyMol, based on the X-ray crystal structure of native RV-A16 at 2.15 Å resolution (PDB code 1aym) [59,60].

Statistical Analysis.

Percentages of CD4+ T cells with discrete phenotypes were compared by the Wilcoxon matched-pairs signed rank test for paired analyses, and the Mann-Whitney test for unpaired analyses. For longitudinal data, linear mixed models were used to analyze within-group differences in cell percentages.

Results

All Tables can be found after the Bibliography (before the Claims).

RV-A16 Epitopes Bind Multiple HLA Molecules and are Conserved.

We first sought to identify RV-specific CD4+ T cells in the blood of healthy subjects, and to interrogate their epitope specificity by tetramer-guided epitope mapping (TGEM) [42]. We hypothesized that circulating memory T cells capable of recognizing different RV strains would be readily detected in adults, owing to repeat priming by previous RV infections. Capsid proteins of the commonly studied species A strain, RV-A16, including two external (VP1 and VP2) and one internal (VP4) protein, were selected for analysis. Initially, TGEM was performed in 24 subjects in the context of eight common HLA-DR molecules that provide ≥80% coverage of the US population (DRB1*0101, *0301, *0401, *0404, *0701, *1101, *1501, and DRB5*0101). This process, which involved in vitro expansion of T cells with RV peptides using PBMC cultures, yielded 45 pMHCII tetramers displaying 30 candidate epitopes of VP1 and VP2 (Table S1). No epitopes of VP4 were identified. Of the twenty tetramers that gave strong signals after in vitro cultures, 12 provided reliable signals when used to stain PBMCs directly ex vivo (i.e. without culture), based on frequencies of tetramer+ cells≥2 per million CD4+ T cells tested in ≥3 subjects (n=29). The frequency of circulating T cells recognizing these 12 validated tetramers ranged from 1-148 per million cells, consistent with numbers reported to exist in seronegative individuals in the absence of viral exposure [61]. Four validated tetramers displayed VP1 epitopes and 8 displayed VP2 epitopes, corresponding to 3 and 7 unique epitopes respectively (Table 1 & FIG. 1). Moreover, 2 epitopes (VP1P23 and VP2P21), bound 2 different molecules, indicating HLA promiscuity.

All epitopes mapped to regions of VP1 and VP2 that were highly conserved across RV species A. Specifically, 8 of the 10 epitopes showed ≥85% sequence identity with >88% of all RV-A strains (Table 2), including 3 that had identical sequences with >50% of all species A strains [62]. Though the sequence identity was lower with RV-B strains, 6 epitopes had ≥65% to 95% sequence identity across ≥72% of RV-B strains. As expected, RV-A16 epitopes had the lowest identity with those strains belonging to species C. Nonetheless, "hits" were identified for 13-42% of strains for 6 of the epitopes. Three RV-A16 epitopes ($VP1_{P21}$, $VP2_{P21}$, and $VP1_{P18}$) did not align with any RV-C strain. Using RV-C2 as a distantly related strain for comparison (50.9% sequence identity for the entire capsid polyprotein of RV-A16 [VP1-4]), these 3 epitopes had only 40-45% sequence identity as compared with 55-75% identity for the other epitopes (FIG. S1). Notably, those epitopes with the highest sequence identity (≥70%) retained amino acids necessary for HLA class II binding. Thus, circulating RV-A16-specific CD4+ T cells in HLA-diverse subjects recognize conserved epitopes of external capsid proteins that comprise both species-specific and pan-species varieties.

Predicted Core Epitopes Correspond to Epitopes Identified by TGEM.

At least one 15mer consensus epitope containing a predicted 9mer core epitope was predicted for each TGEM epitope in the context of its relevant HLA molecule by the IEDB consensus method. This method utilizes numerous prediction methods, and accounts for the contribution of flanking residues outside the predicted core, to HLA binding (SMM-Align, NN-Align, Comblib, Sturniolo) (Table 3) [49-53]. Predicted core epitopes mapped to the overlapping sequence of adjacent epitopes identified by TGEM, suggesting a common core, and also localized to molecular regions that were conserved across all RV-A strains (FIG. S2). Re-analysis of the predicted core epitopes of those TGEM epitopes with the lowest identity across all RV species, increased their identity among RV-A strains, but not RV-B and RV-C, compared with the longer TGEM epitope (Table S2). This confirmed that flanking residues not involved in HLA binding contributed to the sequence variability with other RV-A strains. Finally, among all RV-A16 epitopes identified by TGEM, core epitopes of $VP1_{P23}$ and $VP2_{P10}$ were the most highly conserved within the entire picornavirus family (FIG. S3).

VP1 Epitopes of RV-A16 Map to the Hydrophobic Binding Pocket.

Figure 2A:
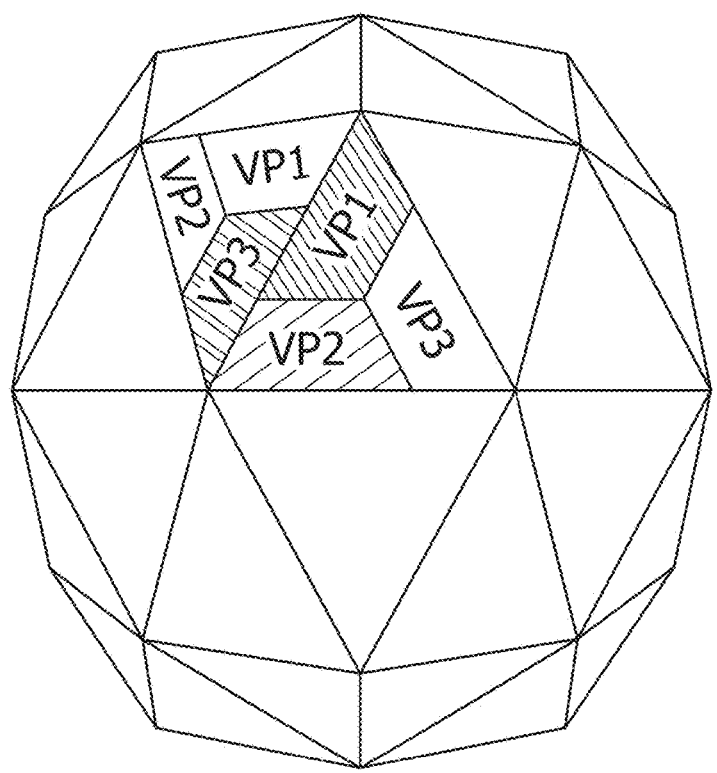
FIG. 2 (A-D). Map of CD4+ T-Cell Epitopes on the Three-Dimensional Structure of RV-A16 Capsid Proteins. (A) Capsid model showing the relative position of VP1, VP2 and VP3, forming an oligomeric subunit on the capsid surface. (B) External and internal view of the capsid showing T-cell epitopes in VP1 and VP2. Ribbon models depict VP1 in green, VP2 in magenta, VP3 in light orange, and VP4 in cyan. Surface representations show only VP1 or VP2 in color, with the three remaining capsid proteins in white. T-cell epitopes are colored as follows: VP1:P18 (orange), P21 (red), P23 (blue) with the 4 overlapping residues between P21 and P23 in violet (overlap hidden from the surface, visible in D); and VP2:P2 and P3 (light green), P10 (wheat), P21 (yellow) and P24-P25-P26 (dark blue). (C) Footprint of the canyon in relation to the triangular capsid subunit formed by VP1+VP2 from one subunit, and VP3 from the adjacent subunit. The drug binding pocket extends from a pore at the base of the canyon into a larger cavity within the core of VP1. Schematic adapted from [66]. (D) Localization of the canyon and the pocket binding factor in VP1 in relation to VP2 and VP3, viewed from the inside of the capsid. Expanded view depicts VP1 only for simplicity, with the T-cell epitopes in color as described in B. Residues which have an atom lying within 4 angstroms of the pocket factor are shown as white sticks and include Ile1098, Asn1099, Leu1100, Asn1212, Met1214, and His 1260 [60]. Two residues of VP1$_{P18}$ associated with the binding pocket (Tyr 1144 and Pro1146) are shown in orange. Lauric acid, a representative pocket factor, is shown as a black stick model in the ribbon models in B and D.
Figure 2B:
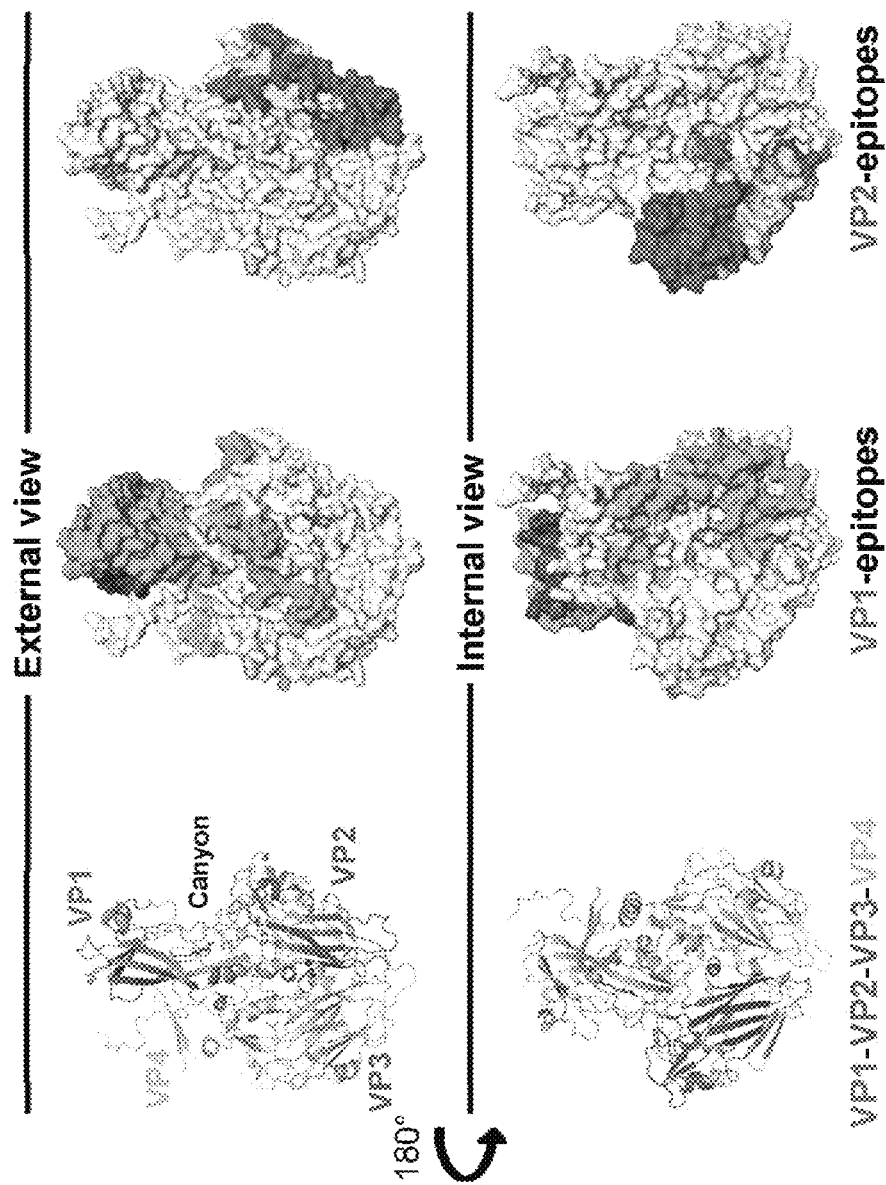

The existence of conserved T-cell epitopes of capsid proteins might seem to contradict the selective pressures that drive antigenic diversity of RV species. Thus, we next explored whether T-cell epitopes mapped to regions of functional significance for the virus. Analyses in the context of the oligomeric subunit formed by the capsid proteins VP1-4, revealed that all T-cell epitopes contained residues located on external and/or internal sides of the viral capsid (FIGS. 2A & B). Additionally, most epitopes were positioned close to adjacent oligomeric subunits.

Figure 2C:
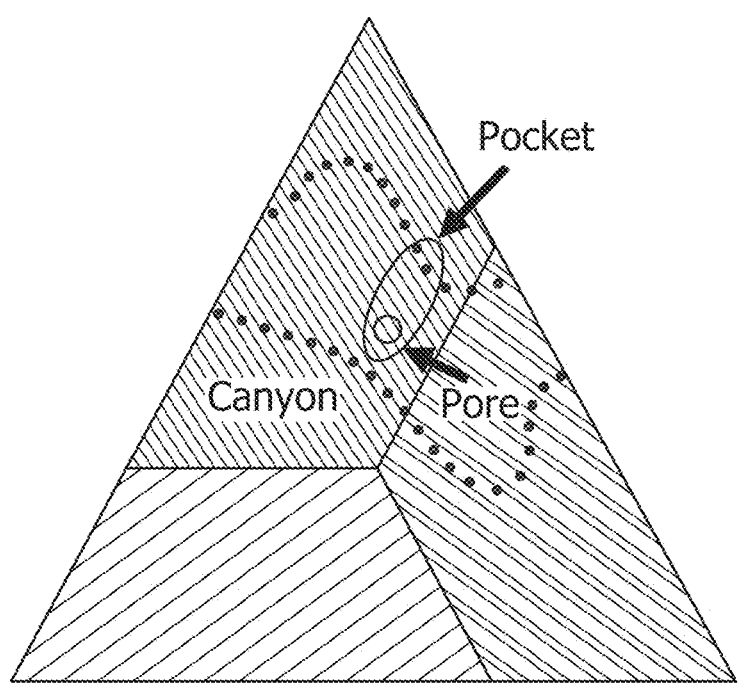
Figure 2D:
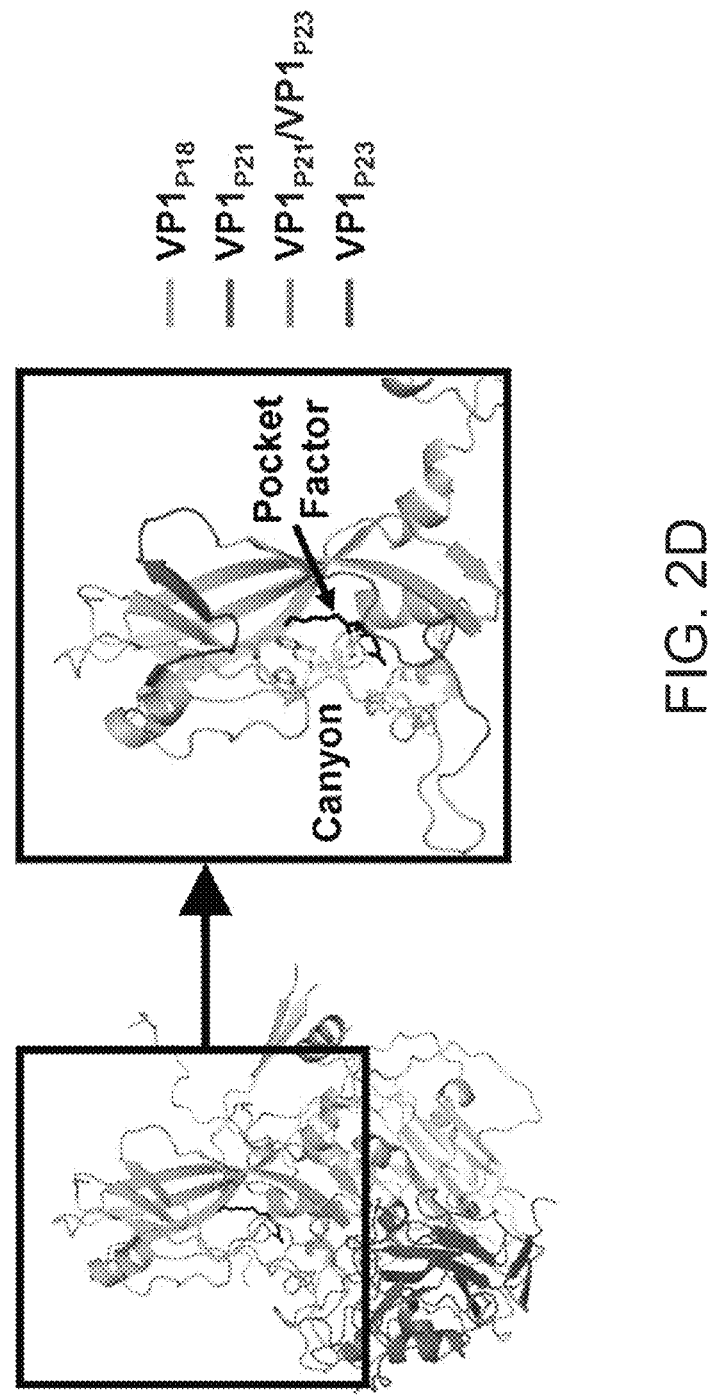

The best characterized structural element of the RV capsid is the binding site for ICAM-1. Interactions with this cell-surface molecule are essential for cellular entry for RV-A and RV-B of the major receptor group, but not for RV-C. ICAM-1 binds in a canyon containing a hydrophobic binding pocket occupied by a pocket factor, which regulates viral entry, uncoating and assembly (FIG. 2C). Analysis of T-cell epitope positions within three-dimensional structures of VP1-4 revealed that each of the three VP1 epitopes mapped to the hydrophobic binding pocket of RV-A16, with two residues of the VP1P18 core epitope (Pro1146 and Tyr1144) residing close to the pocket factor (FIG. 2D) [60,63]. Notably, VP1 epitopes were among those with the least sequence identity with RV-C strains (Table 2 & FIG. S1). Work by other groups has shown that VP1 protein sequences of RV-A are longer compared with those of RV-C, and that the canyon and hydrophobic drug-binding pockets are structurally different between species [64,65]. Together, these observations suggest that positioning of VP1 T-cell epitopes within a region that is functionally important for RV-A, but not RV-C, explains their RV-A specificity.

HLA Class I Binding Motifs and Peptide Length Considerations.

Next, we queried whether RV-A16 epitopes might have the potential to activate CD8+ T cells using MULTIPRED2, which predicts 9mer core epitopes for HLA supertypes encompassing 1,077 class I and class II molecules, without accounting for the contributions of flanking residues to HLA binding [54]. Using a threshold that captures a wide range of HLA binding strengths (IC50≤500 nM), we predicted a high density of class I binding motifs for HLA-A, -B, and -C in two regions, designated "A" (VP1 aa140-200) and "B" (VP2 aa160-220), which corresponded to CD4+ T-cell epitopes identified by TGEM (FIG. 3). These class I epitopes spanned the length of regions A and B. Moreover, they were predicted to bind to molecules belonging to all HLA class I supertypes, and to the majority (>55%) of molecules within most HLA-A and -B supertypes. In relation to HLA class II, a core epitope for all DR supertypes mapped to VP1 region A (aa187-195), with predicted binding to the majority of DR1 and DR7 molecules (81.25% and 87.5% respectively). This epitope matched the predicted core epitope of VP1P23, which is displayed on *0101 and *0701 tetramers (FIG. 3A & Table 3). For VP2, a single DR "hotspot" was predicted (aa189-197 binding 87.5% of the DR1 supertype), which mapped to region B and corresponded to the predicted core epitope of the *0101-restricted peptide VP2P24 (FIG. 3A). When the algorithm was adjusted to predict 19mer epitopes (NetMHCIIpan 19mer), class II epitopes were predicted for 85.7% of epitopes identified by TGEM (versus 21% using 9mer), and those with strongest binding mapped to regions A and B (Table 3 & FIG. S4). These findings were in line with those algorithms that accounted for peptide flanking regions (NN-align and SMM-align), and which gave results matching those obtained by TGEM (Table 3)[51,52]. Consistent with TGEM results for VP4, MULTIPRED2 failed to predict HLA class II epitopes for any common DR supertypes (FIG. S5). Together, these results suggest that RV-A16 peptide epitopes have the potential to activate both CD4+ and CD8+ T cells, and further support the view that peptide length is a key determinant of epitope recognition by virus-specific CD4+ T cells.

Predicted Core Epitopes of RV-A16 Peptides Provide Broad Coverage of the US Population.

Figure 4A:
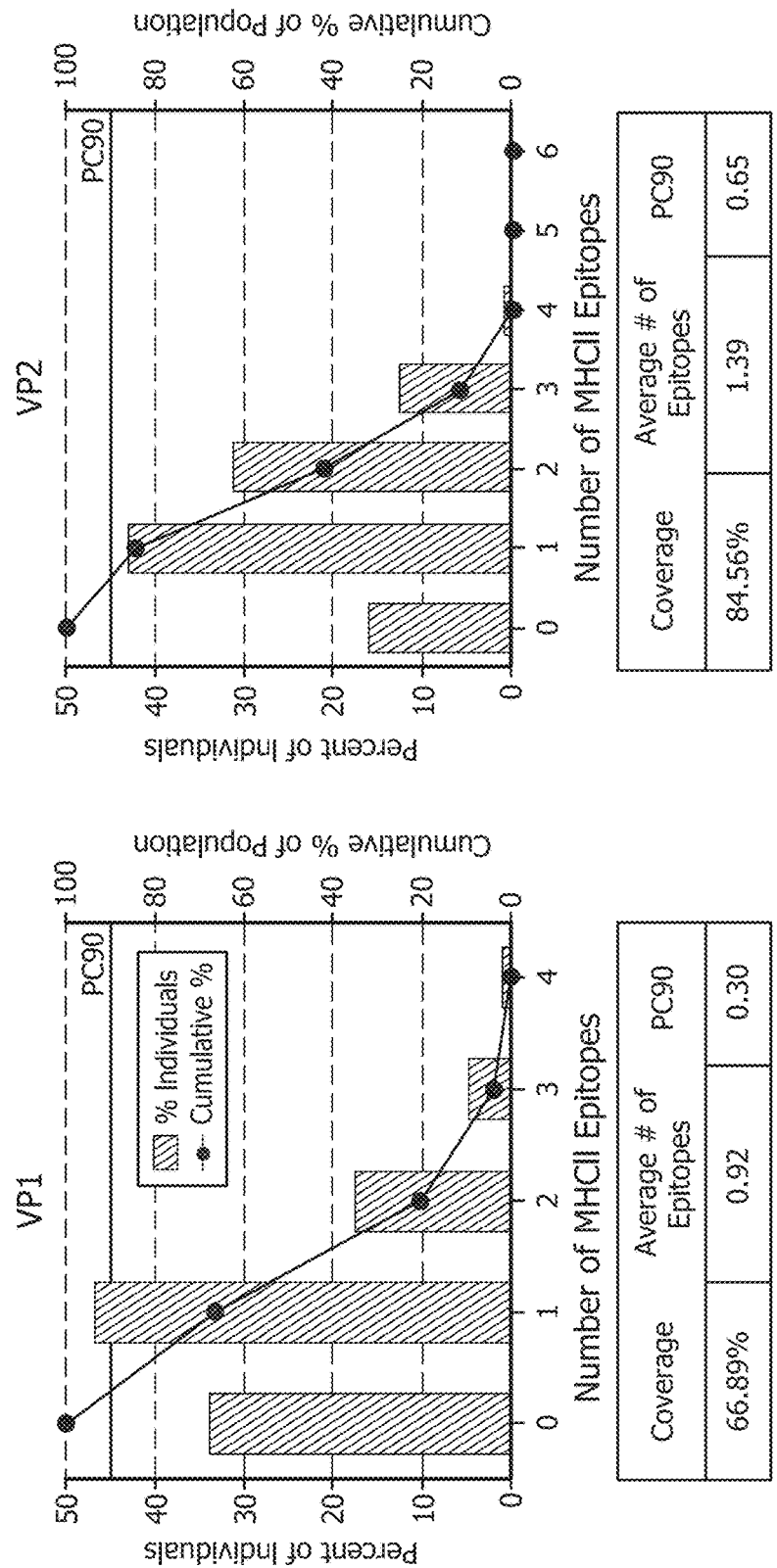
FIG. 4 (A-B). Population Coverage Prediction for T-Cell Epitopes of RV-A16 VP1 and VP2. Epitopes included in the analysis were those 9mers with $IC_{50} \leq 500$ for (A) HLA class II and (B) class I molecules that were nested within validated TGEM peptides, as predicted by MULTI pMHCII—peptide/MHCII
RV—rhinovirus
Teff—T effector cell (e.g., Th1, Th2 and Th17), as well as Tfh
Tfh—T follicular helper cell
TGEM—tetramer-guided epitope mapping
Th—T helper cell
Th1—T helper cell 1; these participate in both cell-mediated immunity and antibody-mediated immunity; they produce different cytokines that other T helper cells Definitions In describing and claiming the invention, the following terminology will be used in accordance with the definitions set forth below.
Figure 4B:
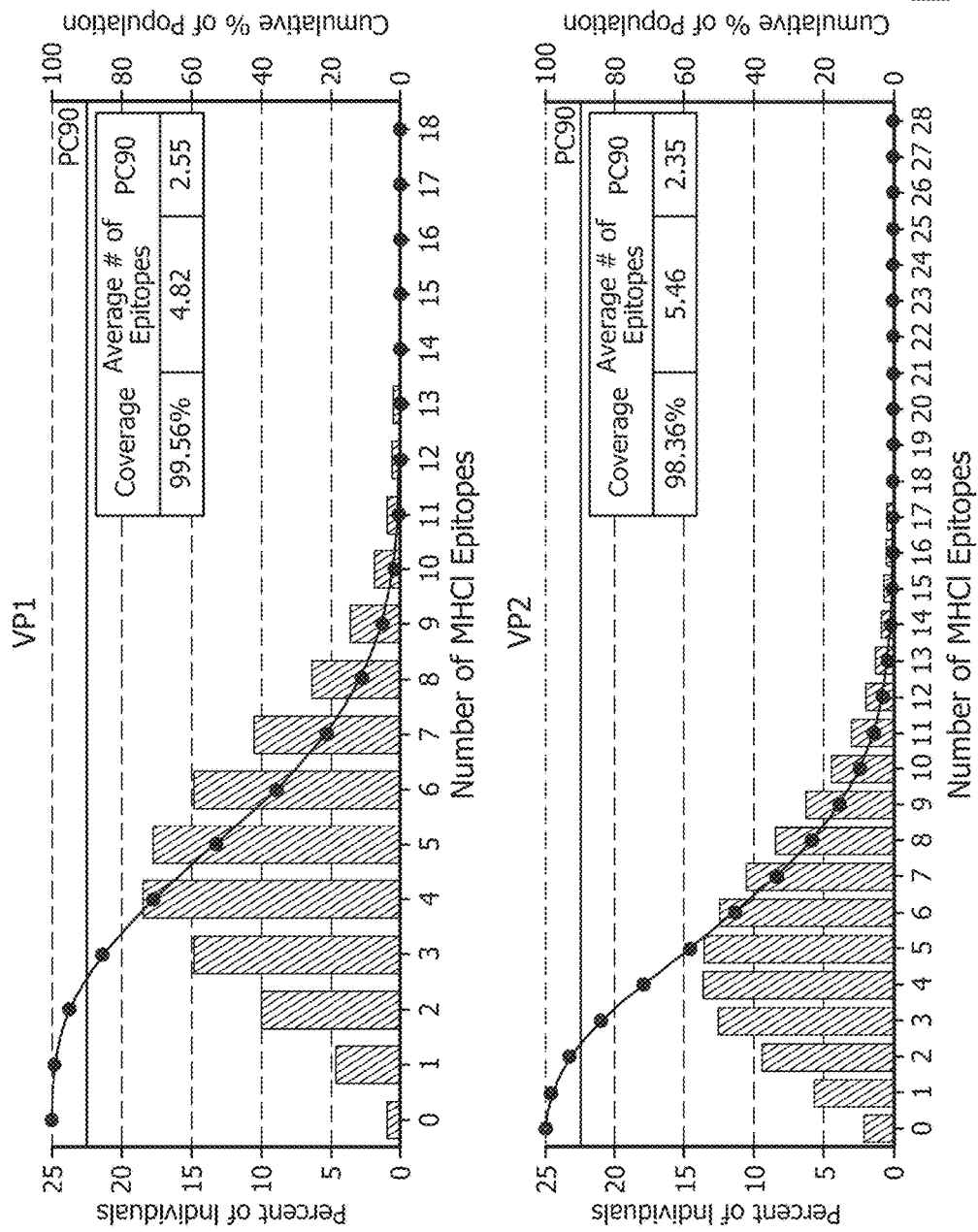

Given the evidence of promiscuous HLA binding for RV-A16 peptides, we assessed US population coverage using the Population Coverage tool of the IEDB [54]. This provided a conservative estimate that excluded any contribution of flanking residues. RV-A16 peptides of VP1 and VP2 were predicted to form HLA class II complexes in 66.89% and 84.56% of the US population respectively, with a combined coverage of 89.65% (FIG. 4A). Higher coverage rates were predicted for class I epitopes (99.56% and 98.36% for VP1 and VP2 peptides respectively) (FIG. 4B).

Epitope-Specific T Cells are Th1-Like and Respond to RV Infection.

Figure 5A:
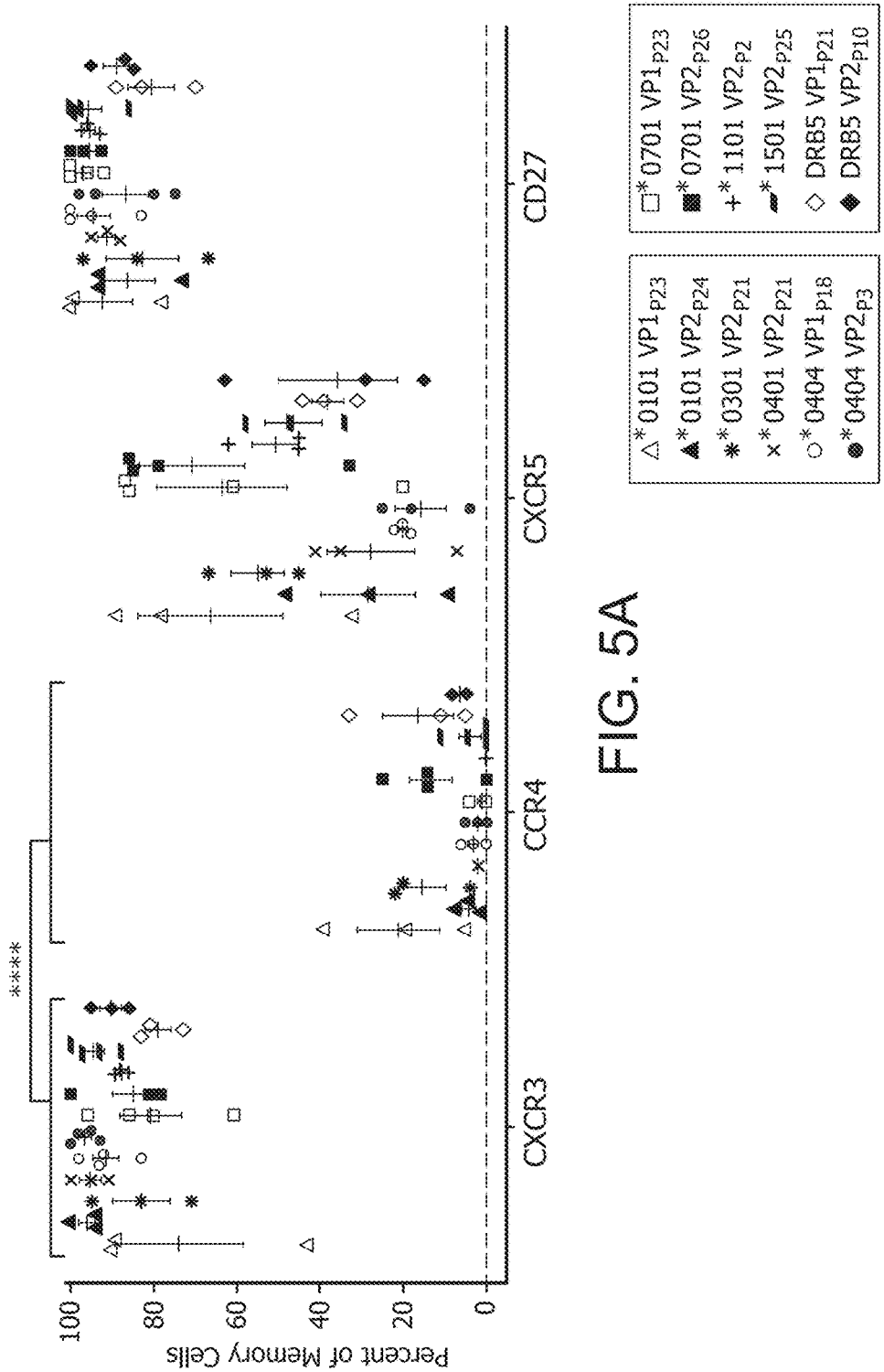
Figure 5B:
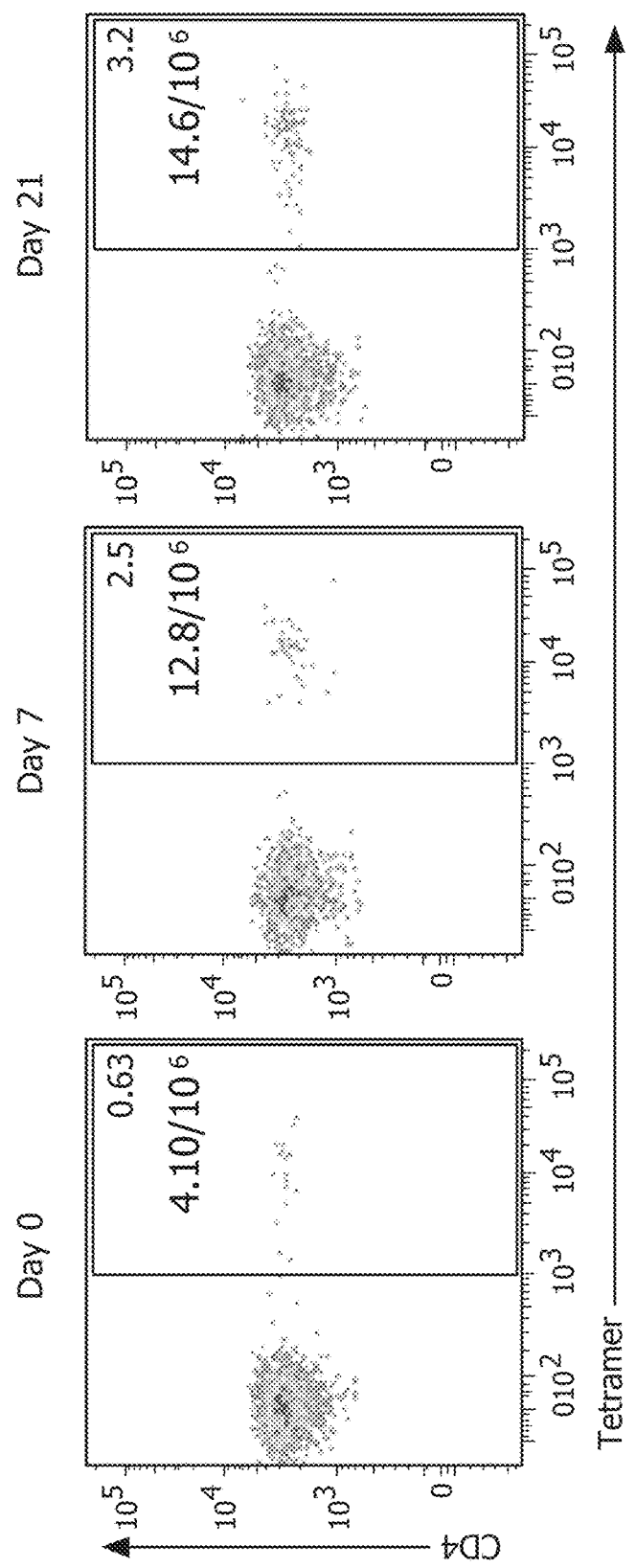
Figure 5C:
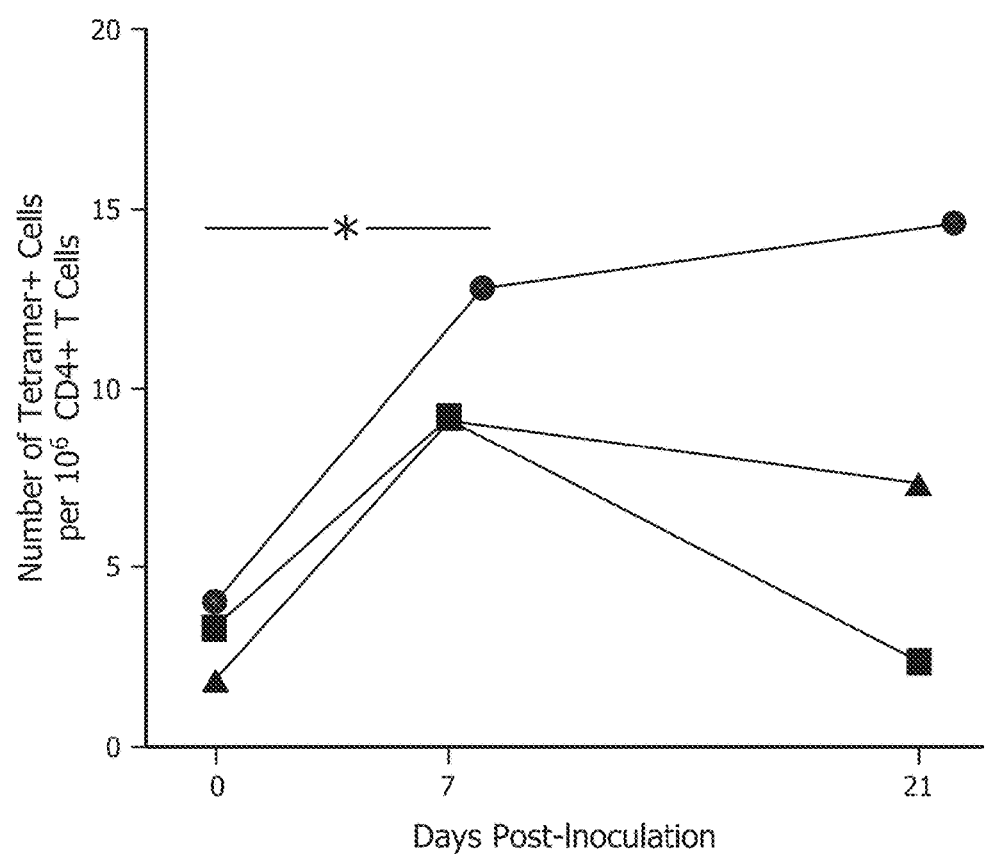
Figure 5D:
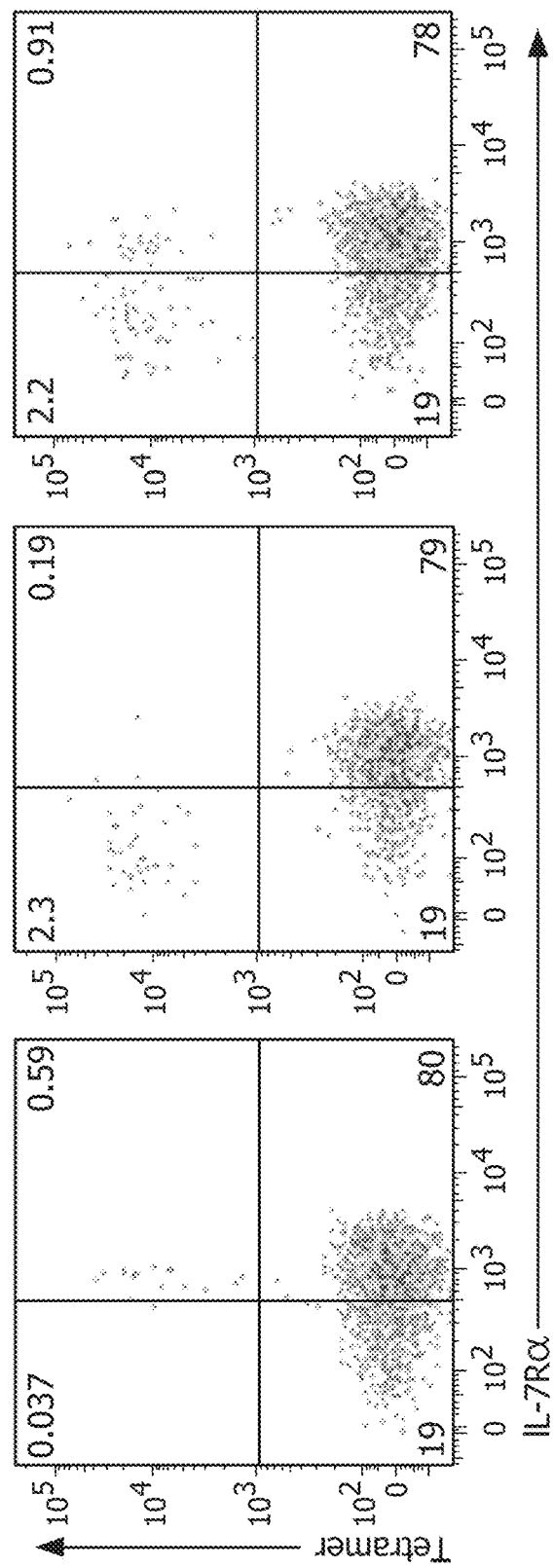
Figure 5E:
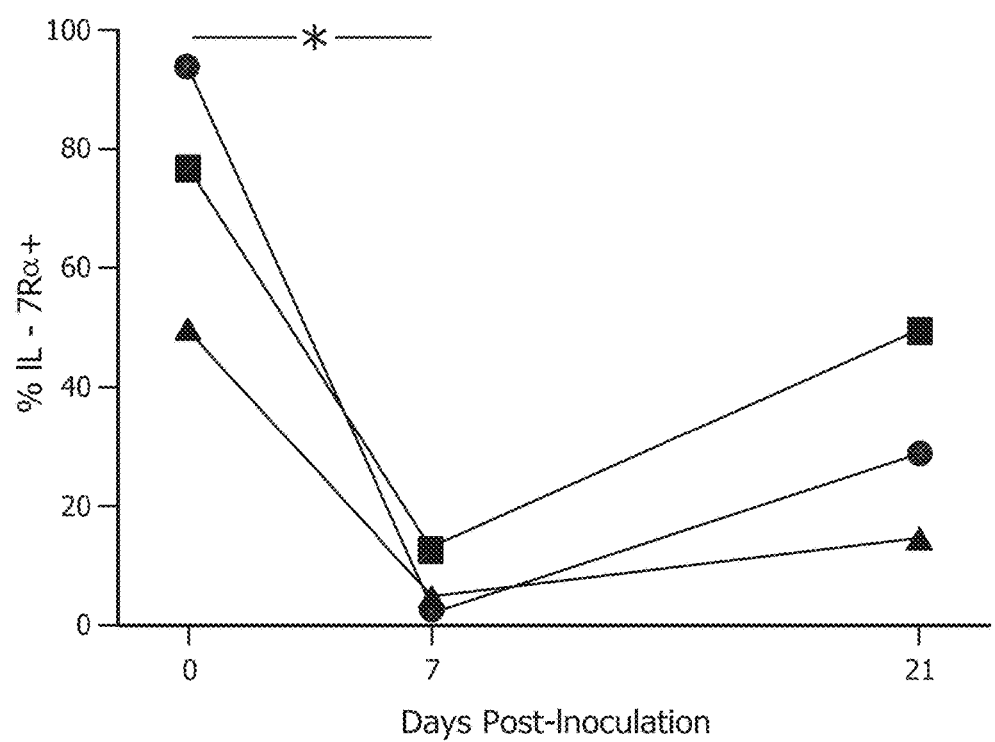

Considering the cross-reactive and immunogenic potential of RV-A16 epitopes, we tested whether cognate CD4+ T cells displayed protective attributes. Analysis of "untouched" tetramer+ cells directly ex vivo revealed that the majority of RV-specific CD4+ T cells displayed a memory Th1 phenotype (CD45RAnegCXCR3+CCR4neg CD27+) that was uniform across all epitope specificities (FIG. 5A) [67-69]. These cells included a CXCR5+ subset, suggesting the presence of T follicular helper (Tfh) cells with lymph node-homing capabilities. At 7 days after in vivo infection with RV-A16, circulating epitope-specific T cells increased in numbers and were activated based on decreased expression of IL-7Rα (FIGS. 5B-E). Thus, expansion of circulating T cells directed against conserved epitopes is a feature of adaptive immunity to RV.

Epitope-Specific T Cells Recognize Cross-Reactive Determinants.

Figure 6B:
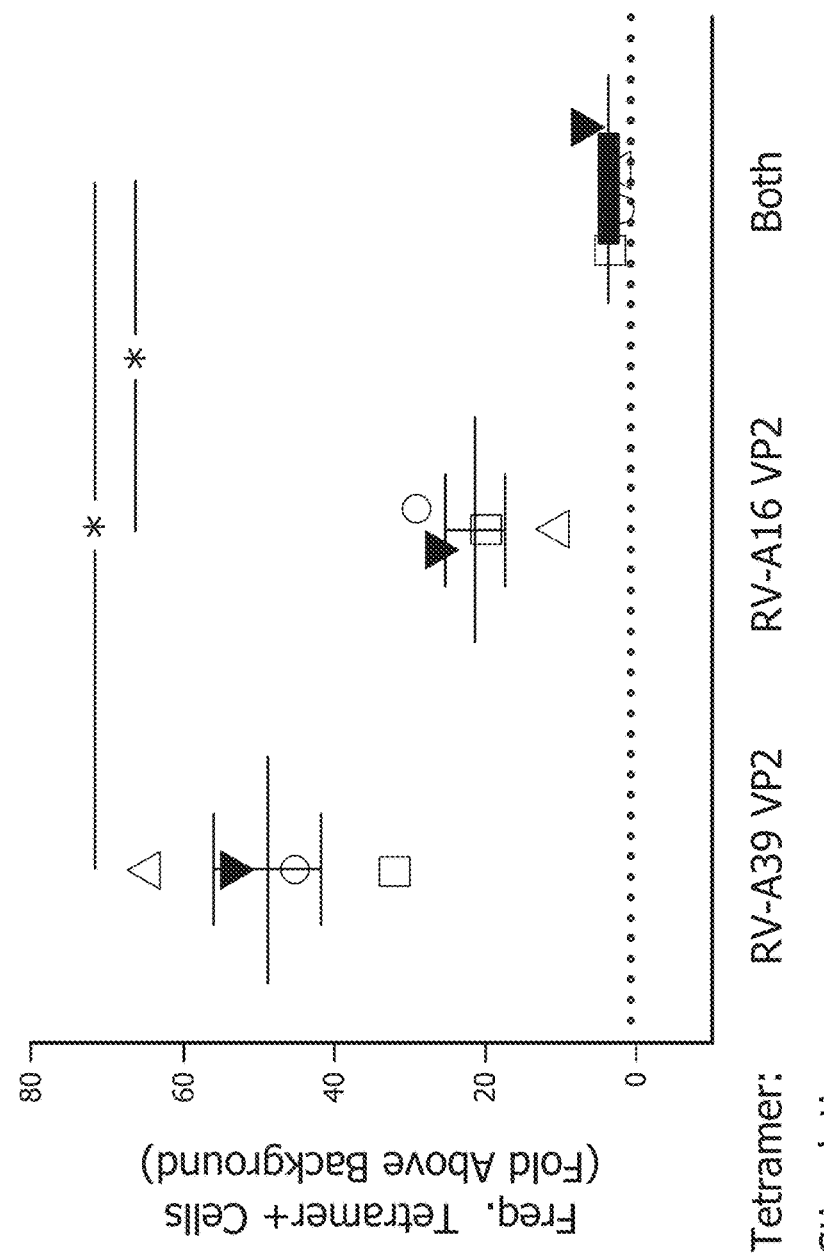
Figure 6C:
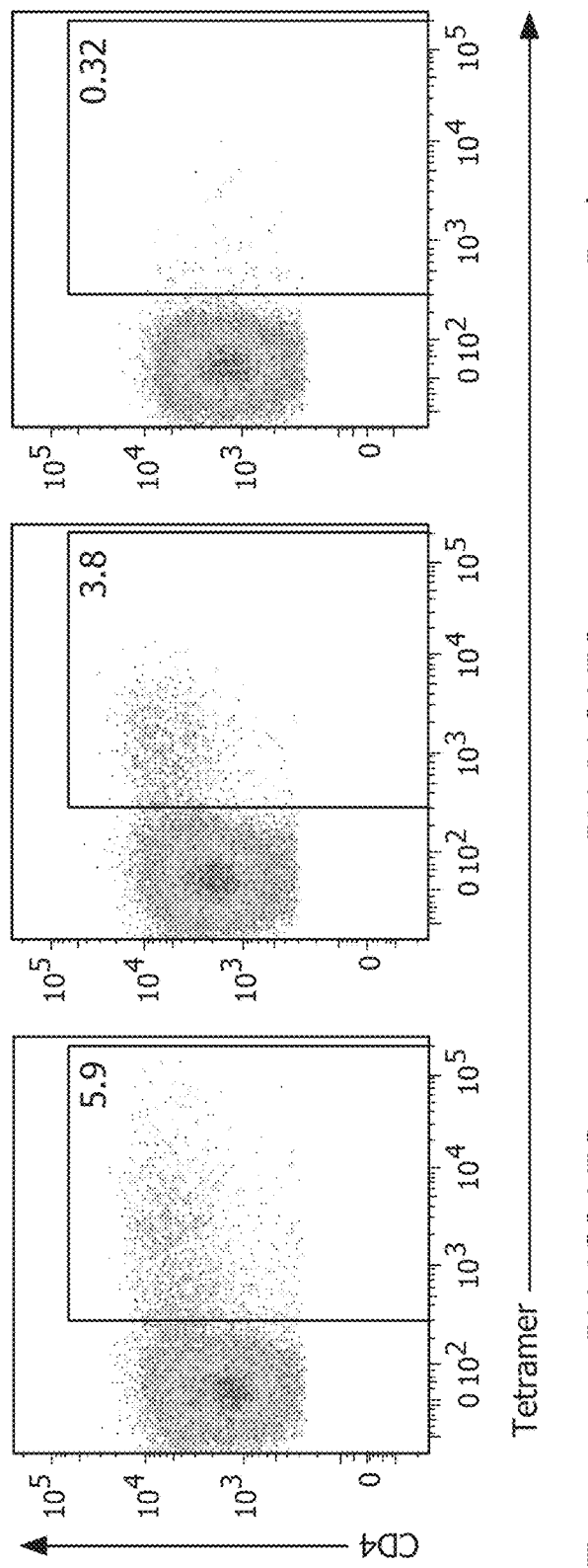
Figure 6D:
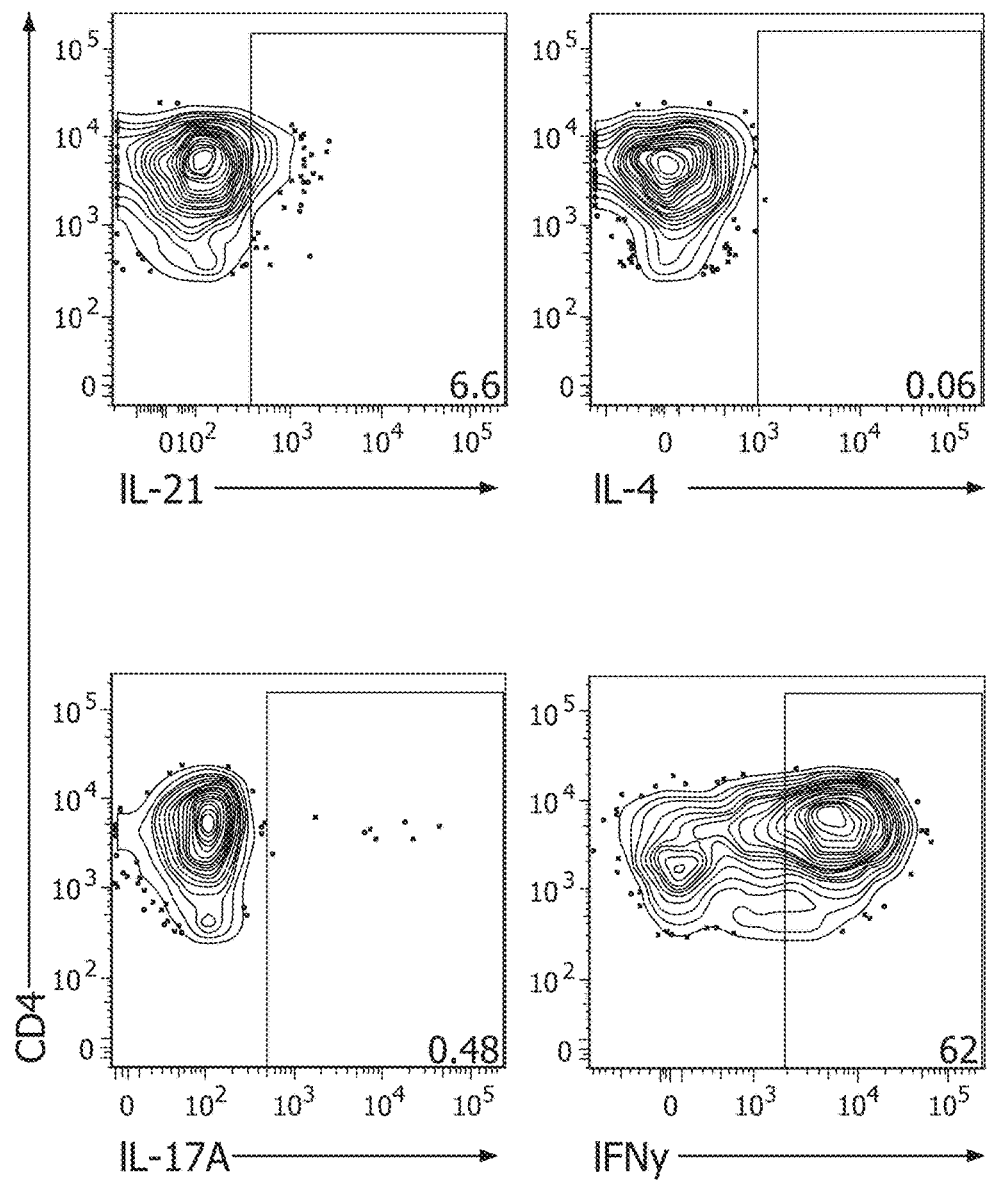
Figure 6E:
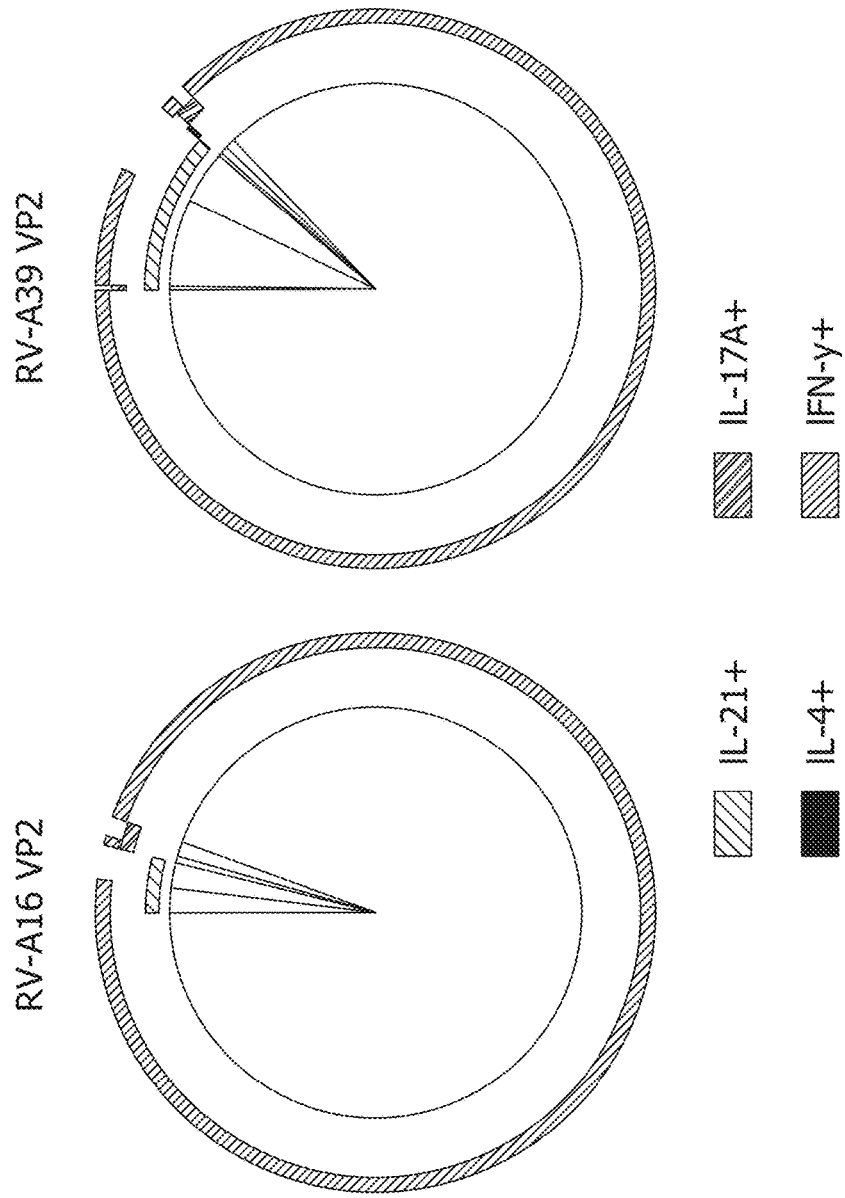
Figure 8:
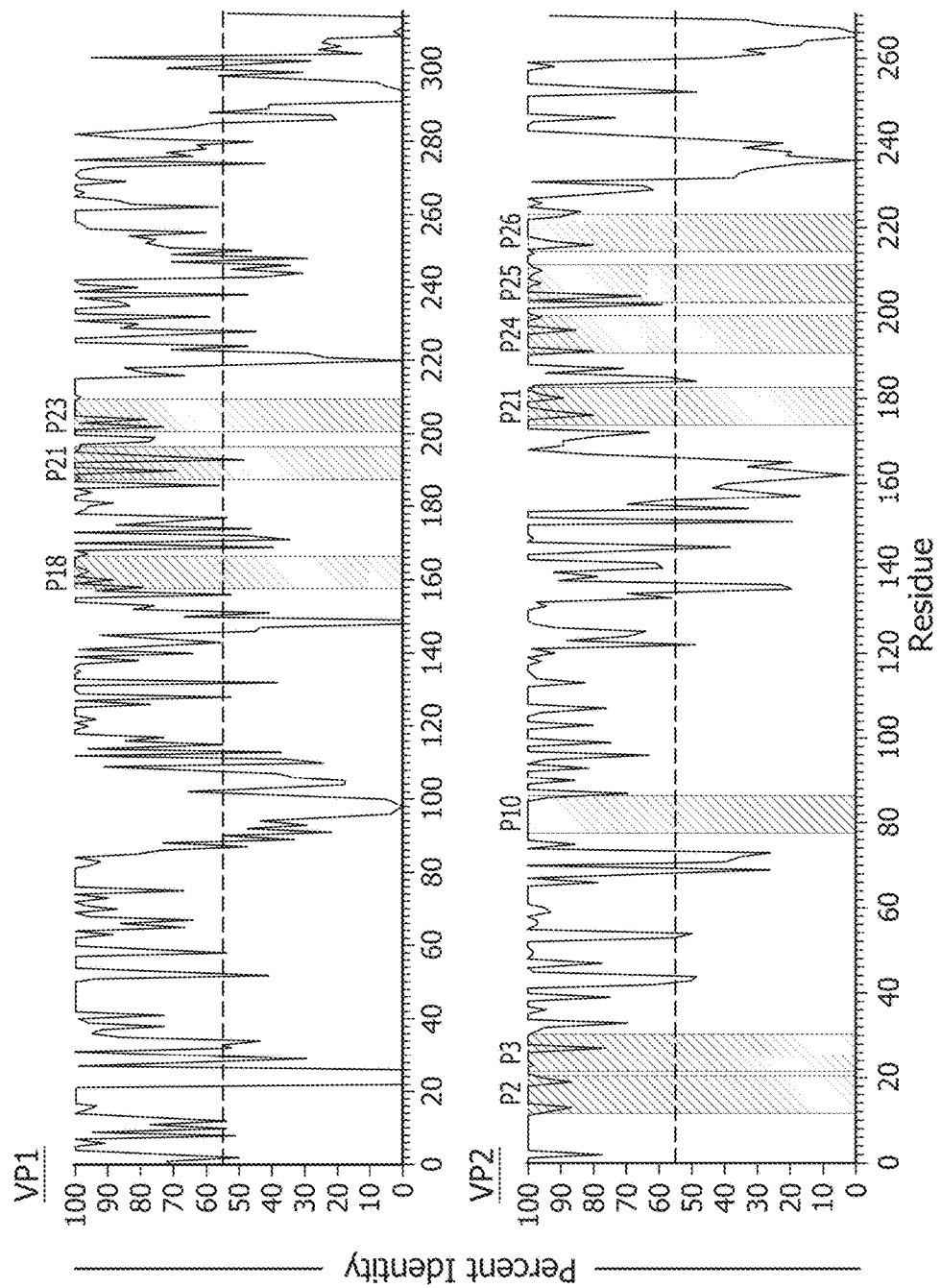
Figure 10A:
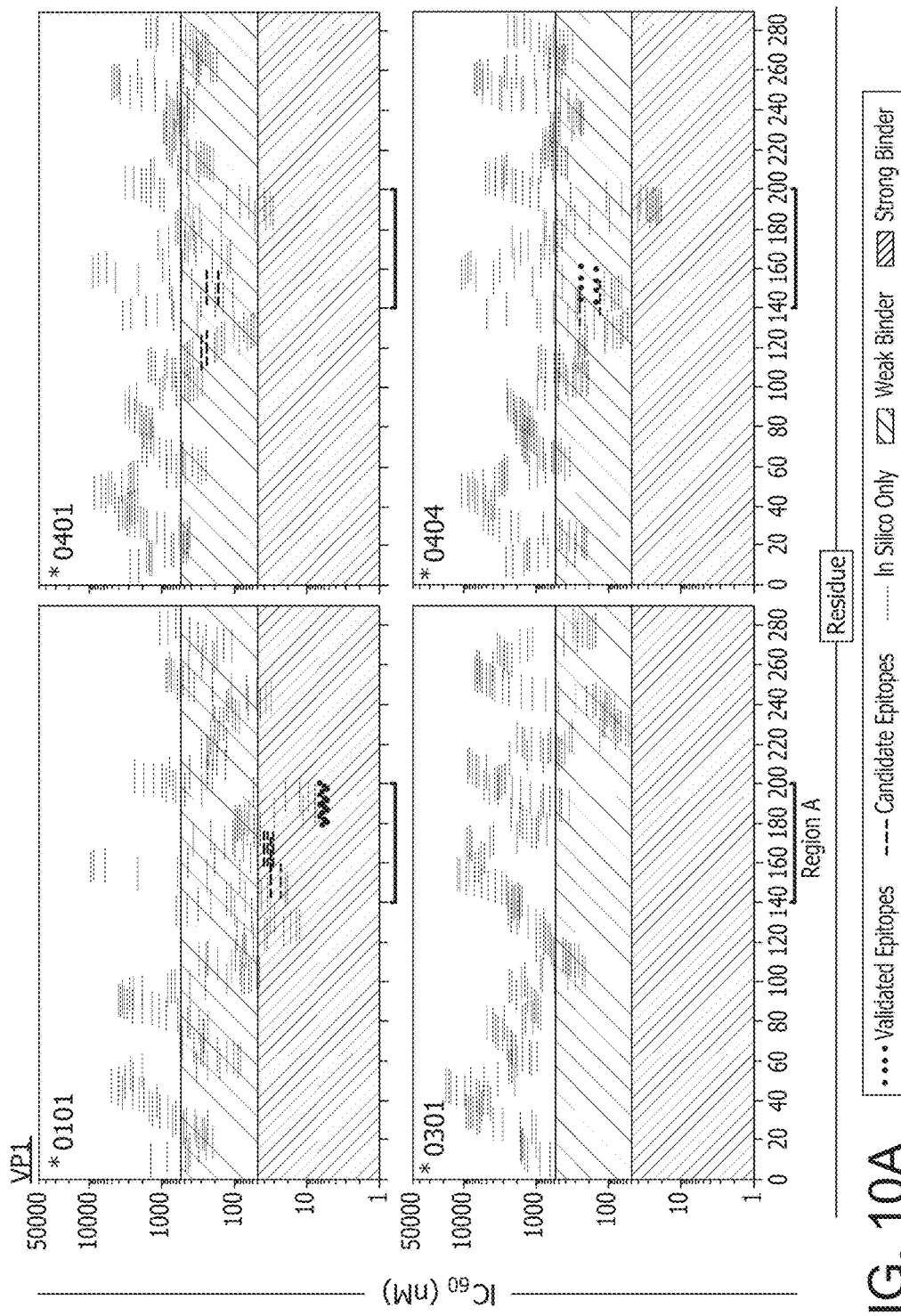
Figure 10B:
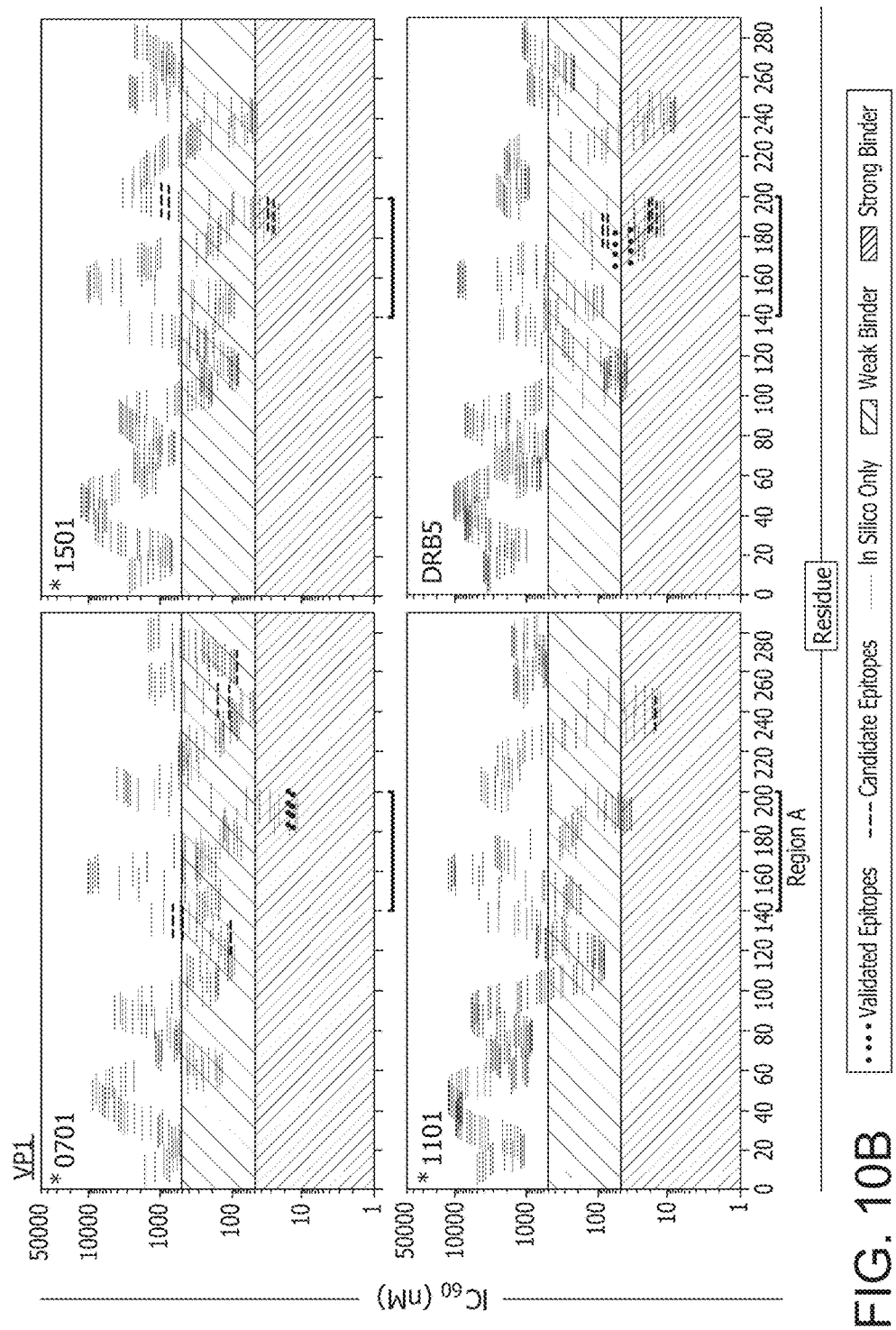
Figure 10C:
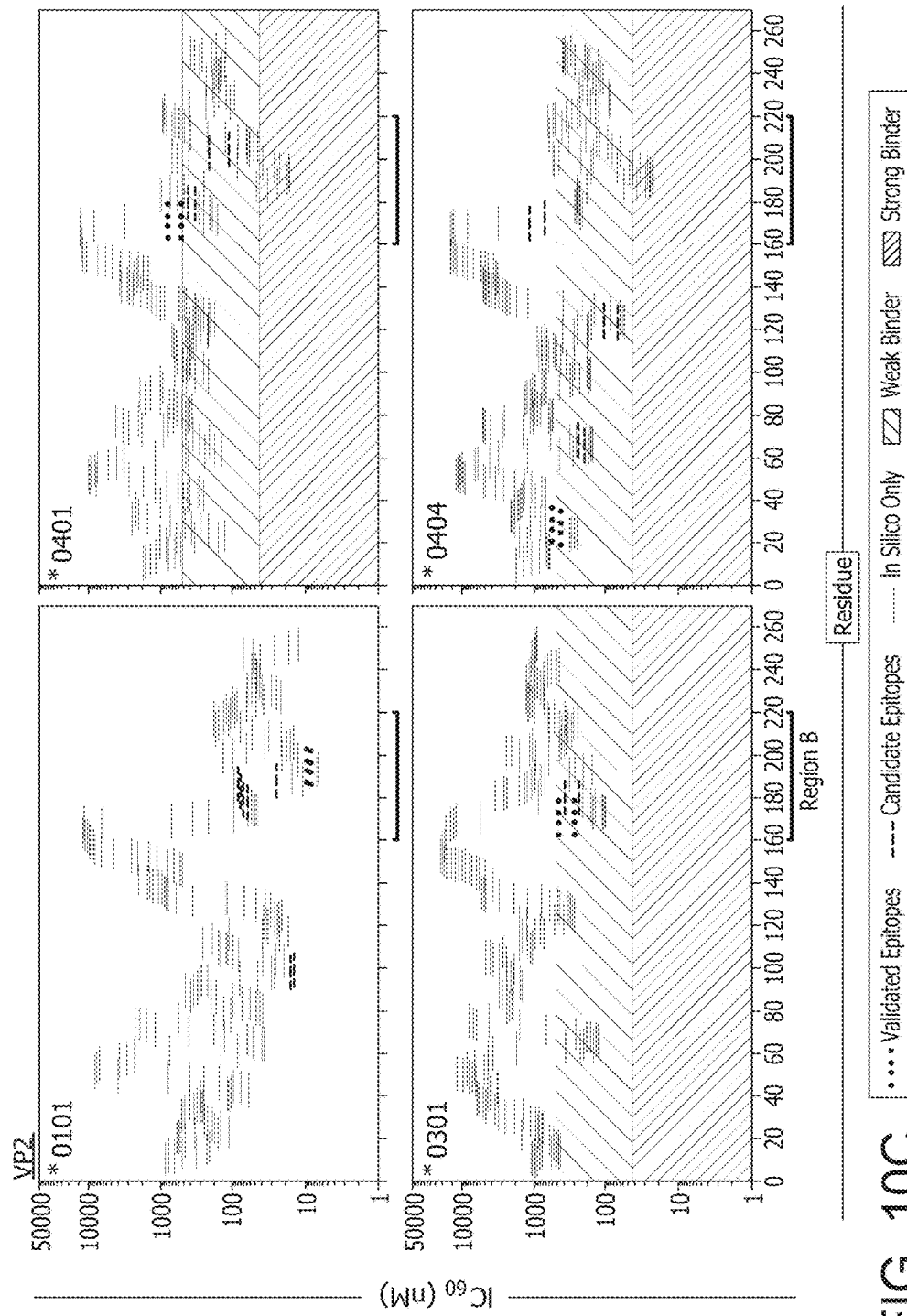
Figure 10D:
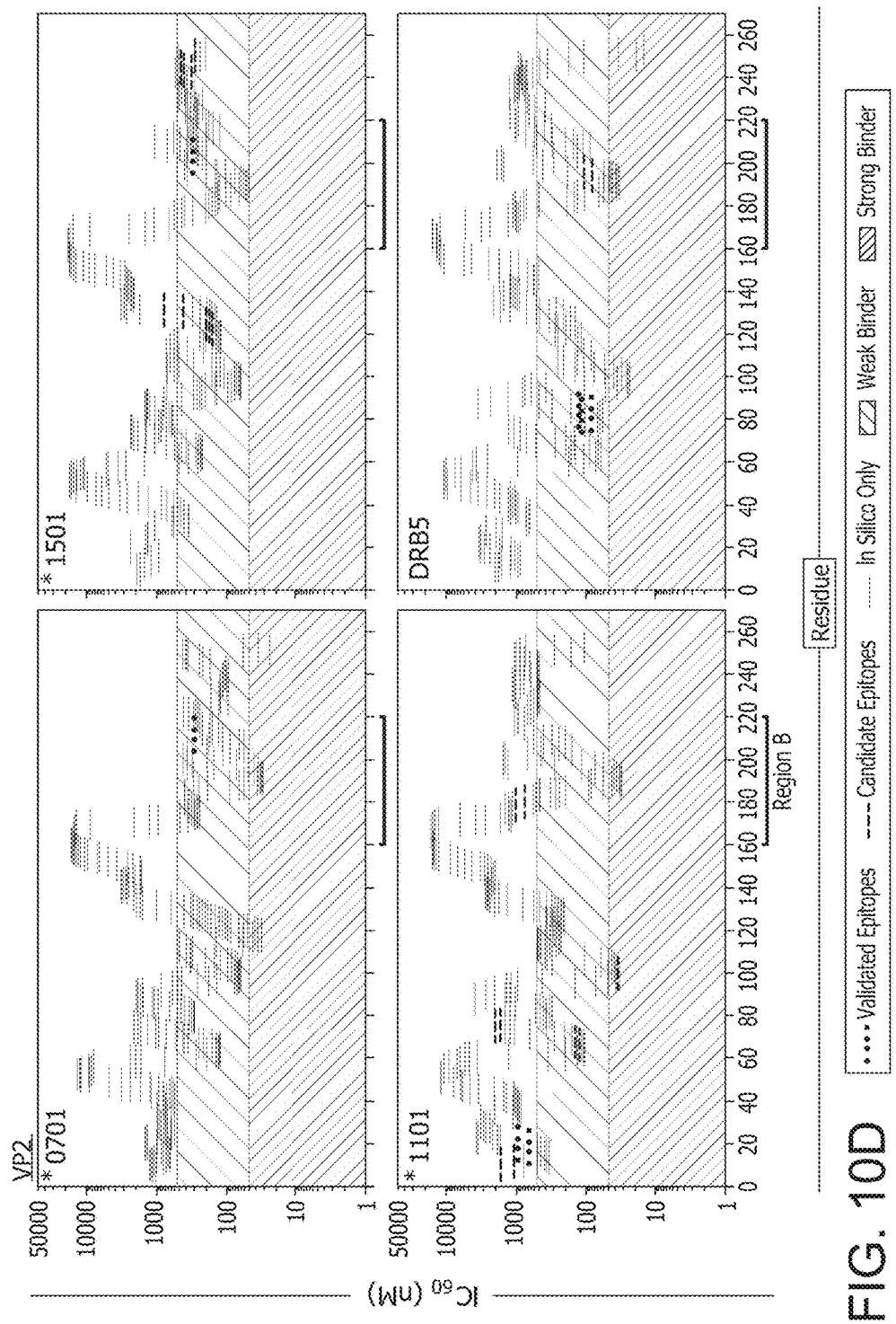
Figure 11:
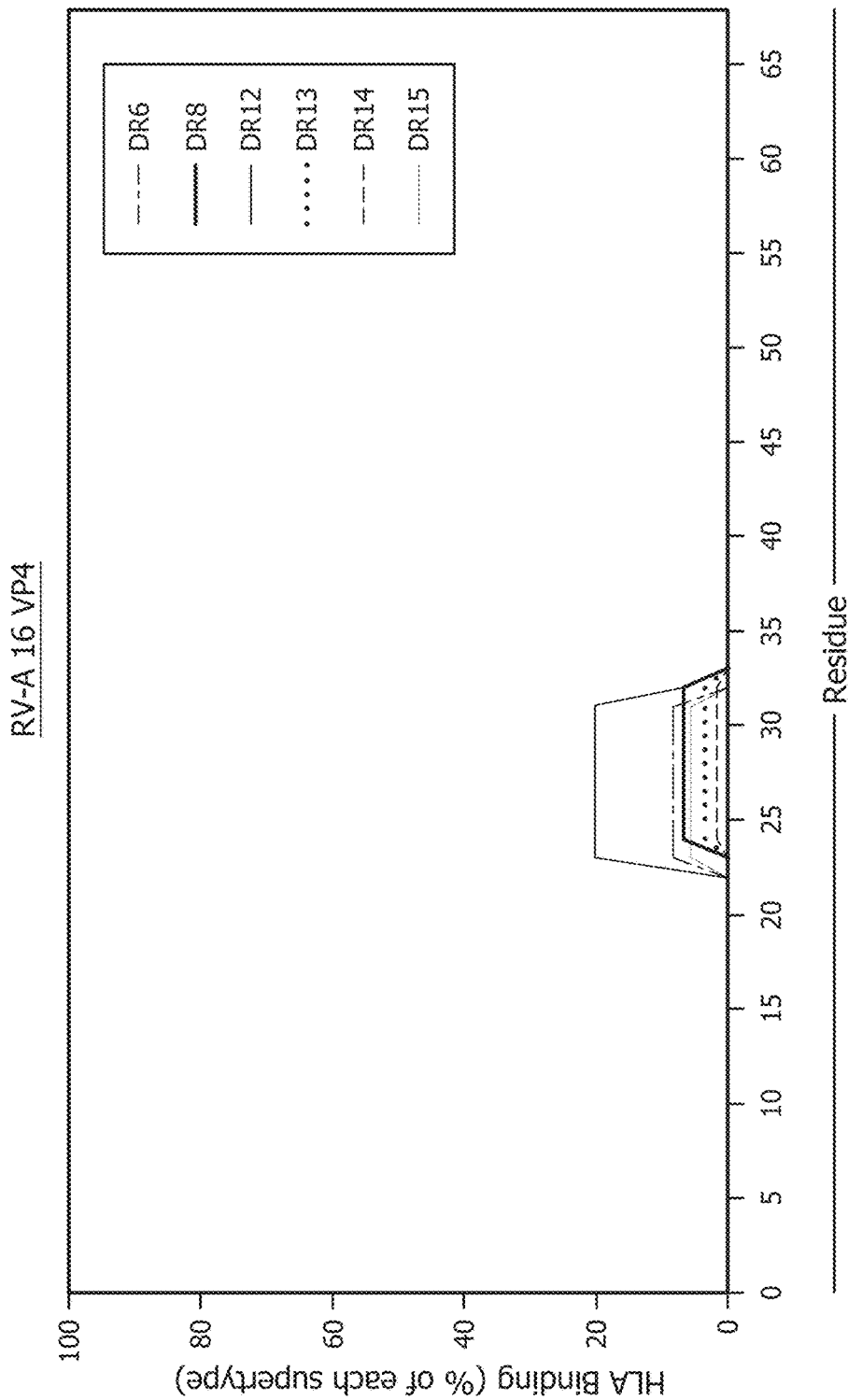
Figure 12A:
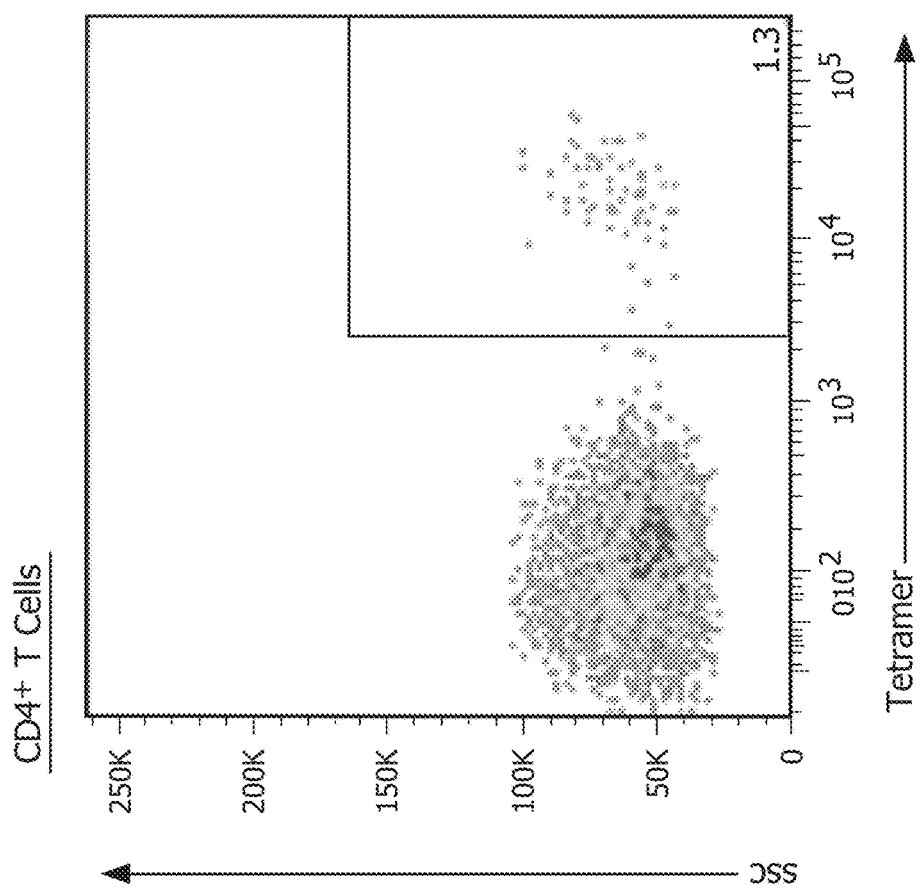
Figure 12B:
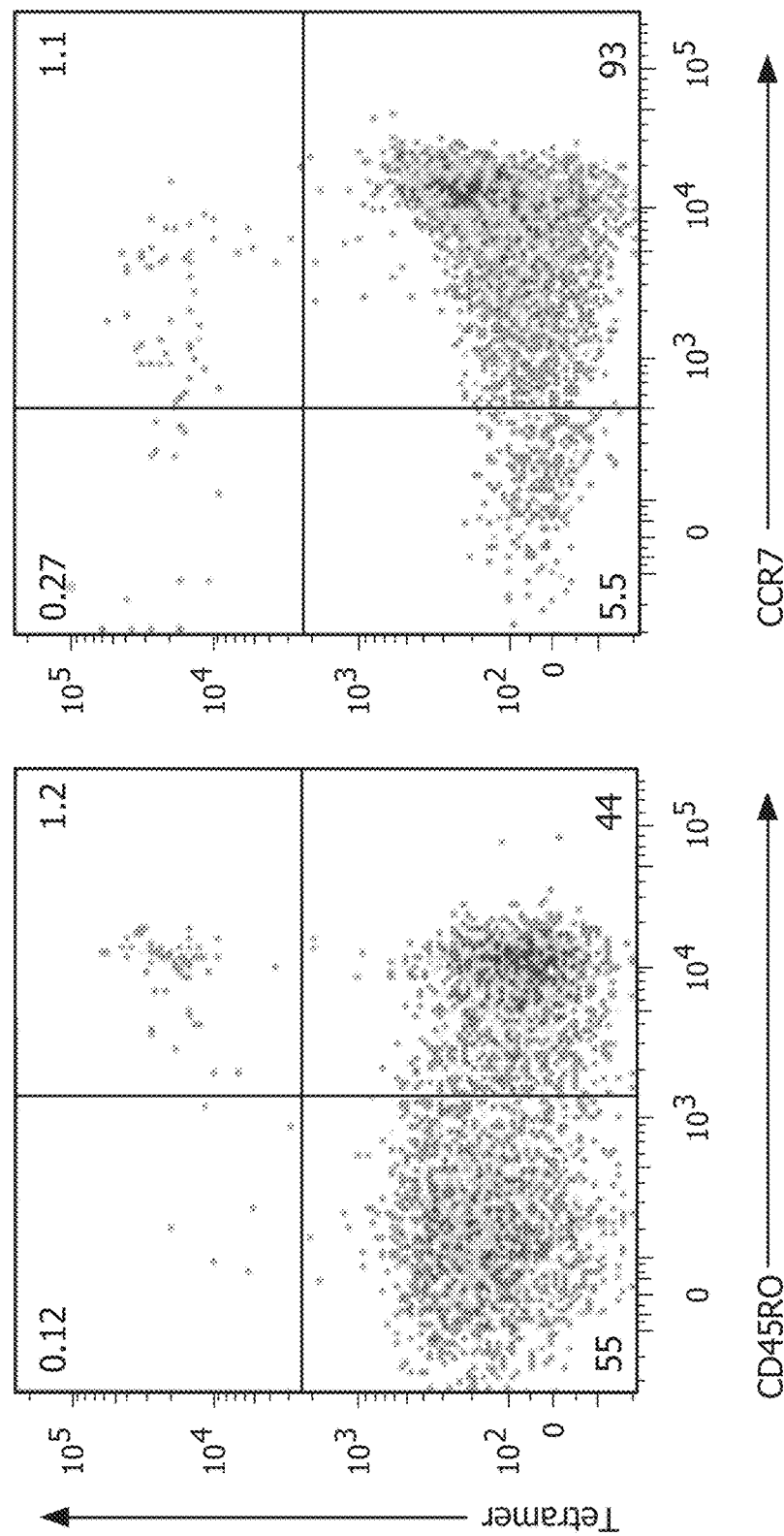
Figure 12E:
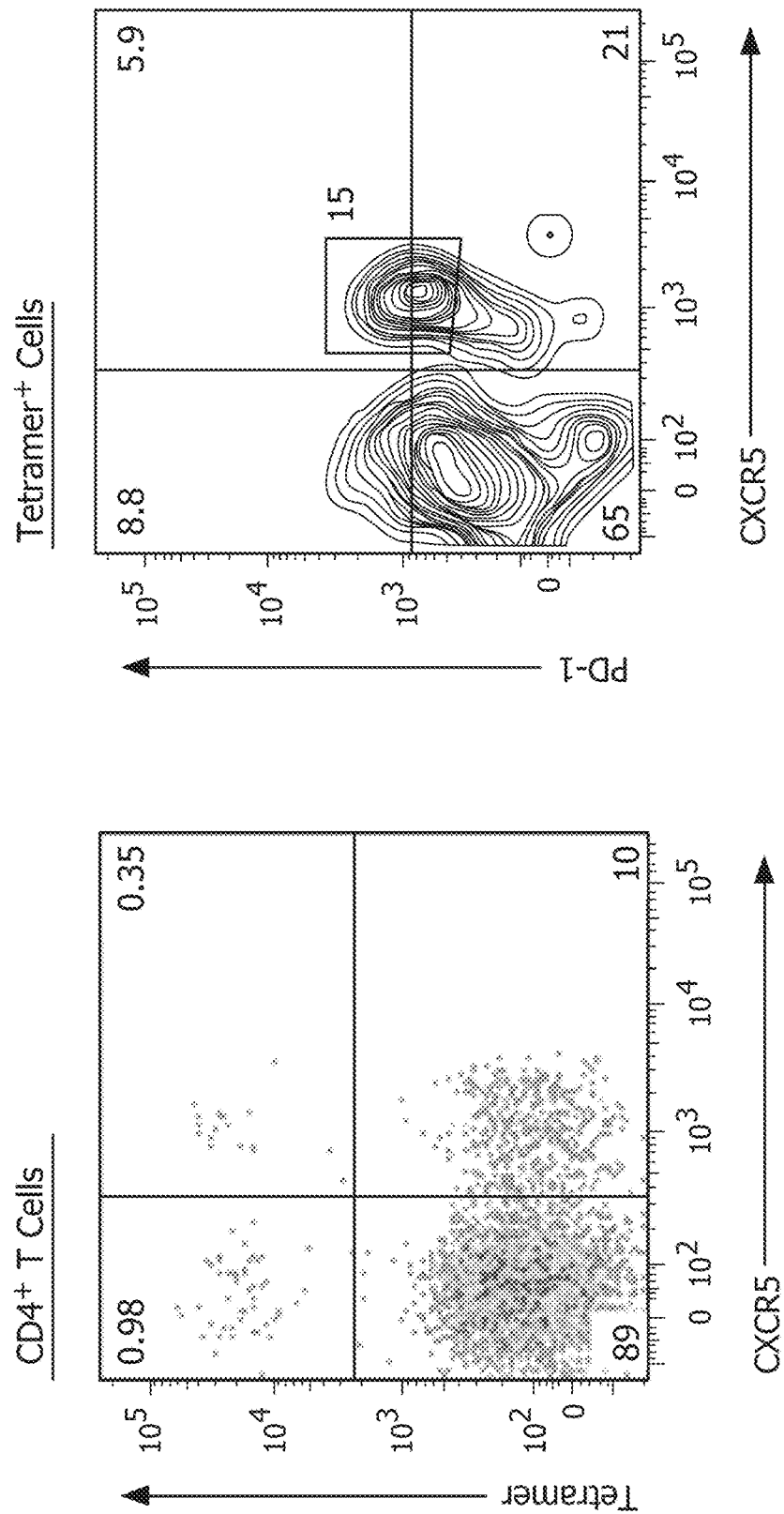
Figure 13:
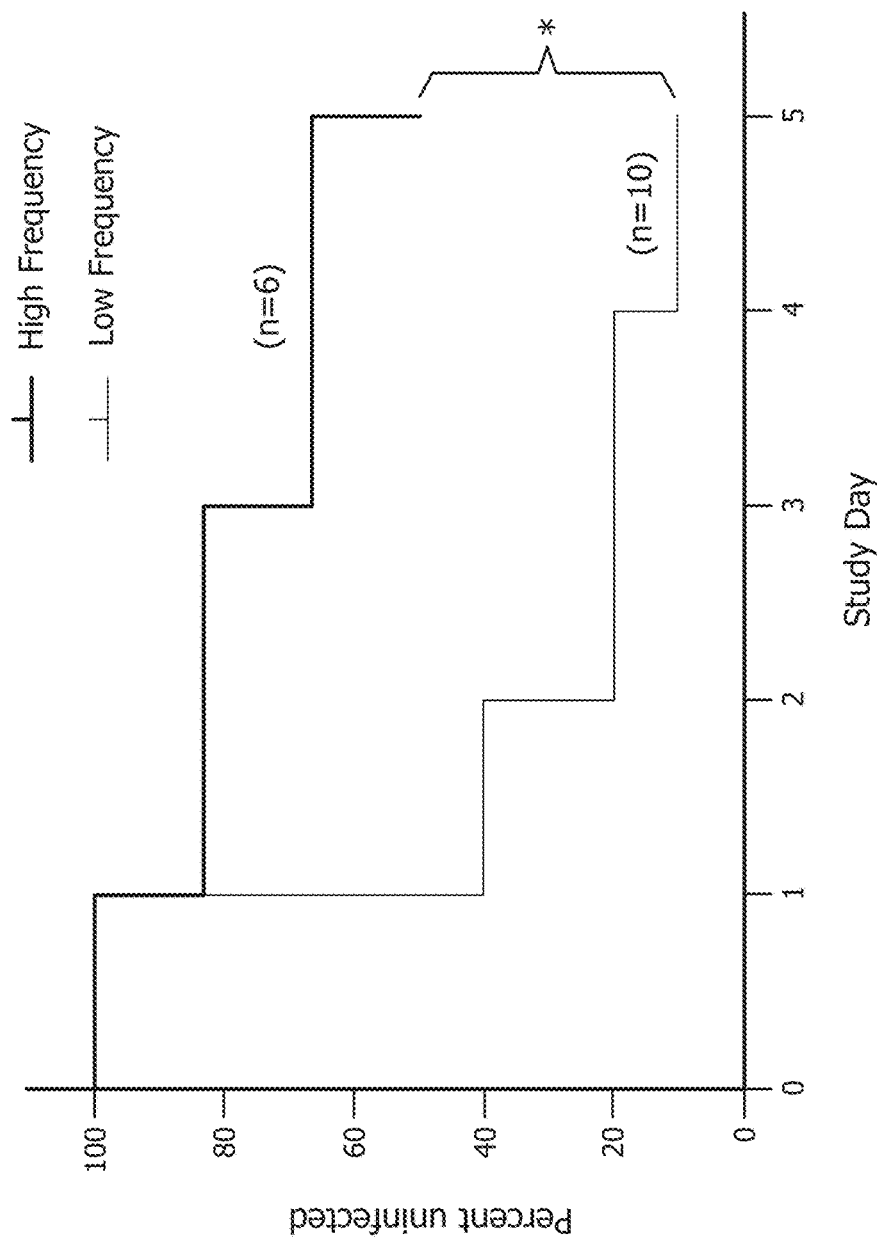
Figure 14:
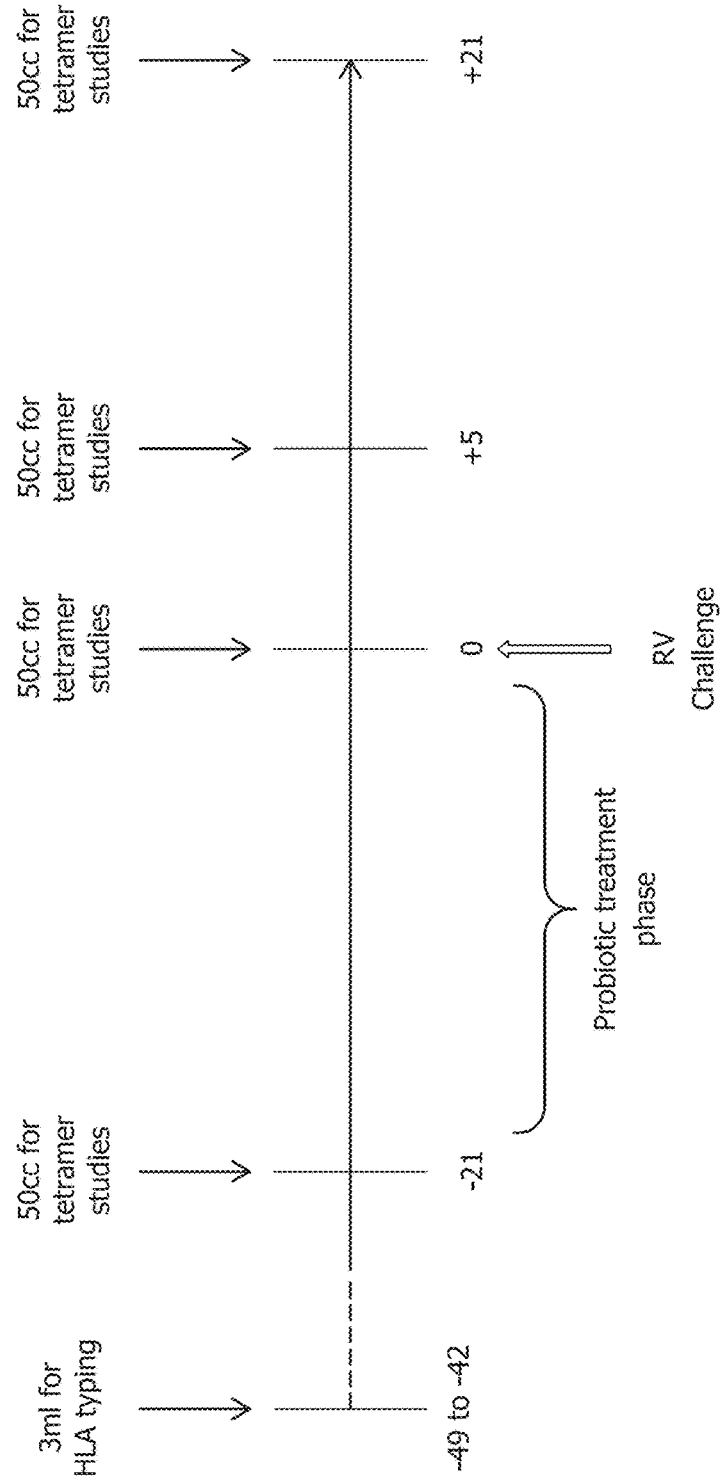

Finally, we sought to test whether epitope-specific T cells were responsive to corresponding epitopes of a different RV strain. As a first step, we used TGEM to identify T-cell epitopes of RV-A39, a group A virus that is serologically distinct from RV-A16. Epitope mapping using DRB1*0401 tetramers yielded 2 epitopes, including one (designated VP2169-188) that contained a predicted core corresponding to the RV-A16 *0401-restricted epitope, VP2P24 (Table 3). By contrast, there was no RV-A16 counterpart for the other RV-A39 epitope (FIG. 6A). RV-A39-specific T cells were detectable at frequencies similar to RV-A16-specific T cells (8 to 24 per million CD4+ T cells). These cells displayed a central memory signature (CD45RO+CCR7+) in seronegative subjects, and included a mixture of T effector (CXCR5neg) and Tfh (CXCR5+PD-1lo) cells, akin to RV-A16-specific T cells (FIG. S6). Stimulating cells from HLA-DR*0401+ subjects with RV-A39 VP2169-188 induced expansion of both RV-A16- and RV-A39-specific T-cells recognizing corresponding epitopes that contained altered peptide flanking regions (FIGS. 6A-C). Expanded RV-specific T cells comprised a major IFN-γ+IL-4neg population, and minor populations expressing IL-17A and IL-21, indicating the presence of Th1, Th17 and Tfh subsets (FIGS. 6D & E). Together, these findings provide proof-of-concept that RV-A16-specific T cells recognizing conserved RV epitopes can respond to cross-reactive determinants of different RV strains.

Table S1 demonstrates peptides containing candidate epitopes of RV-A16 VP1 and VP2 capsid proteins. Validated epitopes are shaded. Table S2 demonstrates comparison of sequence identities between full length and core epitopes of selected RV-A16 epitopes and Rhinovirus strains belonging to species A, B and C. Peptides analyzed were those that gave the lowest sequence identity with strains of RV species C. Data was generated based on sequence alignments obtained by Protein BLAST using the top 5,000 results.

See FIGS. 1-12.

Example 1—Discussion

By integrating in vitro and in silico epitope mapping approaches, we have constructed a comprehensive map of CD4+ T-cell epitopes of the capsid proteins VP1 and VP2 of RV-A16. Our strategy allowed the identification of immunologically relevant epitopes in the context of multiple HLA molecules, as well as characterization of CD4+ T cells that target these epitopes. The findings demonstrate that circulating RV-specific memory CD4+ T cells in HLA-diverse subjects recognize a limited set of species-specific and pan-species epitopes, as well as those that are more broadly conserved among other picornavirus family members known to trigger disease exacerbations [70-74]. Our ability to readily identify circulating virus-specific memory T cells in healthy subjects supports the view that these T cells arise from repeated previous infections with homotypic or heterotypic RV strains or related viruses. Epitope-specific T cells responded to RV infection in vivo, and comprised both Th1 effectors and Tfh cells, both of which would be expected to contribute to viral clearance through cytolysis and by providing help to B cells for antibody production [75-77]. We propose that harnessing such attributes by administering peptides in vivo might prove effective for preventing RV infections and their adverse sequelae.

Tetramer guided epitope mapping provides a sensitive and comprehensive approach for identifying T-cell epitopes restricted to a specific HLA molecule [78-80]. Our study design involved several analytical steps including identification of T-cell epitopes in vitro using peptide-stimulated cultures established from subjects with known HLA type, followed by validation by direct ex vivo staining of cells in additional subjects. Our ability to reliably detect RV-specific T cells specific for each of the 10 validated epitopes in the context of 8 HLA-DR molecules provided evidence of immunodominance. This was bolstered by detection of RV-specific T cells targeting the same *0401-restricted epitope in all eleven *0401+ subjects included in our study. A major advantage of our approach as compared with other epitope mapping methods such as Elispot or intracellular cytokine assays is that the epitopes identified by TGEM are proven to bind to specific MHC molecules. In addition, TGEM is highly sensitive based on its ability to detect frequencies as low as 1 in 200,000 CD4+ T cells. This latter point is evidenced by a recent study that used TGEM to detect more than ten *0401-restricted epitopes of GAD65, an autoantigen for type 1 diabetes [78]. Assay sensitivity is critical given the low precursor frequency of antigen-specific T cells in the T-cell repertoire, and their random distribution in tissue culture wells. Thus, less sensitive methods often warrant the use of statistical modeling to confirm immunodominance [81]. Computer prediction of epitopes corresponding to those identified by TGEM further supported the significance of these epitopes.

Interestingly, no T-cell epitopes of the small capsid protein, VP4, were identified, and this was borne out by in silico analyses. VP4 resides on the internal aspect of the capsid and is highly conserved [82]. It is possible that low numbers of VP4-specific CD4+ T cells exist in healthy subjects that fall below the level of detection in our system. Alternatively, VP4-specific T cells may recognize epitopes presented in the context of HLA-DQ or -DP. However, such cells usually exist at much lower frequencies in the periphery compared with DR-restricted T cells [83,84]. A more extensive analysis of other viral proteins, including VP3, as well as functional proteins, might provide further insight into the relative contributions of CD4+ T-cell epitopes that target different RV components. Nonetheless, failure to detect VP4 T-cell epitopes lends credence to VP1 and VP2 as immunogenic antigens that promote durable CD4+ T-cell responses.

It has been known for decades that serum neutralizing antibodies induced by RV infection protect against reinfection with the same strain [12-15]. However, attempts to develop cross-protective antibody-based vaccines have been disappointing owing to the high degree of antigenic variability among the numerous existing RV serotypes [18]. By contrast, recent work in mice immunized with conserved capsid protein antigens has provided proof-of-concept for the capacity to induce cross-reactive immune responses driven by CD4+ T cells [30]. There are several lines of evidence to support a protective role for CD4+ T cells in RV infection in humans. For example, RV-specific CD4+ T-cell clones produce IFN-γ and proliferate in response to stimulation with multiple RV serotypes [85,86]. Moreover, higher proliferation and IFN-γ responses prior to RV infection appear to be protective based on their link to reduced viral shedding after inoculation [22]. These observations were echoed in more recent work in an influenza challenge model, wherein higher T-cell frequencies existing in seronegative subjects prior to infection were protective [21]. In the present study, we identified a Th1 signature in RV-specific T cells that exist prior to infection, coupled with mobilization and expansion of memory cells during the effector phase of infection. Together, these lines of evidence support an antiviral role for pre-existing CD4+ T cells that initiates prior to the induction of neutralizing antibodies. This process could involve multiple effector T-cell types and diverse mechanisms that are poorly understood [87]. Further elucidation of the complexity and function of RV-specific CD4+ T cells, and their relationship to clinical and immune outcomes following infection, is warranted. Though the numbers of steady state T cells were variable in our study, frequencies >30 cells per million CD4+ T cells were identified for 6 of the 12 tetramers tested. The observed T-cell frequencies were well within the range of those reported using MHCII tetramers for other viral epitopes in the absence of current exposure, including those present several years after vaccination [61,79]. Given that TGEM preferentially selects for T-cell epitope specificities that exist at the highest frequencies, our results imply selective persistence of T cells directed against conserved epitopes. This might seem logical, given that frequent infections with heterotypic RV strains could result in iterative priming of specific memory T cells by epitopes conserved across different RV types. In line with this theory, we identified VP2-specific T cells with the same HLA restriction (*0401) that recognized epitopes of RV-A16 and RV-A39 sharing a common predicted core epitope. This observation was significant given that each epitope was identified in separate TGEM experiments using different peptide libraries corresponding to the two RV strains. Further tests provided proof-of-concept for functional cross-protection between Th1 and Tfh cells that targeted core epitopes shared between different RV strains. The fact that TGEM of RV-A16 VP1 did not identify an *0401-restricted epitope corresponding to that identified for RV-A39 is likely explained by a single amino acid substitution within the predicted core.

Sequence alignments confirmed that the degree of conservation of RV-A16 epitopes varied by species, with the highest identity among RV-A, and the lowest among RV-C. For species A, most of the sequence variability resided in flanking residues that were not critical for HLA binding. Moreover, high sequence identities were evident between RV-A and -C for select epitopes, indicating the potential for broad cross-protection. Further analysis revealed positioning of T-cell epitopes within structural determinants involved in interactions with ICAM-1, and possibly in capsid protein assembly. These features not only provide a structural basis for the conservation of these epitopes, but may also explain the species specificity of VP1 epitopes.

In order to achieve protective efficacy, an RV peptide vaccine should not only guard against multiple RV strains, but also provide broad coverage of the general population. Using TGEM, we verified the existence of CD4+ T cells specific for conserved RV epitopes in HLA diverse subjects representing ~80% of the general population. These epitopes bound to multiple HLA molecules, and primarily clustered into HLA binding "hotspots" within VP1 and VP2, each comprising a narrow span of 60 amino acids. This suggests that relatively few candidate peptides might suffice for the purposes of vaccine design, a theory supported by our population coverage analyses. Furthermore, predicted binding to a broad array of class I HLA supertypes within these regions would be expected to confer the advantage of orchestrating CD8+ T-cell responses in parallel with CD4+ T cell-mediated immunity [88-91].

Using a variety of in silico approaches to interrogate epitopes identified by TGEM, we provided further evidence to support their immunogenic potential. In general, there was a high level of agreement among different in silico methods. Importantly, our study highlighted the limitations of bioinformatic approaches for 9mer-based algorithms to predict those CD4+ T-cell epitopes identified by TGEM. This was evidenced by the reduced ability to predict epitopes corresponding to TGEM epitopes using 9mer as opposed to 15- or 19mer prediction algorithms, and supports the contribution of flanking amino acids to peptide binding to class II molecules. This aspect highlights peptide length as an important consideration in vaccine design. Though we have demonstrated that a single peptide can expand T cells with a different RV strain specificity, despite variations in flanking residues, further work is necessary to assess the full impact of subtle changes in amino acid sequence on the degree of cross-reactivity.

From a clinical perspective, it will be important to consider whether RV epitopes administered to individuals with chronic lung disease might hold the potential to protect against the adverse sequelae of RV infection. Numerous theories abound regarding how T-cell-driven inflammation contributes to the pathogenesis of RV infection in these subjects. These include interference of Th1 immunity, or else exaggeration of the Th2 response [92-97]. It is tempting to speculate that interventions designed to boost cross-reactive virus-specific Th1/Tfh cells in at-risk populations prior to exposure could prove beneficial in preventing RV infection. Further studies in this area are clearly warranted, given the enormous burden imposed by RV infection on society.

Example 2—RV-A39 Studies

Results:

All Tables can be found after the Bibliography (before the Claims).

Table 4 demonstrates the relationship of RV-Specific $CD4^+$ T cell precursor frequency to infection status in DR*0401+ subjects undergoing experimental challenge. the numbers of HLA-DR*0401+ subjects with "high" versus "low" T-cell numbers who were infected with RV-39 following experimental challenge with RV-39.

FIG. 12 demonstrates that circulating RV-A39-specific $CD4^+$ T cells display a central memory phenotype.

FIG. 13 demonstrates the cumulative proportion of subjects shedding RV in nasal secretions by the number of days post-inoculation with RV-39.

FIG. 14 provides a schedule for drawing blood in tetramer studies.

Time to RV shedding (days) is summarized for all RV inoculated subjects, and for those who were infected in FIGS. 15A-B, respectively. The red line is the Kaplan Meier curve for those individuals who had RV specific $CD4^+$ T cell precursor frequencies >10 cells per $10^6$ $CD4^+$ T cells, while the black line is the Kaplan Meier curve for those individuals who had RV specific CD4+ T cell precursor frequencies ≤10 cells per 106 $CD4^+$ T cells. The log-rank chi-square statistic for the comparison of the two Kaplan Meier curves in FIG. 15A was 4.2 (P=0.039), while the log-rank chi-square statistic for the comparison of the two Kaplan Meier curves in FIG. 15B was 2.10 (P=0.151).

After accounting for how subjects were treated (versus control), the hazard ratio was 0.317 [95% CI: 0.073, 1.380], P=0.126) for comparing the time to first RV shedding between all RV inoculated individuals who had RV specific $CD4^+$ T cell precursor frequencies >10 cells per $10^6$ $CD4^+$ T cells and all RV inoculated individuals who had RV specific $CD4^+$ T cell precursor frequencies ≤10 cells per $10^6$ $CD4^+$ T cells (Table 5a). After accounting for how subjects were treated (versus control), the hazard ratio was 0.289 [95% CI: 0.049, 1.699], P=0.170) for comparing the time to first RV shedding between all RV infected individuals who had RV specific $CD4^+$ T cell precursor frequencies >10 cells per $10^6$ $CD4^+$ T cells and all RV infected individuals who had RV specific $CD4^+$ T cell precursor frequencies ≤10 cells per $10^6$ $CD4^+$ T cells (Table 5b).

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Louie J K, Yagi S, Nelson F A, Kiang D, Glaser C A, Rosenberg J, et al. Rhinovirus outbreak in a long term care facility for elderly persons associated with unusually high mortality. Clin Infect Dis. 2005; 41(2) 262-5.
2. Calhoun W J, Dick E C, Schwartz L B, Busse W W. A common cold virus, rhinovirus 16, potentiates airway inflammation after segmental antigen bronchoprovocation in allergic subjects. J Clin Invest. 1994; 94(6) 2200-8.
3. Gem J E, Calhoun W, Swenson C, Shen G, Busse W W. Rhinovirus infection preferentially increases lower airway responsiveness in allergic subjects. Am J Respir Crit Care Med. 1997; 155(6) 1872-6.
4. Heymann P W, Kennedy J L. Rhinovirus-induced asthma exacerbations during childhood: the importance of understanding the atopic status of the host. J Allergy Clin Immunol. 2012; 130(6) 1315-6.
5. Cox D W, Bizzintino J, Ferrari G, Khoo S K, Zhang G, Whelan S, et al. HRV-C Infection in Young Children with Acute Wheeze is Associated with Increased Acute Respiratory Hospital Admissions. Am J Respir Crit Care Med. 2013; 188(11) 1358-64.
6. Iwane M K, Prill M M, Lu X, Miller E K, Edwards K M, Hall C B, et al. Human Rhinovirus Species Associated With Hospitalizations for Acute Respiratory Illness in Young U S Children. J Infect Dis. 2011; 204(11) 1702-10.
7. Lemanske R F, Jackson D J, Gangnon R E, Evans M D, Li Z, Shult P A, et al. Rhinovirus illnesses during infancy predict subsequent childhood wheezing. J Allergy Clin Immunol. 2005; 116(3) 571-7.
8. O'Callaghan-Gordo C, Bassat Q, Diez-Padrisa N, Morais L, Machevo S, Nhampossa T, et al. Lower Respiratory Tract Infections Associated with Rhinovirus during Infancy and Increased Risk of Wheezing during Childhood. A Cohort Study. PLoS One. 2013; 8(7) e69370.
9. Asthma's Impact on the Nation: Data from the CDC National Asthma Control Program [Internet]. 2010. Available from a CDS Asthma website.
10. Heikkinen T, Jirvinen A. The common cold. Lancet. 2003; 361(9351) 51-9.
11. Nicholson K G, Kent J, Hammersley V, Cancio E. Acute viral infections of upper respiratory tract in elderly people living in the community: comparative, prospective, population based study of disease burden. BMJ. 1997; 315 (7115) 1060-4.
12. Alper C M, Doyle W J, Skoner D P, Buchman C A, Seroky J T, Gwaltney J M, et al. Prechallenge antibodies: moderators of infection rate, signs, and symptoms in adults experimentally challenged with rhinovirus type 39. Laryngoscope. 1996; 106(10) 1298-305.
13. Alper C M, Doyle W J, Skoner D P, Buchman C A, Cohen S, Gwaltney J M. Prechallenge Antibodies Moderate Disease Expression in Adults Experimentally Exposed to Rhinovirus Strain Hanks. Clin Infect Dis. 1998; 27 119-28.
14. Cate T R, Rossen R D, Douglas Jr R G, Butler W T, Couch R B. The role of nasal secretion and serum antibody in the rhinovirus common cold. Am J Epidemiol. 1966; 84(2) 352-63.
15. Cate T R, Couch R B, Johnson K M. Studies With Rhinoviruses in Volunteers: Production of Illness, Effect of Naturally Acquired Antibody, and Demonstration of a Protective Effect Not Associated With Serum Antibody. J Clin Invest. 1964; 43(1) 56-67.
16. Barclay W S, Al-Nakib W, Higgins P G, Tyrrell D A. The time course of the humoral immune response to rhinovirus infection. Epidemiol Infect. 1989; 103(3) 659-69.
17. Conant R M, Vincent N D. Rhinoviruses: Basis for a numbering system I. HeLa cells for propagation and serologic Procedures. J Immunol. 1968; 100(1) 107-13.
18. Palmenberg A C, Spiro D, Kuzmickas R, Wang S, Djikeng A, Rathe J A, et al. Sequencing and analyses of all known human rhinovirus genomes reveal structure and evolution. Science. 2009; 324(5923) 55-9.
19. Hogan R J, Zhong W, Usherwood E J, Cookenham T, Roberts A D, Woodland D L. Protection from respiratory virus infections can be mediated by antigen-specific CD4+ T cells that persist in the lungs. J Exp Med. 2001; 193(8) 981-6.
20. Ge X, Tan V, Bollyky P L, Standifer N E, James E A, Kwok W W. Assessment of seasonal influenza A virus-specific CD4 T-cell responses to 2009 pandemic H1N1 swine-origin influenza A virus. J Virol. 2010; 84(7) 3312-9.
21. Wilkinson T M, Li C K F, Chui C S C, Huang A K Y, Perkins M, Liebner J C, et al. Preexisting influenza-specific CD4+ T cells correlate with disease protection against influenza challenge in humans. Nat Med. 2012; 18(2) 274-80.
22. Parry D E, Busse W W, Sukow K A, Dick C R, Swenson C, Gern J E. Rhinovirus-induced PBMC responses and outcome of experimental infection in allergic subjects. J Allergy Clin Immunol. 2000; 105(4) 692-8.
23. Colonno R J, Condra J H, Mizutani S, Callahan P L, Davies M E, Murcko M A. Evidence for the direct involvement of the rhinovirus canyon in receptor binding. Proc Natl Acad Sci USA. 1988; 85(15) 5449-53.
24. Olson N H, Kolatkar P R, Oliveira M a, Cheng R H, Greve J M, McClelland A, et al. Structure of a human rhinovirus complexed with its receptor molecule. Proc Natl Acad Sci USA. 1993; 90(2) 507-11.
25. Bella J, Rossmann M G. ICAM-1 receptors and cold viruses. Pharm Acta Helv. 2000; 74 291-7.
26. Iwasaki J, Smith W-A, Khoo S-K, Bizzintino J, Zhang G, Cox D W, et al. Comparison of rhinovirus antibody titers in children with asthma exacerbations and species-specific rhinovirus infection. J Allergy Clin Immunol. 2014; 134(1) 25-32.
27. McLean G R, Walton R P, Shetty S, Peel T J, Paktiawal N, Kebadze T, et al. Rhinovirus infections and immunisation induce cross-serotype reactive antibodies to VP1. Antiviral Res. 2012; 95(3) 193-201.
28. Niespodziana K, Cabauatan C R, Jackson D J, Gallerano D, Trujillo-Torralbo B, del Rosario A, et al. Rhinovirus-induced VP1-specific Antibodies are Group-specific and Associated With Severity of Respiratory Symptoms. EBioMedicine. 2015; 2(1) 64-70.
29. Iwasaki J, Smith W-A, Stone S R, Thomas W R, Hales B J. Species-specific and cross-reactive IgG1 antibody binding to viral capsid protein 1 (VP1) antigens of human rhinovirus species A, B and C. PLoS One. 2013; 8(8) e70552.
30. Glanville N, McLean G R, Guy B, Lecouturier V, Berry C, Girerd Y, et al. Cross-serotype immunity induced by immunization with a conserved rhinovirus capsid protein. PLOS Pathog. 2013; 9(9) e1003669.
31. Kennedy J L, Shaker M, McMeen V, Gem J, Carper H, Murphy D, et al. Comparison of Viral Load in Individuals with and without Asthma during Infections with Rhinovirus. Am J Respir Crit Care Med. 2014; 189(5) 532-9.
32. Hewson C A, Haas J J, Bartlett N W, Message S D, Laza-Stanca V, Kebadze T, et al. Rhinovirus induces MUC5AC in a human infection model and in vitro via NF-KB and EGFR pathways. Eur Respir J. 2010; 36(6) 1425-35.
33. Grünberg K, Smits H H, Timmers M C, de Klerk E P, Dolhain R J, Dick E C, et al. Experimental rhinovirus 16 infection. Effects on cell differentials and soluble markers in sputum in asthmatic subjects. Am J Respir Crit Care Med. 1997; 156 609-16.
34. Bizzintino J, Lee W M, Laing I A, Vang F, Pappas T, Zhang G, et al. Association between human rhinovirus C and severity of acute asthma in children. Eur Respir J. 2011; 37(5) 1037-42.
35. Calvdn J, Yudina Y, Hallgren O, Westergren-Thorsson G, Davies D E, Brandelius A, et al. Viral stimuli trigger exaggerated thymic stromal lymphopoietin expression by chronic obstructive pulmonary disease epithelium: role of endosomal TLR3 and cytosolic RIG-I-like helicases. J Innate Immun. 2012; 4 86-99.
36. Liu K, Gualano R C, Hibbs M L, Anderson G P, Bozinovski S. Epidermal growth factor receptor signaling to Erk1/2 and STATs control the intensity of the epithelial inflammatory responses to rhinovirus infection. J Biol Chem. 2008; 283(15) 9977-85.

37. Zambrano J C, Carper H T, Rakes G P, Patrie J T, Murphy D D, Platts-Mills T A E, et al. Experimental rhinovirus challenges in adults with mild asthma: Response to infection in relation to IgE. J Allergy Clin Immunol. 2003; 111(5) 1008-16.

38. Turner R B, Weingand K W, Yeh C H, Leedy D W. Association between interleukin-8 concentration in nasal secretions and severity of symptoms of experimental rhinovirus colds. Clin Infect Dis. 1998; 26(4) 840-6.

39. Reefer A J, Carneiro R M, Custis N J, Platts-Mills T a E, Sung S-S J, Hammer J, et al. A role for IL-10-mediated HLA-DR7-restricted T cell-dependent events in development of the modified Th2 response to cat allergen. J Immunol. 2004; 172(5) 2763-72.

40. Reijonen H, Kwok W W. Use of HLA class II tetramers in tracking antigen-specific T cells and mapping T-cell epitopes. Methods. 2003; 29(3) 282-8.

41. The Uniprot Consortium. Activities at the Universal Protein Resource (UniProt). Nucleic Acids Res. 2014; 42 D191-8.

42. Novak E J, Liu A W, Gebe J A, Falk B A, Nepom G T, Koelle D M, et al. Tetramer-guided epitope mapping: Rapid identification and characterization of immunodominant CD4+ T cell epitopes from complex antigens. J Immunol. 2001; 166(11) 6665-70.

43. Kwok W W, Roti M, DeLong J H, Tan V, Wambre E, James E A, et al. Direct ex vivo analysis of allergen-specific CD4+ T cells. J Allergy Clin Immunol. 2010; 125(6) 1407-9.

44. Danke N A, Koelle D M, Yee C, Beheray S, Kwok W W. Autoreactive T cells in healthy individuals. J Immunol. 2004; 172(10) 5967-72.

45. Hulse K E, Reefer A J, Engelhard V H, Patrie J T, Ziegler S F, Chapman M D, et al. Targeting Allergen to FcgammaRI Reveals a Novel Th2 Regulatory Pathway Linked to TSLP Receptor. J Allergy Clin Immunol. 2010; 125(1) 247-64.

46. Roederer M, Nozzi J L, Nason M C. SPICE: exploration and analysis of post-cytometric complex multivariate datasets. Cytometry A. 2011; 79(2) 167-74.

47. Altschul S F, Gish W, Miller W, Myers E W, Lipman D J. Basic Local Alignment Search Tool. J Mol Biol. 1990; 215 403-10.

48. Waterhouse A M, Procter J B, Martin D M A, Clamp M, Barton G J. Jalview Version 2—a multiple sequence alignment editor and analysis workbench. Bioinformatics. 2009; 25(9) 1189-91.

49. Wang P, Sidney J, Kim Y, Sette A, Lund O, Nielsen M, et al. Peptide binding predictions for HLA DR, DP and DQ molecules. BMC Bioinformatics. 2010; 11 568.

50. Wang P, Sidney J, Dow C, Mothé B, Sette A, Peters B. A systematic assessment of MHC class II peptide binding predictions and evaluation of a consensus approach. PLOS Comput Biol. 2008; 4(4) e1000048.

51. Nielsen M, Lundegaard C, Lund O. Prediction of MHC class II binding affinity using SMM-align, a novel stabilization matrix alignment method. BMC Bioinformatics. 2007; 8 238.

52. Nielsen M, Lund O. N N-align. An artificial neural network-based alignment algorithm for MHC class II peptide binding prediction. BMC Bioinformatics. 2009; 10 296.

53. Sturniolo T, Bono E, Ding J, Raddrizzani L, Tuereci O, Sahin U, et al. Generation of tissue-specific and promiscuous HLA ligand databases using DNA microarrays and virtual HLA class II matrices. Nat Biotechnol. 1999; 17(6) 555-61.

54. Zhang G L, DeLuca D S, Keskin D B, Chitkushev L, Zlateva T, Lund O, et al. MULTIPRED2: a computational system for large-scale identification of peptides predicted to bind to HLA supertypes and alleles. J Immunol Methods. 2011; 374 53-61.

55. Karosiene E, Rasmussen M, Blicher T, Lund O, Buus S, Nielsen M. NetMHCIIpan-3.0, a common pan-specific MHC class II prediction method including all three human MHC class II isotypes, HLA-DR, HLA-DP and HLA-DQ. Immunogenetics. 2013; 65(10) 711-24.

56. Nielsen M, Lundegaard C, Blicher T, Lamberth K, Harndahl M, Justesen S, et al. NetMHCpan, a method for quantitative predictions of peptide binding to any HLA-A and -B locus protein of known sequence. PLoS One. 2007; 2(8) e796.

57. Hoof I, Peters B, Sidney J, Pedersen L E, Sette A, Lund O, et al. NetMHCpan, a method for MHC class I binding prediction beyond humans. Immunogenetics. 2009; 61(1) 1-13.

58. Bui H-H, Sidney J, Dinh K, Southwood S, Newman M J, Sette A. Predicting population coverage of T-cell epitope-based diagnostics and vaccines. BMC Bioinformatics. 2006; 7 153.

59. DeLano W. The PyMOL Molecular Graphics System. San Carlos, Calif.: DeLano Scientific; 2002.

60. Hadfield A T, Lee W M, Zhao R, Oliveira M A, Minor I, Rueckert R R, et al. The refined structure of human rhinovirus 16 at 2.15 A resolution: Implications for the viral life cycle. Structure. 1997; 5(3) 427-41.

61. Su L F, Kidd B A, Han A, Kotzin J J, Davis M M. Virus-specific CD4+ memory-phenotype T cells are abundant in unexposed adults. Immunity. 2013; 38(2) 373-83.

62. McIntyre C L, Knowles N J, Simmonds P. Proposals for the classification of human rhinovirus species A, B and C into genotypically assigned types. J Gen Virol. 2013; 94 1791-806.

63. Oliveira M, Zhao R, Lee W, Kremer M. The structure of human rhinovirus 16. Structure. 1993; 1(1) 51-68.

64. Basta H A, Sgro J-Y, Palmenberg A C. Modeling of the human rhinovirus C capsid suggests a novel topography with insights on receptor preference and immunogenicity. Virology. 2014; 448 176-84.

65. Basta H A, Ashraf S, Sgro J Y, Bochkov Y A, Gem J E, Palmenberg A C. Modeling of the human rhinovirus C capsid suggests possible causes for antiviral drug resistance. Virology. 2014; 448 82-90.

66. Hadfield A T, Oliveira M A, Kim K H, Minor I, Kremer M J, Heinz B a, et al. Structural studies on human rhinovirus 14 drug-resistant compensation mutants. J Mol Biol. 1995; 253 61-73.

67. Yamamoto J, Adachi Y, Onoue Y, Adachi Y S, Okabe Y, Itazawa T, et al. Differential expression of the chemokine receptors by the Th1- and Th2-type effector populations within circulating CD4+ T cells. J Leukoc Biol. 2000; 68 568-74.

68. Groom J R, Luster A D. CXCR3 in T Cell Function. Exp Cell Res. 2011; 317(5) 620-31.

69. van Oosterwijk M F, Juwana H, Tesselaar K, van Oers M H J, Eldering E, et al. CD27-CD70 interactions sensitise naive CD4+ T cells for IL-12-induced Th1 cell development. Int Immunol. 2007; 19(6) 713-8.

70. Drews S J, Simmonds K, Usman H R, Yee K, Fathima S, Tipples G, et al. Characterization of Enterovirus Activity, Including That of Enterovirus D68, in Pediatric Patients in Alberta, Canada, in 2014. J Clin Microbiol. 2015; 53(3) 1042-5.
71. Stephenson J. CDC Tracking Enterovirus D-68 Outbreak Causing Severe Respiratory Illness in Children in the Midwest. JAMA. 2014; 312(13) 1290.
72. Renois F, Bouin A, Andreoletti L. Enterovirus 68 in pediatric patients hospitalized for acute airway diseases. J Clin Microbiol. 2013; 51(2) 640-3.
73. Mallia P, Message S D, Gielen V, Contoli M, Gray K, Kebadze T, et al. Experimental rhinovirus infection as a human model of chronic obstructive pulmonary disease exacerbation. Am J Respir Crit Care Med. 2011; 183(6) 734-42.
74. George S, Garcha D, Mackay A, Patel A, Singh R, Sapsford R, et al. Human rhinovirus infection during naturally occurring COPD exacerbations. Eur Respir J. 2014; 44 87-96.
75. Mahon B P, Katrak K, Nomoto A, Macadam A J, Minor P D, Mills K H G. Poliovirus-Specific CD4+ Th1 Clones with Both Cytotoxic and Helper Activity Mediate Protective Humoral Immunity against a Lethal Poliovirus Infection in Transgenic Mice Expressing the Human Poliovirus Receptor. J Exp Med. 1995; 181 1285-92.
76. Morita R, Schmitt N, Bentebibel S-E, Ranganathan R, Bourdery L, Zurawski G, et al. Human blood CXCR5+ CD4+ T cells are counterparts of T follicular cells and contain specific subsets that differentially support antibody secretion. Immunity. 2011; 34 108-21.
77. Crotty S. Follicular helper CD4 T cells (Tfh). Annu Rev Immunol. 2011; 29 621-63.
78. Yang J, James E A, Sanda S, Greenbaum C, Kwok W W. CD4+ T cells recognize diverse epitopes within GAD65: implications for repertoire development and diabetes monitoring. Immunology. 2013; 138(3) 269-79.
79. James E A, LaFond R E, Gates T J, Mai D T, Malhotra U, Kwok W W. Yellow fever vaccination elicits broad functional CD4+ T cell responses that recognize structural and nonstructural proteins. J Virol. 2013; 87(23) 12794-804.
80. James E A, Bui J, Berger D, Huston L, Roti M, Kwok W W. Tetramer-guided epitope mapping reveals broad, individualized repertoires of tetanus toxin-specific CD4+ T cells and suggests HLA-based differences in epitope recognition. Int Immunol. 2007; 19(11) 1291-301.
81. Woodfolk J A, Sung S S, Benjamin D C, Lee J K, Platts-Mills T A E. Distinct human T cell repertoires mediate immediate and delayed-type hypersensitivity to the Trichophyton antigen, Tri r 2. J Immunol. 2000; 165(8) 4379-87.
82. Kistler A L, Webster D R, Rouskin S, Magrini V, Credle J J, Schnurr D P, et al. Genome-wide diversity and selective pressure in the human rhinovirus. Virol J. 2007; 4 40.
83. Yang J, Huston L, Berger D, Danke N a., Liu A W, Disis M L, et al. Expression of HLA-DP0401 molecules for identification of DP0401 restricted antigen specific T cells. J Clin Immunol. 2005; 25(5) 428-36.
84. Ottenhoff T H M, Elferink D G, Hermans J, de Vries R R P. HLA Class II Restriction Repertoire of Antigen-Specific T Cells. I. The Main Restriction Determinants for Antigen Presentation Are Associated with HLA-D/DR and Not with DP and DQ. Hum Immunol. 1985; 13 105-16.
85. Gem J E, Dick E C, Kelly E A, Vrtis R, Klein B. Rhinovirus-specific T cells recognize both shared and serotype-restricted viral epitopes. J Infect Dis. 1997; 175(5) 1108-14.
86. Hastings G Z, Rowlands D J, Francis M J. Proliferative responses of T cells primed against human rhinovirus to other rhinovirus serotypes. J Gen Virol. 1991; 72 2947-52.
87. Swain S L, McKinstry K K, Strutt T M. Expanding roles for CD4+ T cells in immunity to viruses. Nat Rev Immunol. 2012; 12(2) 136-48.
88. Takahashi H, Germain R N, Moss B, Berzofsky J A. An Immunodominant Class I-Restricted Cytotoxic T Lymphocyte Determinant of Human Immunodeficiency Virus Type 1 Induces CD4 Class II-Restricted Help for Itself. J Exp Med. 1990; 171 571-6.
89. Carreno B M, Turner R V, Biddison W E, Coligan J E. Overlapping epitopes that are recognized by CD8+ HLA class I-restricted and CD4+ class II-restricted cytotoxic T lymphocytes are contained within an influenza nucleoprotein peptide. J Immunol. 1992; 148(3) 894-9.
90. Ahlers J D, Takeshita T, Pendleton C D, Berzofsky J A. Enhanced immunogenicity of HIV-1 vaccine construct by modification of the native peptide sequence. Proc Natl Acad Sci USA. 1997; 94 10856-61.
91. Perkins D L, Lai M-Z, Smith J A, Gefter M L. Identical Peptides Recognized by MHC Class I- and Class II-Restricted T Cells. J Exp Med. 1989; 170 279-89.
92. Hammond C, Kurten M, Kennedy J L. Rhinovirus and Asthma: a Storied History of Incompatibility. Curr Allergy Asthma Rep. 2015; 15(2).
93. Bartlett N W, Walton R P, Edwards M R, Aniscenko J, Caramori G, Zhu J, et al. Mouse models of rhinovirus-induced disease and exacerbation of allergic airway inflammation. Nat Med. 2008; 14(2) 199-204.
94. Message S D, Laza-Stanca V, Mallia P, Parker H L, Zhu J, Kebadze T, et al. Rhinovirus-induced lower respiratory illness is increased in asthma and related to virus load and Th1/2 cytokine and IL-10 production. Proc Natl Acad Sci USA. 2008; 105(36) 13562-7.
95. Papadopoulos N G, Stanciu L A, Papi A, Holgate S T, Johnston S L. A defective type 1 response to rhinovirus in atopic asthma. Thorax. 2002; 57(4) 328-32.
96. Majori M, Corradi M, Caminati A, Cacciani G, Bertacco S, Pesci A. Predominant Th1 cytokine pattern in peripheral blood from subjects with chronic obstructive pulmonary disease. J Allergy Clin Immunol. 1999; 103(3) 458-62.
97. Barnes P J. The cytokine network in asthma and chronic obstructive pulmonary disease. J Clin Invest. 2008; 118 (11) 3546-56.

TABLE 1

RV-A16 Epitopes Identified by TGEM and Their Associated CD4+ T-Cell Frequencies.

| HLA Allele | Epitope and SEQ ID NO: | In Vitro Frequency (% CD4)[1] | Ex Vivo Frequency (# per $10^6$ CD4)[2] | Amino Acid Position |
|---|---|---|---|---|
| 1*0101 | VP1$_{P23}$ PRFSLPFLSIASAYYMFYDG-1 | 8.37, 0.35, 2.37 | 3, 8, 13, 2 | 181-200 |
| | VP2$_{P24}$ PHQFINLRSNNSATLIVPYV-2 | 2.82, 3.17, 11.3 | 17, 148, 26 | 186-205 |

TABLE 1-continued

RV-A16 Epitopes Identified by TGEM and Their Associated CD4+ T-Cell Frequencies.

| HLA Allele | Epitope and SEQ ID NO: | In Vitro Frequency (% CD4)[1] | Ex Vivo Frequency (# per $10^6$ CD4)[2] | Amino Acid Position |
|---|---|---|---|---|
| 1*0301 | $VP2_{P21}$ NEKQPSDDNWLNFDGTLLGN-3 | 1.57, 0.87 | 29, 4, 6 | 162-181 |
| 1*0401 | $VP2_{P21}$ NEKQPSDDNWLNFDGTLLGN-3 | 5.13, 0.89 | 9, 63, 3 | 162-181 |
| 1*0404 | $VP1_{P18}$ HIVMQYMYVPPGAPIPTTRN-4 | 1.84, 4.22, 2.76 | 247, 10, 52, 5 | 141-160 |
|  | $VP2_{P3}$ RGDSTITSQDVANAVVGYGV-5 | 6.86, 1.61 | 36, 1, 38, 5 | 18-37 |
| 1*0701 | $VP1_{P23}$ PRFSLPFLSIASAYYMFYDG-1 | 1.84, 0.74 | 3, 8, 13, 2 | 181-200 |
|  | $VP2_{P26}$ VPYVNAVPMDSMVRHNNWSL-6 | 1.57, 0.84 | 4, 16, 14, 5 | 202-221 |
| 1*1101 | $VP2_{P2}$ SDRIIQITRGDSTITSQDVA-7 | 2.18, 1.22, 2.28 | 8, 11, 15 | 10-29 |
| 1*1501 | $VP2_{P25}$ SNNSATLIVPYVNAVPMDSM-8 | 2.26, 9.02 | 31, 5, 13, 71 | 194-213 |
| DRB5 | $VP1_{P21}$ QSGTNASVFWQHGQPFPRFS-9 | 3.91, 0.95 | 11, 28, 20 | 165-184 |
|  | $VP2_{P10}$ TSKGWWWKLPDALKDMGIFG-10 | 3.93, 4.49, 0.38 | 60, 24, 136 | 74-93 |

[1]Based on percentage of CD4+ T cells that were tetramer-positive in PBMC cultures stimulated with corresponding RV peptides.
[2]Based on tetramer staining of performed directly ex vivo, without culture.

TABLE 2

Sequence Similarity Between RV-A16 Epitopes and Rhinovirus Strains Belonging to Species A, B, and C.

| Epitope and SEQ ID NO: | | Prevalence of Amino Acid Sequence Identity Among Strains of Each Rhinovirus Species | | | | | | | | |
|---|---|---|---|---|---|---|---|---|---|---|
| | | RV A | | | | | RV B | | RV C | |
| | | 100% | 99-95% | 94-90% | 89-85% | Total | Total | Range (% identity) | Total | Range (% identity) |
| $VP2_{P3}$ | RGDSTITSQDVANAVVGYGV-5 | 40/77 (51.9%) | 17/77 (22.1%) | 10/77 (13.0%) | 7/77 (9.1%) | 74/77 (96.1%) | 10/29 (34.5%) | 72-67% | 1/51 (2.0%) | 72% |
| $VP2_{P2}$ | SDRIIQITRGDSTITSQDVA-7 | 50/77 (64.9%) | 8/77 (10.4%) | 13/77 (16.9%) | 2/77 (2.6%) | 73/77 (94.8%) | 23/29 (79.3%) | 65% | 21/51 (41.2%) | 78-72% |
| $VP1_{P23}$ | PRFSLPFLSIASAYYMFYDG-1 | 39/77 (50.6%) | 14/77 (18.2%) | 3/77 (3.9%) | 17/77 (22.1%) | 73/77 (94.8%) | 21/29 (72.4%) | 74-68% | 7/51 (13.7%) | 70-65% |
| $VP2_{P26}$ | VPYVNAVPMDSMVRHNNWSL-6 | 8/77 (10.4%) | 53/77 (68.8%) | 5/77 (6.5%) | 6/77 (7.8%) | 72/77 (93.5%) | 23/29 (79.3%) | 82-71% | 7/51 (13.7%) | 76-70% |
| $VP2_{P10}$ | TSKGWWWKLPDALKDMGIFG-10 | 31/77 (40.3%) | 33/77 (42.9%) | 1/77 (1.3%) | 7/77 (9.1%) | 72/77 (93.5%) | 21/29 (72.4%) | 95-84% | 4/51 (7.8%) | 89-79% |
| $VP2_{P24}$ | PHQFINLRSNNSATLIVPYV-2 | 7/77 (9.1%) | 43/77 (55.8%) | 12/77 (15.6%) | 8/77 (10.4%) | 70/77 (90.9%) | 23/29 (79.3%) | 85-70% | 7/51 (13.7%) | 75-70% |
| $VP2_{P25}$ | SNNSATLIVPYVNAVPMDsm-8 | 7/77 (9.1%) | 59/77 (76.6%) | 4/77 (5.2%) | 0/77 (0.0%) | 70/77 (90.9%) | 22/29 (75.9%) | 84-68% | 7/51 (13.7%) | 74-68% |
| $VP1_{P21}$ | QSGTNASVFWQHGQPFPRFS-9 | 2/77 (2.6%) | 16/77 (20.8%) | 21/77 (27.3%) | 29/77 (37.7%) | 68/77 (88.3%) | 0/29 (0.0%) | — | 0/51 (0.0%) | — |
| $VP2_{P21}$ | NEKQPSDDNWLNFDGTLLGN-3 | 17/77 (22.1%) | 5/77 (6.5%) | 20/77 (26.0%) | 9/77 (11.7%) | 51/77 (66.2%) | 6/29 (20.7%) | 89% | 0/51 (0.0%) | — |
| $VP1_{P18}$ | HIVMQYMYVPPGAPIPTTRN-4 | 1/77 (1.3%) | 3/77 (3.9%) | 8/77 (10.4%) | 28/77 (36.4%) | 40/77 (51.9%) | 3/29 (10.3%) | 79-54% | 0/51 (0.0%) | — |

Data for Table 2 were generated based on sequence alignments obtained by Protein BLAST using the top 5,000 results. Peptides are listed from highest to lowest "identity scores" based on their overall prevalence of identity within RV species A. Values denote the prevalence of strains within each RV species that showed amino acid sequence identity, with percentages in parentheses. The total number of RV types for each species used as the denominator is based on classifications according to McIntyre et al [62]. For RV species B and C, only the total prevalence with the corresponding range of amino acid sequence identity is shown, owing to lower sequence identities compared with RV species A.

TABLE 3

Predicted Epitopes of Validated TGEM Epitopes.

| HLA Allele | Epitope and SEQ ID NO: | Overlap[1] | Consensus Rank | SMM-Align 9mer Core | SMM-Align IC$_{50}$ | NN-Align 9mer Core | NN-Align IC$_{50}$ | Comblib/Sturniolo 9mer Core | Comblib/Sturniolo IC$_{50}$ | MULTIPRED2/NetMHCIIpan 9mer Core | MULTIPRED2/NetMHCIIpan 9mer IC$_{50}$ | MULTIPRED2/NetMHCIIpan 19mer IC$_{50}$[2] | CD8 Hits[3] |
|---|---|---|---|---|---|---|---|---|---|---|---|---|---|
| 1*0101 | VP1$_{P23}$ PRFSLPFLSIASAYYMGYDG-5 | None | 1.58 | FLSIASAYY | 11 | FLSIASAYY | 5.60 | RFSLPFLSI[5] | 15.04 | FLSIASAYY | 172.97

TABLE S1

Peptides Containing Candidate Epitopes of RV-A16 VP1 and VP2 Capsid Proteins

| HLA Allele | Epitope and SEQ ID NO: | In Vitro Frequency (% CD4)[1] | Ex Vivo Frequency (# per $10^6$ CD4)[2] | Validated |
|---|---|---|---|---|
| 1*0101 | $VP1_{P18}$ HIVMQYMYVPPGAPIPTTRN-4 | 3.51, 0, 0 | | N |
| | $VP1_{P20}$ TTRNDYAWQSGTNASVFWQH-11 | 18.7, 0, 0 | | N |
| | $VP1_{P23}$ PRFSLPFLSIASAYYMFYDG-1 | 8.37, 0.35, 2.37 | 3, 8, 13, 2 | Y |
| | $VP2_{P12}$ GIFGENMFYHFLGRSGYTVH-12 | 0.63,0, 1.23 | | N |
| | $VP2_{P22}$ NWLNFDGTLLGNLLIFPHQF-13 | 0.35, 0, 0 | | N |
| | $VP2_{P23}$ LLGNLLIFPHQFINLRSNNS-14 | 1.6, 3.19, 1.58 | | N |
| | $VP2_{P24}$ PHQFINLRSNNSATLIVPYV-2 | 2.82, 3.17, 11.3 | 17, 148, 26 | Y |
| 1*0301 | $VP2_{P21}$ NEKQPSDDNWLNFDGTLLGN-3 | 1.57, 0.87 | 29, 4, 6 | Y |
| | $VP2_{P22}$ NWLNFDGTLLGNLLIFPHQF-13 | 2.61, 0.75 | | N |
| 1*0401 | $VP1_{P14}$ QIRRKFEMFTYARFDSEITM-15 | 0.59, 0.96 | 4 | N |
| | $VP1_{P18}$ HIVMQYMYVPPGAPIPTTRN-4 | 0,0.65 | 2 | N |
| | $VP2_{P21}$ NEKQPSDDNWLNFDGTLLGN-3 | 5.13, 0.89 | 9, 63, 3 | Y |
| | $VP2_{P22}$ NWLNFDGTLLGNLLIFPHQF-13 | 3.38, 0.89 | 1 | N |
| | $VP2_{P25}$ SNNSATLIVPYVNAVPMDSM-8 | 0,0.46 | | N |
| 1*0404 | $VP1_{P17}$ AAKDGHIGHIVMQYMYVPPG-16 | 2.00, 2.99, 2.60 | 112 | N |
| | $VP1_{P18}$ HIVMQYMYVPPGAPIPTTRN-4 | 1.84, 4.22, 2.76 | 247, 10, 52, 5 | Y |
| | $VP2_{P3}$ RGDSTITSQDVANAVVGYGV-5 | 6.86, 1.61 | 36, 1, 38, 5 | Y |
| | $VP2_{P8}$ TSSNRFYTLDSKMWNSTSKG-17 | 0.77, 1.82 | 2 | N |
| | $VP2_{P15}$ ASKFHQGTLLVVMIPEHQLA-18 | 0.98, 0.81 | | N |
| | $VP2_{P21}$ NEKQPSDDNWLNFDGTLLGN-3 | 0,0.65 | | N |
| 1*0701 | $VP1_{P15}$ FTYARFDSEITMVPSVAAKD-19 | 0.26,0 | | N |
| | $VP1_{P16}$ EITMVPSVAAKDGHIGHIVM-20 | 0.60,0 | | N |
| | $VP1_{P23}$ PRFSLPFLSIASAYYMFYDG-1 | 1.84, 0.74 | 3, 8, 13, 2 | Y |
| | $VP1_{P27}$ VVTNDMGTLCSRIVTSEQLH-21 | 0,0.13 | | N |
| | $VP1_{P32}$ RPPRAVQYSHTHTTNYKLSS-22 | 0.53,0 | | N |
| | $VP2_{P26}$ VPYVNAVPMDSMVRHNNWSL-6 | 1.57, 0.84 | 4, 16, 14, 5 | Y |
| 1*1101 | $VP1_{P29}$ EQLHKVKVVTRIYHKAKHTK-23 | 3.35, 2.79 | 0, 3, 0 | N |
| | $VP2_{P1}$ PSVEACGYSDRIIQITRGDS-24 | 1.59, 1.16, 0.66 | | N |
| | $VP2_{P2}$ SDRIIQITRGDSTITSQDVA-7 | 2.18, 1.22, 2.28 | 8, 11, 15 | Y |
| | $VP2_{P8}$ TSSNRFYTLDSKMWNSTSKG-17 | 0, 0, 0.26 | | N |
| | $VP2_{P9}$ LDSKMWNSTSKGWWWKLPDA-25 | 0.22, 0, 0 | | N |
| | $VP2_{P12}$ GIFGENMFYHFLGRSGYTVH-12 | 1.55, 0, 0.38 | | N |
| | $VP2_{P22}$ NWLNFDGTLLGNLLIFPHQF-13 | 0, 1.31,0 | | N |
| 1*1501 | $VP1_{P23}$ PRFSLPFLSIASAYYMFYDG-1 | 0.28, 0.78, 0 | | N |
| | $VP1_{P24}$ SIASAYYMFYDGYDGDTYKS-26 | 0.31, 0, 0 | | N |
| | $VP2_{P15}$ ASKFHQGTLLVVMIPEHQLA-27 | 0.55, 0.53 | | N |
| | $VP2_{P16}$ LLVVMIPEHQLATVNKGNVN-28 | 0,3 | | N |
| | $VP2_{P25}$ SNNSATLIVPYVNAVPMDSM-8 | 9.02, 2.26 | 31, 5, 13, 71 | Y |
| | $VP2_{P30}$ ISNIVPITVSISPMCAEFSG-29 | 0.46, 0 | | N |
| | $VP2_{P31}$ ITVSISPMCAEFSGARAKTV-30 | 0.37,0 | | N |
| DRB5 | $VP1_{P21}$ QSGTNASVFWQHGQPFPRFS-9 | 3.91, 0.95 | 11, 28, 20 | Y |
| | $VP1_{P22}$ FWQHGQPFPRFSLPFLSIAS-31 | 3.52, 0.74 | 10,4 | N |
| | $VP1_{P23}$ PRFSLPFLSIASAYYMFYDG-1 | 2.03, 2.90 | 11 | N |
| | $VP2_{P10}$ TSKGWWWKLPDALKDMGIFG-10 | 3.93, 4.49, 0.38 | 60, 24, 136 | Y |
| | $VP2_{P24}$ PHQFINLRSNNSATLIVPYV-2 | 0, 0.67, 0 | | N |

Y means validated.

[1]Based on percentage of $CD4^+$ T cells that were tetramer-positive in PBMC cultures stimulated with corresponding peptides (n = 24).

[2]Based on tetramer staining performed directly ex vivo, without culture (n = 29).

TABLE S2

Comparison of Sequence Identities Between Full Length and Core Epitopes of Selected RV-A16 Epitopes and Rhinovirus Strains Belonging to Species A, B and C

| Epitope and SEQ ID NO: | | Identity With Other Rhinovirus Species | | | | | | | | |
|---|---|---|---|---|---|---|---|---|---|---|
| | | RV A | | | | | RV B | | RV C | |
| | | 100% | 99-95% | 94-90% | 89-85% | Sum | Hits | Range (% ID) | Hits | Range (% ID) |
| $VP1_{P21}$ SEQ: 9 | QSGTNASVFWQHGQPFPRFS | 2/78 (2.6%) | 16/78 (20.5%) | 21/78 (26.9%) | 29/78 (37.2%) | 68/78 (87.2%) | 0/30 (0.0%) | — | 0/51 (0.0%) | — |
| | QSGTNASVFWQHGQPFPRFS | 12/78 (15.4%) | 0/78 (0%) | 0/78 (0.0%) | 21/78 (26.9%) | 68/78 (42.3%) | 0/30 (0.0%) | — | 0/51 (0.0%) | — |
| $VP2_{P21}$ SEQ: 3 | NEKQPSDDNWLNFDGTLLGN | 17/78 (21.8%) | 5/78 (6.4%) | 20/78 (25.6%) | 9/78 (11.5%) | 51/78 (65.4%) | 6/30 (20.0%) | 89% | 0/51 (0.0%) | — |
| | NEKQPSDDNWLNFDGTLLGN | 53/78 (67.9%) | 0/78 (0.0%) | 0/78 (0.0%) | 6/78 (7.7%) | 59/78 (75.6%) | 6/30 (20.0%) | 88% | 0/51 (0.0%) | — |
| $VP1_{P18}$ SEQ: 4 | HIVMQYMYVPPGAPIPTTRN | 1/78 (1.3%) | 3/78 (3.8%) | 8/78 (10.3%) | 28/78 (35.9%) | 40/78 (51.3%) | 3/30 (10.0%) | 79-54% | 0/51 (0.0%) | — |
| | HIVMQYMYVPPGAPIPTTRN | 62/78 (79.5 | 0/78 (0.0%) | 0/78 (0.0%) | 10/78 (12.8%) | 72/78 (92.3%) | 0/30 (0.0%) | — | 5/51 (9.8%) | 89-78% |

Peptides analyzed were those that gave the lowest sequence identity with strains of RV species C. Data was generated based on sequence alignments obtained by Protein BLAST using the top 5,000 results. Values denote the prevalence of strains within each RV species that showed amino acid sequence identity. Values in parentheses denote corresponding percentages.

TABLE 4

(RV-39) Relationship of RV-Specific CD4+ T cell Precursor Frequency to Infection Status in DR*0401+ Subjects Undergoing Experimental Challenge

| Infected | High Frequency[1] (n = 6) | Low Frequency[2] (n = 10) |
|---|---|---|
| Yes | 3 (50%) | 9 (90%) |
| No | 3 (50%) | 1 (10%) |

[1]Frequency ≥10 Tetramer+ cells per $10^6$ CD4+ T Cells
[2]Frequency <10 Tetramer+ cells per $10^6$ CD4+ T Cells
Table 4 demonstrates the numbers of HLA-DR*0401+ subjects with "high" versus "low" T-cell numbers who were infected with RV-39 following experimental challenge with RV-39.

TABLE 5A

RV-A39- The Cox proportion hazard model summary for the analysis of time to shedding with all RV inoculated subjects included.

| Predictor | Log Hazard Ratio | Standard Error | Log Hazard Ratio LCL | Log Hazard Ratio UCL | Hazard Ratio | Hazard Ratio LCL | Hazard Ratio UCL | Chi-square Statistic | Pvalue |
|---|---|---|---|---|---|---|---|---|---|
| CD4+ TC Freq > 10 | −1.150 | 0.751 | −2.621 | 0.322 | 0.317 | 0.073 | 1.380 | 2.34 | 0.126 |

TABLE 5B

RV-A39- The Cox proportion hazard model summary for the analysis of time to RV shedding for only those subjects who were infected by RV.

| Predictor | Log Hazard Ratio | Standard Error | Log Hazard Ratio LCL | Log Hazard Ratio UCL | Hazard Ratio | Hazard Ratio LCL | Hazard Ratio UCL | Chi-square Statistic | Pvalue |
|---|---|---|---|---|---|---|---|---|---|
| CD4+ TC Freq > 10 | −1.241 | 0.904 | −3.012 | 0.530 | 0.289 | 0.049 | 1.699 | 1.886 | 0.170 |

```

What is claimed is:

1. A method for inducing an immune response against a rhinovirus (RV) or for activating antigen-experienced RV-specific CD4+ T cells in a subject, said method comprising administering to said subject a pharmaceutical composition comprising an effective amount of at least one RV peptide epitope, wherein at least one of said RV peptide epitopes is a conserved RV peptide epitope recognized by antigen-experienced RV-specific CD4+ T cells, wherein said at least one RV peptide epitope is selected from the group consisting of SEQ ID NOs:1-53, 56, and 57, and biologically active fragments and homologs of said at least one RV peptide epitope.

2. The method of claim 1, wherein said antigen-experienced RV-specific CD4+ T cells respond to cross-reactive determinants of different RV strains.

3. The method of claim 1, wherein at least two RV peptide epitopes are administered.

4. The method of claim 3, wherein at least three RV peptide epitopes are administered.

5. The method of claim 4, wherein at least five RV peptide epitopes are administered.

6. The method of claim 5, wherein at least ten RV peptide epitopes are administered.

7. The method of claim 1, where said SEQ ID NO is selected from the group consisting of SEQ ID NOs:1-10.

8. The method of claim 7, wherein each of said SEQ ID NOs:1-10 is administered.

9. The method of claim 1, wherein said composition further comprises an adjuvant.

10. The method of claim 1, wherein said RV peptide epitope is pan-specific.

11. The method of claim 1, wherein when at least two RV peptide epitopes are administered, at least one of said at least two RV peptide epitopes is an RV-A16 VP1 epitope.

12. The method of claim 1, wherein said antigen-experienced RV-specific CD4+ T cells are cross-reactive with epitopes from different RV strains.

13. The method of claim 1, wherein said antigen-experienced RV-specific CD4+ T cells target a limited set of conserved RV peptide epitopes.

14. The method of claim 1, wherein said antigen-experienced RV-specific CD4+ T cells recognize a limited set of species-specific and pan-specific epitopes.

15. The method of claim 14, wherein said RV strains are selected from the group consisting of RV species A, B, and C.

16. The method of claim 1, wherein said RV peptide epitope is an RV-A16 peptide epitope.

17. The method of claim 16, wherein said antigen-experienced RV-specific CD4+ T cells recognize conserved RV epitopes that respond to cross-reactive determinants of different RV strains.

18. The method of claim 17, wherein said antigen-experienced RV-specific CD4+ T cells are epitope-specific T cells that are Th1-like and respond to RV infection.

19. The method of claim 17, wherein said RV-A16-specific CD4+ T cells display a memory Th1 signature and respond rapidly to RV infection when contacted with an RV.

20. The method of 19, wherein said RV is RV-A16 or RV-A39.

21. The method of claim 1, wherein said method increases the number of CD4+ T cells that recognize conserved RV peptide epitopes.

22. The method of claim 21, wherein said RV peptide epitope comprises a VP1 or VP2 peptide epitope.

23. The method of claim 1, wherein said RV peptide epitopes are highly conserved across RV species A.

24. The method of claim 1, wherein said method activates CD8+ T cells.

25. A method for increasing resistance to an RV infection in a subject in need thereof, said method comprising administering to said subject a composition consisting of a pharmaceutically-acceptable carrier, an adjuvant, and at least one RV peptide epitope selected from the group consisting of SEQ ID NOs:1-58, and biologically active fragments and homologs thereof, wherein at least one of said RV peptide epitopes is a conserved RV peptide epitope recognized by antigen-experienced RV-specific CD4+ T cells.

26. The method of claim 25, wherein said composition comprises at least one RV peptide epitope selected from the group consisting of SEQ ID NOs:1-10.

27. The method of claim 26, wherein said composition consists of SEQ ID NOs:1-10.

28. The method of claim 7, wherein said at least one peptide consists of SEQ ID NO:3.

29. The method of claim 26, wherein said at least one peptide consists of SEQ ID NO:3.

* * * * *

                        SEQUENCE LISTING

<160> NUMBER OF SEQ ID NOS: 58

<210> SEQ ID NO 1
<211> LENGTH: 20
<212> TYPE: PRT
<213> ORGANISM: Human rhinovirus

<400> SEQUENCE: 1

Pro Arg Phe Ser Leu Pro Phe Leu Ser Ile Ala Ser Ala Tyr Tyr Met
1               5                   10                  15

Phe Tyr Asp Gly
            20

<210> SEQ ID NO 2
<211> LENGTH: 20
<212> TYPE: PRT
<213> ORGANISM: human rhinovirus

<400> SEQUENCE: 2

Pro His Gln Phe Ile Asn Leu Arg Ser Asn Asn Ser Ala Thr Leu Ile
1               5                   10                  15

Val Pro Tyr Val
```

<210> SEQ ID NO 3
<211> LENGTH: 20
<212> TYPE: PRT
<213> ORGANISM: Human rhinovirus

<400> SEQUENCE: 3

Asn Glu Lys Gln Pro Ser Asp Asp Asn Trp Leu Asn Phe Asp Gly Thr
1               5                   10                  15

Leu Leu Gly Asn
            20

<210> SEQ ID NO 4
<211> LENGTH: 20
<212> TYPE: PRT
<213> ORGANISM: Human rhinovirus

<400> SEQUENCE: 4

His Ile Val Met Gln Tyr Met Tyr Val Pro Pro Gly Ala Pro Ile Pro
1               5                   10                  15

Thr Thr Arg Asn
            20

<210> SEQ ID NO 5
<211> LENGTH: 20
<212> TYPE: PRT
<213> ORGANISM: Human rhinovirus

<400> SEQUENCE: 5

Arg Gly Asp Ser Thr Ile Thr Ser Gln Asp Val Ala Asn Ala Val Val
1               5                   10                  15

Gly Tyr Gly Val
            20

<210> SEQ ID NO 6
<211> LENGTH: 20
<212> TYPE: PRT
<213> ORGANISM: Human rhinovirus

<400> SEQUENCE: 6

Val Pro Tyr Val Asn Ala Val Pro Met Asp Ser Met Val Arg His Asn
1               5                   10                  15

Asn Trp Ser Leu
            20

<210> SEQ ID NO 7
<211> LENGTH: 20
<212> TYPE: PRT
<213> ORGANISM: Human rhinovirus

<400> SEQUENCE: 7

Ser Asp Arg Ile Ile Gln Ile Thr Arg Gly Asp Ser Thr Ile Thr Ser
1               5                   10                  15

Gln Asp Val Ala
            20

<210> SEQ ID NO 8
<211> LENGTH: 20
<212> TYPE: PRT
<213> ORGANISM: Human rhinovirus

<400> SEQUENCE: 8

Ser Asn Asn Ser Ala Thr Leu Ile Val Pro Tyr Val Asn Ala Val Pro
1               5                   10                  15

Met Asp Ser Met
            20

<210> SEQ ID NO 9
<211> LENGTH: 20
<212> TYPE: PRT
<213> ORGANISM: Human rhinovirus

<400> SEQUENCE: 9

Gln Ser Gly Thr Asn Ala Ser Val Phe Trp Gln His Gly Gln Pro Phe
1               5                   10                  15

Pro Arg Phe Ser
            20

<210> SEQ ID NO 10
<211> LENGTH: 20
<212> TYPE: PRT
<213> ORGANISM: Human rhinovirus

<400> SEQUENCE: 10

Thr Ser Lys Gly Trp Trp Trp Lys Leu Pro Asp Ala Leu Lys Asp Met
1               5                   10                  15

Gly Ile Phe Gly
            20

<210> SEQ ID NO 11
<211> LENGTH: 20
<212> TYPE: PRT
<213> ORGANISM: Human rhinovirus

<400> SEQUENCE: 11

Thr Thr Arg Asn Asp Tyr Ala Trp Gln Ser Gly Thr Asn Ala Ser Val
1               5                   10                  15

Phe Trp Gln His
            20

<210> SEQ ID NO 12
<211> LENGTH: 20
<212> TYPE: PRT
<213> ORGANISM: Human rhinovirus

<400> SEQUENCE: 12

Gly Ile Phe Gly Glu Asn Met Phe Tyr His Phe Leu Gly Arg Ser Gly
1               5                   10                  15

Tyr Thr Val His
            20

<210> SEQ ID NO 13
<211> LENGTH: 20
<212> TYPE: PRT
<213> ORGANISM: Human rhinovirus

<400> SEQUENCE: 13

Asn Trp Leu Asn Phe Asp Gly Thr Leu Leu Gly Asn Leu Leu Ile Phe
1               5                   10                  15

Pro His Gln Phe
            20

<210> SEQ ID NO 14

```
<211> LENGTH: 20
<212> TYPE: PRT
<213> ORGANISM: Human rhinovirus

<400> SEQUENCE: 14

Leu Leu Gly Asn Leu Leu Ile Phe Pro His Gln Phe Ile Asn Leu Arg
1               5                   10                  15

Ser Asn Asn Ser
            20

<210> SEQ ID NO 15
<211> LENGTH: 20
<212> TYPE: PRT
<213> ORGANISM: Human rhinovirus

<400> SEQUENCE: 15

Gln Ile Arg Arg Lys Phe Glu Met Phe Thr Tyr Ala Arg Phe Asp Ser
1               5                   10                  15

Glu Ile Thr Met
            20

<210> SEQ ID NO 16
<211> LENGTH: 20
<212> TYPE: PRT
<213> ORGANISM: Human rhinovirus

<400> SEQUENCE: 16

Ala Ala Lys Asp Gly His Ile Gly His Ile Val Met Gln Tyr Met Tyr
1               5                   10                  15

Val Pro Pro Gly
            20

<210> SEQ ID NO 17
<211> LENGTH: 20
<212> TYPE: PRT
<213> ORGANISM: Human rhinovirus

<400> SEQUENCE: 17

Thr Ser Ser Asn Arg Phe Tyr Thr Leu Asp Ser Lys Met Trp Asn Ser
1               5                   10                  15

Thr Ser Lys Gly
            20

<210> SEQ ID NO 18
<211> LENGTH: 20
<212> TYPE: PRT
<213> ORGANISM: Human rhinovirus

<400> SEQUENCE: 18

Ala Ser Lys Phe His Gln Gly Thr Leu Leu Val Val Met Ile Pro Glu
1               5                   10                  15

His Gln Leu Ala
            20

<210> SEQ ID NO 19
<211> LENGTH: 20
<212> TYPE: PRT
<213> ORGANISM: Human rhinovirus

<400> SEQUENCE: 19

Phe Thr Tyr Ala Arg Phe Asp Ser Glu Ile Thr Met Val Pro Ser Val
1               5                   10                  15
```

Ala Ala Lys Asp
        20

<210> SEQ ID NO 20
<211> LENGTH: 20
<212> TYPE: PRT
<213> ORGANISM: Human rhinovirus

<400> SEQUENCE: 20

Glu Ile Thr Met Val Pro Ser Val Ala Ala Lys Asp Gly His Ile Gly
1               5                   10                  15

His Ile Val Met
        20

<210> SEQ ID NO 21
<211> LENGTH: 20
<212> TYPE: PRT
<213> ORGANISM: Human rhinovirus

<400> SEQUENCE: 21

Val Val Thr Asn Asp Met Gly Thr Leu Cys Ser Arg Ile Val Thr Ser
1               5                   10                  15

Glu Gln Leu His
        20

<210> SEQ ID NO 22
<211> LENGTH: 20
<212> TYPE: PRT
<213> ORGANISM: Human rhinovirus

<400> SEQUENCE: 22

Arg Pro Pro Arg Ala Val Gln Tyr Ser His Thr His Thr Thr Asn Tyr
1               5                   10                  15

Lys Leu Ser Ser
        20

<210> SEQ ID NO 23
<211> LENGTH: 20
<212> TYPE: PRT
<213> ORGANISM: Human rhinovirus

<400> SEQUENCE: 23

Glu Gln Leu His Lys Val Lys Val Val Thr Arg Ile Tyr His Lys Ala
1               5                   10                  15

Lys His Thr Lys
        20

<210> SEQ ID NO 24
<211> LENGTH: 20
<212> TYPE: PRT
<213> ORGANISM: Human rhinovirus

<400> SEQUENCE: 24

Pro Ser Val Glu Ala Cys Gly Tyr Ser Asp Arg Ile Ile Gln Ile Thr
1               5                   10                  15

Arg Gly Asp Ser
        20

<210> SEQ ID NO 25
<211> LENGTH: 20
<212> TYPE: PRT
<213> ORGANISM: Human rhinovirus -continued

```
<400> SEQUENCE: 25

Leu Asp Ser Lys Met Trp Asn Ser Thr Ser Lys Gly Trp Trp Trp Lys
1               5                   10                  15

Leu Pro Asp Ala
            20

<210> SEQ ID NO 26
<211> LENGTH: 20
<212> TYPE: PRT
<213> ORGANISM: Human rhinovirus

<400> SEQUENCE: 26

Ser Ile Ala Ser Ala Tyr Tyr Met Phe Tyr Asp Gly Tyr Asp Gly Asp
1               5                   10                  15

Thr Tyr Lys Ser
            20

<210> SEQ ID NO 27
<211> LENGTH: 20
<212> TYPE: PRT
<213> ORGANISM: Human rhinovirus

<400> SEQUENCE: 27

Ala Ser Lys Phe His Gln Gly Thr Leu Leu Val Val Met Ile Pro Glu
1               5                   10                  15

His Gln Leu Ala
            20

<210> SEQ ID NO 28
<211> LENGTH: 20
<212> TYPE: PRT
<213> ORGANISM: Human rhinovirus

<400> SEQUENCE: 28

Leu Leu Val Val Met Ile Pro Glu His Gln Leu Ala Thr Val Asn Lys
1               5                   10                  15

Gly Asn Val Asn
            20

<210> SEQ ID NO 29
<211> LENGTH: 20
<212> TYPE: PRT
<213> ORGANISM: Human rhinovirus

<400> SEQUENCE: 29

Ile Ser Asn Ile Val Pro Ile Thr Val Ser Ile Ser Pro Met Cys Ala
1               5                   10                  15

Glu Phe Ser Gly
            20

<210> SEQ ID NO 30
<211> LENGTH: 20
<212> TYPE: PRT
<213> ORGANISM: Human rhinovirus

<400> SEQUENCE: 30

Ile Thr Val Ser Ile Ser Pro Met Cys Ala Glu Phe Ser Gly Ala Arg
1               5                   10                  15

Ala Lys Thr Val
            20
```

<210> SEQ ID NO 31
<211> LENGTH: 20
<212> TYPE: PRT
<213> ORGANISM: Human rhinovirus

<400> SEQUENCE: 31

Phe Trp Gln His Gly Gln Pro Phe Pro Arg Phe Ser Leu Pro Phe Leu
1               5                   10                  15

Ser Ile Ala Ser
            20

<210> SEQ ID NO 32
<211> LENGTH: 12
<212> TYPE: PRT
<213> ORGANISM: Human rhinovirus

<400> SEQUENCE: 32

Pro His Gln Phe Ile Asn Leu Arg Ser Asn Asn Ser
1               5                   10

<210> SEQ ID NO 33
<211> LENGTH: 12
<212> TYPE: PRT
<213> ORGANISM: Human rhinovirus

<400> SEQUENCE: 33

Asn Trp Leu Asn Phe Asp Gly Thr Leu Leu Gly Asn
1               5                   10

<210> SEQ ID NO 34
<211> LENGTH: 12
<212> TYPE: PRT
<213> ORGANISM: Human rhinovirus

<400> SEQUENCE: 34

His Ile Val Met Gln Tyr Met Tyr Val Pro Pro Gly
1               5                   10

<210> SEQ ID NO 35
<211> LENGTH: 12
<212> TYPE: PRT
<213> ORGANISM: Human rhinovirus

<400> SEQUENCE: 35

Ser Asp Arg Ile Ile Gln Ile Thr Arg Gly Asp Ser
1               5                   10

<210> SEQ ID NO 36
<211> LENGTH: 12
<212> TYPE: PRT
<213> ORGANISM: Human rhinovirus

<400> SEQUENCE: 36

Phe Trp Gln His Gly Gln Pro Phe Pro Arg Phe Ser
1               5                   10

<210> SEQ ID NO 37
<211> LENGTH: 9
<212> TYPE: PRT
<213> ORGANISM: Human rhinovirus

<400> SEQUENCE: 37

Phe Leu Ser Ile Ala Ser Ala Tyr Tyr
1               5

<210> SEQ ID NO 38
<211> LENGTH: 9
<212> TYPE: PRT
<213> ORGANISM: Human rhinovirus

<400> SEQUENCE: 38

Phe Ile Asn Leu Arg Ser Asn Asn Ser
1               5

<210> SEQ ID NO 39
<211> LENGTH: 9
<212> TYPE: PRT
<213> ORGANISM: Human rhinovirus

<400> SEQUENCE: 39

Leu Asn Phe Asp Gly Thr Leu Leu Gly
1               5

<210> SEQ ID NO 40
<211> LENGTH: 9
<212> TYPE: PRT
<213> ORGANISM: Human rhinovirus

<400> SEQUENCE: 40

Met Gln Tyr Met Tyr Val Pro Pro Gly
1               5

<210> SEQ ID NO 41
<211> LENGTH: 9
<212> TYPE: PRT
<213> ORGANISM: Human rhinovirus

<400> SEQUENCE: 41

Ile Thr Ser Gln Asp Val Ala Asn Ala
1               5

<210> SEQ ID NO 42
<211> LENGTH: 9
<212> TYPE: PRT
<213> ORGANISM: Human rhinovirus

<400> SEQUENCE: 42

Ala Val Pro Met Asp Ser Met Val Arg
1               5

<210> SEQ ID NO 43
<211> LENGTH: 9
<212> TYPE: PRT
<213> ORGANISM: Human rhinovirus

<400> SEQUENCE: 43

Ile Ile Gln Ile Thr Arg Gly Asp Ser
1               5

<210> SEQ ID NO 44
<211> LENGTH: 9
<212> TYPE: PRT
<213> ORGANISM: Human rhinovirus

<400> SEQUENCE: 44

Ile Val Pro Tyr Val Asn Ala Val Pro
1               5

<210> SEQ ID NO 45

```
<211> LENGTH: 9
<212> TYPE: PRT
<213> ORGANISM: Human rhinovirus

<400> SEQUENCE: 45

Trp Gln His Gly Gln Pro Phe Pro Arg
1               5

<210> SEQ ID NO 46
<211> LENGTH: 9
<212> TYPE: PRT
<213> ORGANISM: Human rhinovirus

<400> SEQUENCE: 46

Trp Trp Lys Leu Pro Asp Ala Leu Lys
1               5

<210> SEQ ID NO 47
<211> LENGTH: 9
<212> TYPE: PRT
<213> ORGANISM: Human rhinovirus

<400> SEQUENCE: 47

His Ile Val Met Gln Tyr Met Tyr Val
1               5

<210> SEQ ID NO 48
<211> LENGTH: 9
<212> TYPE: PRT
<213> ORGANISM: Human rhinovirus

<400> SEQUENCE: 48

Thr Ile Thr Ser Gln Asp Val Ala Asn
1               5

<210> SEQ ID NO 49
<211> LENGTH: 9
<212> TYPE: PRT
<213> ORGANISM: Human rhinovirus

<400> SEQUENCE: 49

Met Val Arg His Asn Asn Trp Ser Leu
1               5

<210> SEQ ID NO 50
<211> LENGTH: 8
<212> TYPE: PRT
<213> ORGANISM: Human rhinovirus

<400> SEQUENCE: 50

Leu Ile Val Pro Tyr Asn Ala Val
1               5

<210> SEQ ID NO 51
<211> LENGTH: 9
<212> TYPE: PRT
<213> ORGANISM: Human rhinovirus

<400> SEQUENCE: 51

Arg Phe Ser Leu Pro Phe Leu Ser Ile
1               5

<210> SEQ ID NO 52
<211> LENGTH: 9
<212> TYPE: PRT
```

```
<213> ORGANISM: Human rhinovirus

<400> SEQUENCE: 52

Leu Arg Ser Asn Asn Ser Ala Thr Leu
1               5

<210> SEQ ID NO 53
<211> LENGTH: 8
<212> TYPE: PRT
<213> ORGANISM: Human rhinovirus

<400> SEQUENCE: 53

Ile Val Pro Tyr Asn Ala Val Pro
1               5

<210> SEQ ID NO 54
<211> LENGTH: 289
<212> TYPE: PRT
<213> ORGANISM: Human rhinovirus

<400> SEQUENCE: 54

Pro Ile Thr Gln Asn Pro Val Glu Arg Tyr Val Asp Glu Val Leu Asn
1               5                   10                  15

Glu Val Leu Val Val Pro Asn Ile Asn Gln Ser His Pro Thr Thr Ser
                20                  25                  30

Asn Ala Ala Pro Val Leu Asp Ala Ala Glu Thr Gly His Thr Asn Lys
            35                  40                  45

Ile Gln Pro Glu Asp Thr Ile Glu Thr Arg Tyr Val Gln Ser Ser Gln
        50                  55                  60

Thr Leu Asp Glu Met Ser Val Glu Ser Phe Leu Gly Arg Ser Gly Cys
65                  70                  75                  80

Ile His Glu Ser Val Leu Asp Ile Val Asp Asn Tyr Asn Asp Gln Ser
                85                  90                  95

Phe Thr Lys Trp Asn Ile Asn Leu Gln Glu Met Ala Gln Ile Arg Arg
            100                 105                 110

Lys Phe Glu Met Phe Thr Tyr Ala Arg Phe Asp Ser Glu Ile Thr Met
        115                 120                 125

Val Pro Ser Val Ala Ala Lys Asp Gly His Ile Gly His Ile Val Met
    130                 135                 140

Gln Tyr Met Tyr Val Pro Pro Gly Ala Pro Ile Pro Thr Thr Arg Asp
145                 150                 155                 160

Asp Tyr Ala Trp Gln Ser Gly Thr Asn Ala Ser Val Phe Trp Gln His
                165                 170                 175

Gly Gln Pro Phe Pro Arg Phe Ser Leu Pro Phe Leu Ser Ile Ala Ser
            180                 185                 190

Ala Tyr Tyr Met Phe Tyr Asp Gly Tyr Asp Gly Asp Thr Tyr Lys Ser
        195                 200                 205

Arg Tyr Gly Thr Val Val Thr Asn Asp Met Gly Thr Leu Cys Ser Arg
    210                 215                 220

Ile Val Thr Ser Glu Gln Leu His Lys Val Lys Val Thr Arg Ile
225                 230                 235                 240

Tyr His Lys Ala Lys His Thr Lys Ala Trp Cys Pro Arg Pro Arg
                245                 250                 255

Ala Val Gln Tyr Ser His Thr His Thr Thr Asn Tyr Lys Leu Ser Ser
            260                 265                 270

Glu Val His Asn Asp Val Ala Ile Arg Pro Arg Thr Asn Leu Thr Thr
        275                 280                 285
```

Val

```
<210> SEQ ID NO 55
<211> LENGTH: 261
<212> TYPE: PRT
<213> ORGANISM: Human rhinovirus

<400> SEQUENCE: 55
```

Ser Pro Ser Val Glu Ala Cys Gly Tyr Ser Asp Arg Ile Ile Gln Ile
1               5                   10                  15

Thr Arg Gly Asp Ser Thr Ile Thr Ser Gln Asp Val Ala Asn Ala Val
            20                  25                  30

Val Gly Tyr Gly Val Trp Pro His Tyr Leu Thr Pro Gln Asp Ala Thr
        35                  40                  45

Ala Ile Asp Lys Pro Thr Gln Pro Asp Thr Ser Ser Asn Arg Phe Tyr
    50                  55                  60

Thr Leu Asp Ser Lys Met Trp Asn Ser Thr Ser Lys Gly Trp Trp Trp
65                  70                  75                  80

Lys Leu Pro Asp Ala Leu Lys Asp Met Gly Ile Phe Gly Glu Asn Met
                85                  90                  95

Phe Tyr His Phe Leu Gly Arg Ser Gly Tyr Thr Val His Val Gln Cys
            100                 105                 110

Asn Ala Ser Lys Phe His Gln Gly Thr Leu Leu Val Val Met Ile Pro
        115                 120                 125

Glu His Gln Leu Ala Thr Val Asn Lys Gly Asn Val Asn Ala Gly Tyr
130                 135                 140

Lys Tyr Thr His Pro Gly Glu Ala Gly Arg Glu Val Gly Thr Gln Val
145                 150                 155                 160

Glu Asn Glu Lys Gln Pro Ser Asp Asp Asn Trp Leu Asn Phe Asp Gly
                165                 170                 175

Thr Leu Leu Gly Asn Leu Leu Ile Phe Pro His Gln Phe Ile Asn Leu
            180                 185                 190

Arg Ser Asn Asn Ser Ala Thr Leu Ile Val Pro Tyr Val Asn Ala Val
        195                 200                 205

Pro Met Asp Ser Met Val Arg His Asn Asn Trp Ser Leu Val Ile Ile
    210                 215                 220

Pro Val Cys Gln Leu Gln Ser Asn Asn Ile Ser Asn Ile Val Pro Ile
225                 230                 235                 240

Thr Val Ser Ile Ser Pro Met Cys Ala Glu Phe Ser Gly Ala Arg Ala
                245                 250                 255

Lys Thr Val Val Gln
            260

```
<210> SEQ ID NO 56
<211> LENGTH: 20
<212> TYPE: PRT
<213> ORGANISM: Human rhinovirus

<400> SEQUENCE: 56
```

Ala Gln Val Arg Arg Lys Phe Glu Met Phe Thr Tyr Val Arg Phe Asp
1               5                   10                  15

Ser Glu Ile Thr
            20

```
<210> SEQ ID NO 57
<211> LENGTH: 20
```

```
<212> TYPE: PRT
<213> ORGANISM: Human rhinovirus

<400> SEQUENCE: 57

Ser Asp Asp Asn Trp Leu Asn Phe Asp Gly Thr Leu Leu Gly Asn Leu
1               5                   10                  15

Leu Ile Phe Pro
            20

<210> SEQ ID NO 58
<211> LENGTH: 727
<212> TYPE: PRT
<213> ORGANISM: Human rhinovirus

<400> SEQUENCE: 58

Gly Gly Ser Val Ile Lys Tyr Phe Asn Ile Asn Tyr Tyr Lys Asp Ser
1               5                   10                  15

Ala Ser Ser Gly Leu Thr Lys Gln Asp Phe Ser Gln Asp Pro Ser Lys
                20                  25                  30

Phe Thr Gln Pro Ile Ala Asp Val Leu Thr Asn Pro Ala Leu Met Ser
            35                  40                  45

Pro Thr Val Glu Ala Cys Gly Phe Ser Asp Arg Leu Lys Gln Ile Thr
50                  55                  60

Ile Gly Asn Ser Thr Ile Thr Thr Gln Asp Ser Leu Asn Thr Ile Val
65                  70                  75                  80

Ala Tyr Gly Glu Trp Pro Glu Tyr Leu Ser Asp Leu Asp Ala Thr Ser
                85                  90                  95

Val Asp Lys Pro Thr His Pro Glu Thr Ser Ser Asp Arg Phe Tyr Thr
            100                 105                 110

Leu Glu Ser Val Met Trp His Gly Ser Ser Arg Gly Trp Trp Trp Lys
        115                 120                 125

Ile Pro Asp Cys Leu Lys Asp Met Gly Met Phe Gly Gln Asn Met Tyr
130                 135                 140

His His Ser Met Gly Arg Ser Gly Met Leu Ile His Val Gln Cys Asn
145                 150                 155                 160

Ala Thr Lys Phe His Ser Gly Cys Leu Leu Val Val Val Val Pro Glu
                165                 170                 175

His Gln Leu Ala Tyr Ile Gly Ala Gly Gly Val Asn Val Lys Tyr Glu
            180                 185                 190

His Thr His Pro Gly Glu Arg Gly His Thr Leu Gln Ala Ser Asp Val
        195                 200                 205

Arg Ser Asn His Asn Pro Asp Glu Asp Pro Phe Tyr Leu Cys Asn Gly
210                 215                 220

Thr Leu Leu Gly Asn Ala Leu Ile Tyr Pro His Gln Met Ile Asn Leu
225                 230                 235                 240

Arg Thr Asn Asn Ser Ala Thr Ile Val Val Pro Tyr Ile Asn Cys Val
                245                 250                 255

Pro Met Asp Asn Met Leu Arg His Asn Asn Val Ser Leu Leu Ile Ile
            260                 265                 270

Pro Ile Val Pro Leu Lys Ala Asn Thr Asp Ala Val Asn Ser Leu Pro
        275                 280                 285

Ile Thr Val Thr Ile Ala Pro Asp Lys Ser Glu Phe Ser Gly Ala Met
    290                 295                 300

Lys Ser Gln Gln Gln Gly Leu Pro Thr Arg Ser Pro Ala Gly Ser Gln
305                 310                 315                 320
```

```
Gln Phe Met Thr Thr Glu Asp Glu Gln Ser Pro Asn Ile Leu Pro Glu
                325                 330                 335

Tyr Ser Pro Thr Lys Met Ile His Ile Pro Gly Arg Ile Asp Asn Ile
            340                 345                 350

Leu His Ile Ala Met Val Glu Ser Leu Ile Pro Leu Asn Asn Ile Pro
        355                 360                 365

Gly Gln Val Gly Thr Val Gly Met Tyr Asn Val Thr Ile Ala Ser Lys
    370                 375                 380

Thr Ala Asp Gln Asp Met Ile Leu Ala Ile Pro Leu Gln Met Asp Asn
385                 390                 395                 400

Thr Leu Phe Ala Thr Thr Leu Val Gly Glu Ile Leu Asn Tyr Phe Ser
                405                 410                 415

Asn Trp Ser Gly Ser Ile Arg Val Thr Cys Ile Cys Val Cys Asp Ser
            420                 425                 430

Phe Ser Thr Gly Lys Phe Leu Met Ala Tyr Thr Pro Pro Gly Gly Gly
        435                 440                 445

Leu Pro Thr Thr Arg Lys Glu Ala Met Leu Gly Val His Val Val Trp
    450                 455                 460

Asp Leu Gly Leu Gln Ser Ser Cys Thr Leu Val Ala Pro Trp Met Ser
465                 470                 475                 480

Ser Thr Phe Tyr Arg Arg Thr Lys Gly Ser Asn Tyr Thr Ser Gly Gly
                485                 490                 495

Tyr Ile Thr Leu Trp Tyr Gln Thr Asn Phe Val Ala Thr Thr Thr Gly
            500                 505                 510

Gly Thr Gly Thr Ile Ile Ala Thr Cys Ser Ala Cys Pro Asp Leu Ser
        515                 520                 525

Val Arg Met Met Arg Asp Thr Pro Met Ile Lys Gln Pro Glu Asn Asn
    530                 535                 540

Ile Gln Asn Pro Val Asp Asn Phe Val Asp Glu Val Leu Lys Glu Val
545                 550                 555                 560

Leu Val Val Pro Asp Thr Lys Pro Ser Gly Pro Thr His Thr Val Lys
                565                 570                 575

Pro Thr Val Leu Asn Ala Met Glu Ile Gly Val Thr Pro Asp Ala Thr
            580                 585                 590

Pro Glu Ser Val Ile Glu Thr Arg Tyr Val Ile Asn Asn His Thr Asn
        595                 600                 605

Asn Glu Ala Leu Met Glu Asn Phe Leu Gly Arg Ser Ser Leu Trp Ala
    610                 615                 620

Glu Leu Gln Met Ser Asp Gly Phe Lys Lys Trp Asp Ile Asn Phe Gln
625                 630                 635                 640

Glu Gln Ala His Ile Arg Lys Lys Ile Glu Met Phe Thr Tyr Ile Arg
                645                 650                 655

Phe Asp Met Glu Val Thr Ile Val Thr Asn Asn Gln Gly Leu Met Gln
            660                 665                 670

Ile Met Tyr Val Pro Pro Gly Ile Glu Ala Pro Glu Ser Leu Asn Asp
        675                 680                 685

Lys Arg Trp Asn Gly Ala Ser Asn Pro Ser Val Phe Tyr Gln Pro Lys
    690                 695                 700

Ser Gly Phe Pro Arg Phe Thr Ile Pro Phe Thr Gly Leu Gly Ser Ala
705                 710                 715                 720

Tyr Tyr Val Phe Tyr Asp Gly
                725
```